(12) United States Patent
Dominguez et al.

(10) Patent No.: US 7,582,631 B2
(45) Date of Patent: Sep. 1, 2009

(54) SUBSTITUTED HETEROCYCLIC COMPOUNDS AND METHODS OF USE

(75) Inventors: Celia Dominguez, Thousand Oaks, CA (US); Anthony Reed, Oxnard, CA (US); Kelvin K. C. Sham, Thousand Oaks, CA (US); Maya C. Thaman, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 726 days.

(21) Appl. No.: 11/034,042

(22) Filed: Jan. 11, 2005

(65) Prior Publication Data

US 2005/0182072 A1 Aug. 18, 2005

Related U.S. Application Data

(60) Provisional application No. 60/536,617, filed on Jan. 14, 2004.

(51) Int. Cl.
*A61K 31/4995* (2006.01)
*C07D 471/08* (2006.01)
*C07D 487/08* (2006.01)

(52) U.S. Cl. ..................... 514/248; 544/349

(58) Field of Classification Search ................. 514/249, 514/349; 544/349
See application file for complete search history.

(56) References Cited

U.S. PATENT DOCUMENTS 5,776,932 A * 7/1998 Schindler et al. ......... 514/235.2
2005/0272735 A1* 12/2005 Xie et al. .................... 514/249

FOREIGN PATENT DOCUMENTS

| EP | 039051 | 7/1985 |
|---|---|---|
| EP | 1 454 908 | 9/2004 |
| WO | WO 03/044021 | 5/2003 |
| WO | WO 03082859 | 9/2003 |
| WO | WO 03/094831 | 11/2003 |
| WO | WO 2004067516 | 12/2004 |

* cited by examiner

*Primary Examiner*—James O Wilson
*Assistant Examiner*—Tamthom N Truong
(74) *Attorney, Agent, or Firm*—G. Prabhakar Reddy

(57) ABSTRACT

The present invention relates to therapeutic diazobicyclo pyridines and their use in the treatment of arthritis, rheumatoid arthritis, psoriatic arthritis or osteoarthritis, organ transplant, acute transplant or heterograft and homograft rejection, ischemic and reperfusion injury, transplantation tolerance induction, multiple sclerosis, inflammatory bowel disease, ulcerative colitis, Crohn's disease, lupus, graft vs. host diseases, T-cell mediated hypersensitivity diseases, contact hypersensitivity, delayed-type hypersensitivity, gluten-sensitive enteropathy, Type 1 diabetes, psoriasis, contact dermatitis, Hashimoto's thyroiditis, Sjogren's syndrome, autoimmune hyperthyroidism, Graves' Disease, Addison's disease, autoimmune polyglandular disease, autoimmune alopecia, pernicious anemia, vitiligo, autoimmune hypopituatarism, Guillain-Barre syndrome, autoimmune diseases, glomerulonephritis, serum sickness, uticaria, respiratory allergies, asthma, hayfever, allergic rhinitis, skin allergies, scleracielma, mycosis fungoides, acute inflammatory responses, acute respiratory distress syndrome, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea, Type II diabetes and cancers where PKC theta or other PKC-family kinases are activated, overexpressed or facilitate tumor growth or survival of tumor cells, T cell leukemia, thymoma, T and B cell lymphoma, colon carcinoma, breast carcinoma and lung carcinoma or provides resistance to chemotherapeutic drugs.

9 Claims, No Drawings

SUBSTITUTED HETEROCYCLIC COMPOUNDS AND METHODS OF USE

This application claims the benefit of U.S. Provisional Application No. 60/536,617 filed Jan. 14, 2004, which is hereby incorporated by reference.

BACKGROUND OF THE INVENTION

T cells play a key role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR) which is expressed on the cell surface. This activation triggers a series of intracellular signaling cascades mediated by enzymes expressed within the cell (Kane, L P et al. Current Opinion in Immunol. 200, 12, 242). These cascades lead to gene regulation events that result in the production of cytokines, like interleukin-2(IL-2). IL-2 is a critical cytokine in T cell activation, leading to proliferation and amplification of specific immune responses.

One class of enzymes shown to be important in signal transduction is the kinase proteins. PKC enzymes are members of a distinct family of serine/threonine protein kinases that contain nine members (isotype $\alpha$, $\beta$, $\gamma$, $\delta$, $\epsilon$, $\zeta$, $\eta$, $\theta$, $\iota$)(reviewed in Nishizuka Y., Science 1992; 258:607-614), some of which are expressed at particular high levels in T cells (including $\alpha$, $\delta$, $\epsilon$, $\eta$, $\theta$)(reviewed in Baier, G., Immunological Reviews 2003 192:64-79). Gene disruption studies suggest that inhibition of some members of the PKC family of kinases would potentially lead to therapeutic benefit. PKC$\alpha$ (−/−) mice and mice deficient in PKC$\theta$ both have T cell defects (Baier, G., Immunological Reviews 2003 192:64-79; Pfeifhofer C. et. al, Journal of Experimental Medicine, 197: 1525-1535;Sun, Nature 2000, 404:402-407), suggesting that inhibition of either of these kinases would be useful in diseases of T cell mediated inflammation and autoimmunity. PKC$\theta$ in particular may be a prime target for novel anti-inflammatory or immuno-suppressive therapies, due to its restricted tissue-expression and its nonredundant critical role in TCR-mediated IL-2 secretion (N. Isakov and A. Ammon Annu. Rev. Immunol. 2002 20:761-94). Small molecule drugs selectively inhibiting PKC$\theta$ and/or other certain other PKC isoenzymes such as PKC alpha, beta, epsilon and zeta may manifest improved efficacy and/or improved side-effect profile over drugs targeted against other immune-mediators suc has calcineurin and Akt1/PKBalpha. For example, a dual inhibitor of both PKC theta and PKC alpha may effectively prevent mature T cell activation.

PKC alpha, like PKC theta, is involved in TCR signaling in T cells (Iwamoto 1992 JBC 267:18644-18648; Ohkusu 1997 J. Immunol. 159:2082-2084). PKC family kinases are also important for signaling downstream of other immune cell receptors. PKC beta participates in B cell receptor signaling (Leitges M. et al. 1996Science 273:788-791), neutrophils (Dekker L V et al. 2000 Biochem. J. 347:285-289), and mast cells (Nechushian H et al. 2000 Blood 95:1752-1757). PKC zeta also plays a role in B cell signaling and function (Martin P. et al. 2002 EMBO J. 15:4049-4057) and PKC epsilon is required for macrophage activation (Castrillo A. et al. 2001 J. Exp. Med. 194:1231-1242). These findings suggest that PKC family kinase inhibitors may be useful in treating inflammatory, autoimmune and allergic diseases and asthma.

In addition to its essential function in mature T cell activation and IL-2secretion, PKC theta provides a survival signal that protects leukemic T cells from Fas-ligand induced apoptosis (M. Villalba and A. Altman 2002 Current Cancer Drug Targets 2:125-134). This feature and the constitutive membrane location of PKC theta in some leukemic T cells suggest that it plays a role in the growth and survival of leukemic T-cells. Furthermore, the high-affinity IL2 receptor (IL-2R alpha) is constitutively expressed by some malignant T cell leukemias suggesting that expansion of these cells may be supported by an IL-2 autocrine loop (M. Villalba and A. Altman 2002 Current Cancer Drug Targets 2:125-134). PKC theta may also promote survival of malignant cells by functioning in development of a multidrug resistance (MDR) phenotype. PKC theta expression is positively correlated with the expression of some genes involved in MDR including MDR1and MRP1 in acute myelogenous leukemia patients (Beck J. et al. 1996 Leukemia 10:426-433) and PKC theta regulates MDR1 promoter activity in human breast carcinoma cells (Gill P. K. et al. 2001 Eur. J. Biochem 268:4151-4157). Therefore, a PKC theta small molecule inhibitor may facilitate elimination of leukemic T cells and other malignant cells that over-express PKC theta. Concomitant overexpression/activation of both PKC alpha and PKC theta has also been implicated in development of multi-drug resistance. Therefore a dual PKC theta and PKC alpha small molecule inhibitor may also facilitate elimination of malignant cells that overexpress both PKC alpha and PKC theta.

Other groups have published on inhibitors of PKC family kinase and the activities of these inhibitors in various in vitro and in vivo biological systems. For example, PCT Publication No. WO 2004067516 discloses 2,4-diaminopyrimidine derivatives useful as inhibitors of PKC-theta. WO 2003082859 discloses indolylmaleimide derivatives as compounds useful in the treatment and/or prevention of diseases or disorders mediated by T-lymphocytes and/or PKC. The protein kinase C beta inhibitor ruboxistaurin (LY-333531), the lead compound from a series of 14-membered macrocycles, is being developed for the potential treatment of diabetic retinopathy, diabetic macular edema and diabetic neuropathy (Investigational Drug database, Dec. 19, 2003, Ruboxistaurin update). By October 2003, this compound was also being investigated as a potential treatment for cardiovascular disease in diabetic patients. It was in phase III trials for both diabetic retinopathy and macular edema by early 2001.

BRIEF DESCRIPTION OF THE INVENTION

The compounds disclosed in the present invention possess pharmacological activity not only by virtue of an effect on a single biological process, but it is believed that the compounds modulate T cell activation by way of inhibition of one or more of the multiple protein kinases involved in early signal transduction steps leading to T cell activation, for example by way of inhibition of PKC theta kinase.

The compounds of the present invention inhibit serine threonine kinases, especially PKC theta and to a varying degree other PKC isoenzyes, and are thus useful in the treatment, including prevention and therapy, of protein serine/threonine kinase-associated disorders such as immunologic disorders. "Protein serine-threonine kinase-associated disorders" are those disorders which result from aberrant serine-threonine kinase activity, and/or which are alleviated by the inhibition of one or more of these enzymes. For example, PKC theta inhibitors are of value in the treatment of a number of such disorders (for example, the treatment of autoimmune diseases), as PKC theta inhibition blocks T cell activation. The treatment of T cell mediated diseases, including inhibition of T cell activation and proliferation, is a preferred embodiment of the present invention. Compounds of the present invention which selectively block T cell activation and proliferation are preferred. Also, compounds of the present invention which may block the activation of endothelial cell protein serine-threonine kinase by oxidative stress, thereby limiting surface expression of adhesion molecules that induce neutrophil binding, and which can inhibit protein serine-threonine kinase necessary for neutrophil activation would be useful, for example, in the treatment of ischemia and reperfusion injury.

The present invention also provides methods for the treatment of protein serine-threonine kinase-associated disorders, comprising the step of administering to a subject, such as to those in need thereof, at least one compound of the present invention in an amount effective therefore. The compound(s) may be administered in a pharmaceutical formulation, having been formulated with a suitable pharmaceutically acceptable carrier. Other therapeutic agents such as those described below may be employed with the inventive compounds in the present methods. In the methods of the present invention, such other therapeutic agent(s) may be administered prior to, simultaneously with or following the administration of the compound(s) or pharmaceutical composition of the present invention.

Use of the compound(s) of the present invention in treating protein serine-threonine kinase-associated disorders is exemplified by, but is not limited to, treating a range of disorders such as: arthritis (such as rheumatoid arthritis, psoriatic arthritis or osteoarthritis); transplant (such as organ transplant, acute transplant or heterograft or homograft (such as is employed in bum treatment)) rejection; protection from ischemic or reperfusion injury such as ischemic or reperfusion injury incurred during organ transplantation, myocardial infarction, stroke or other causes; transplantation tolerance induction; multiple sclerosis; inflammatory bowel disease, including ulcerative colitis and Crohn's disease; lupus (systemic lupus erythematosis); graft vs. host diseases; T -cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where PKC theta or other PKC-family kinases such as PKC alpha are activated or overexpressed, such as T cell leukemia, thymoma, T and B cell lymphoma, colon carcinoma, breast cancer and lung carcinoma, or cancers where PKC-family kinase activity facilitates tumor growth or survival or provides resistance to chemotherapeutic drugs or radiation; glomerulonephritis, serum sickness; uticaria; allergic diseases such as respiratory allergies (asthma, hayfever, allergic rhinitis) or skin allergies; scleroderma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea;, type II diabes; insulin resistance; diabetic retinopathy; diabetic macular edema; diabetic neuropathy; and cardiovascular disease in diabetic patients. The present invention also provides for a method for treating the aforementioned disorders such as atopic dermatitis by administration of a therapeutically effective amount of a compound of the present invention, which is an inhibitor of protein serine-threonine kinase, to a patient in need of such treatment.

Other PKC-family kinases, such as PKC beta and zeta are also important in B cell function (Leitges M. et al. 1996Science 273:788-791; Martin P. et al. 2002EMBO J. 15:4049-4057). This activity would result in additional anti-autoimmune activity for the present compounds in addition to their effects on T cells. This activity would be especially of value, for example, in the treatment of autoimmune/inflammatory diseases, such as lupus, arthritis or inflammatory bowel disease. PKC theta may also function in B-cells (Krappmann D. 2001 Molecular & Cellular Biology. 21:6640-6650). PKC theta is also expressed in mast cells and PKC beta and epsilon plays a role in neutrophils/mast cell and macrophage function respectively. The ability to inhibit neutrophil, monocyte and macrophage responses would result in further anti-inflammatory activity for the present compounds in addition to their effects on T cells. The present compounds may also be of value for the treatment of autoimmune glomerulonephritis and other instances of glomerulonephritis induced by deposition of immune complexes in the kidney.

In addition, certain PKC isoenzymes including PKC theta and beta may function in degranulation of mast cells and basophils that plays an important role in asthma, allergic rhinitis, and other allergic disease. The ability to inhibit mast cell and basophil responses may result in additional anti-inflammatory activity for the present compounds beyond their effect on T cells.

The combined activity of the present compounds towards B cells, monocytes, macrophages, T cells, mast cells, endothelial cells, etc. may prove to be a valuable tool in the treatment of any of the aforementioned disorders.

In a particular embodiment, the compounds of the present invention are useful for the treatment of the aforementioned exemplary disorders irrespective of their etiology, for example, for the treatment of rheumatoid arthritis, transplant rejection, multiple sclerosis, inflammatory bowel disease, lupus, graft v. host disease, T cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with serine-threonine kinases.

PKC theta and certain other PKC isoenzymes are abnormally activated in the skeletal muscle of human patients with type II diabetes as well as in skeletal muscle of a rodent model of high fat induced insulin resistance (Gray S. et al. 2003European Journal of Clinical Investigation 33:983-987 and references therein). Furthermore a small molecule inhibitor of PKC beta is in late stage clinical trials for treatment of diabetic retinopathy, neuropathy and macular degeneration (IDDB: ruboxistaurin LY-333531). The ability of the present compounds to inhibit abnormal PKC theta and other PKC isoenzyme activity associated with development of insulin resistance, type II diabetes and side-effects thereof may result in a therapeutically beneficial reversal of insulin resistance and retinopathy associated with type II diabetes.

Abnormal activation of PKC theta and other PKC isoenzyrnes such as PKC alpha has been associated with the development of multidrug resistance (Beck J. et al. 1996 Leukemia 10:426-433; Gill P.K. et al. 2001 Eur. J. Biochem 268:4151-4157). The present compounds may be used to increase the potency of other medicines such as for instance chemotherapeutic drugs in cancer patients.

In addition to T cells, mast cells and skeletal muscle, PKC theta is also specifically expressed in platelets (Chang JD et al. 1993 Journal of Biological Chemistry. 268:14208-14214). The present compounds, bye virtue of inhibiting PKC theta may be used therapeutically to prevent or treat adverse thromboembolic events by regulating platelet activation.

Inhibitors of PKC isoenzymes such as PKC beta also inhibit angiogenesis in solid tumor models in rodents in vivo (IDDB: LY-317615 Update Nov. 24th 2003; Teicher BA at al. *International Journal of Antimicrobial Agents* 2001, 17:Suppl 1 Abs S6.03). The present compounds may have a therapeutic effect in solid tumors such as brain, breast, ovarian, gastric, non small-cell lung cancer, small-cell lung cancer, gastric, hepatocellular, colon and renal cell cancer by decreasing the number of intratumoral vessels.

Inhibitors of PKC isoenzymes such as PKC alpha, theta and beta inhibit growth of T and/or B cells and may be useful in treating leukocytic cancers including B and T cell lymphomas and leukemias (IDDB summary: LY-317615).

The compounds of the invention are represented by the following general

Formula: Formula I

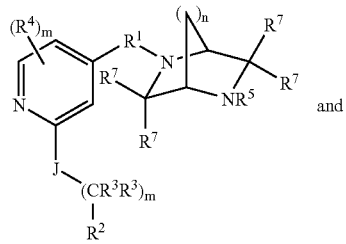

and

Formula II:

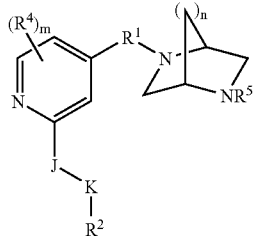

wherein $R^1$, $R^2$, $R^3$, $R^4$, $R^5$, $R^7$, J, K, m and n are defined herein.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with one embodiment of the present invention, there are provided compounds of formula I:

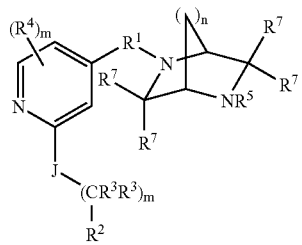

or a pharmaceutically acceptable salt thereof, wherein
J is NH, N($R^b$), O or S;
m is independently at each instance 0, 1, 2 or 3;
n is 1 or 2;
$R^1$ is selected from

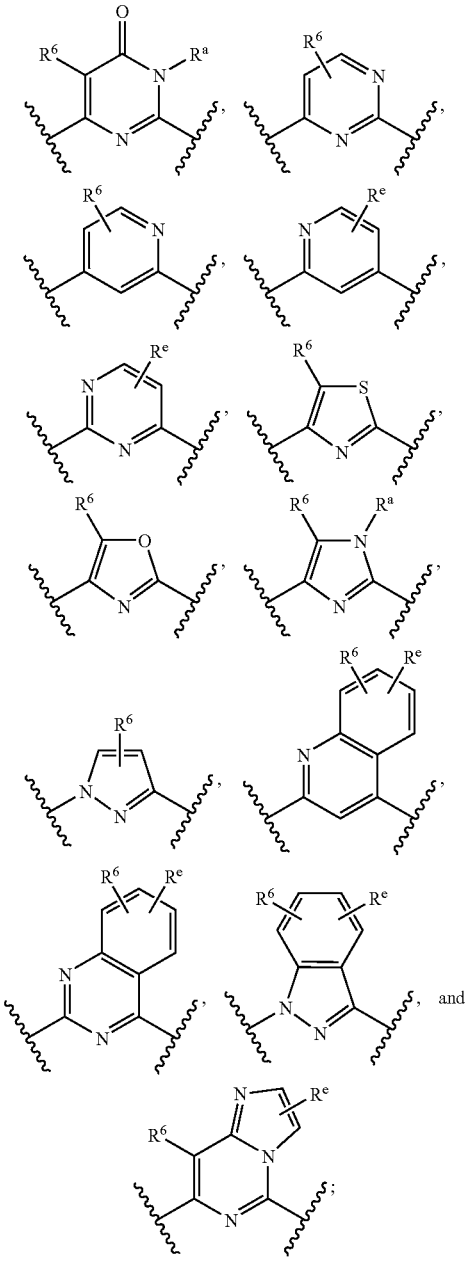

$R^2$ is a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O) O$R^b$, —S(=O)$_2$N($R^a$)C(=O)N$R^aR^a$, —N$R^aR^a$, —N($R^a$)C(=O)

$R^b$, —N($R^a$)C(=O)O$R^b$, —N($R^a$)C(=O)NR$^a$R$^a$, —N($R^a$)C(=NR$^a$)NR$^a$R$^a$, —N($R^a$)S(=O)$_2$R$^b$, —N($R^a$)S(=O)$_2$NR$^a$R$^a$, —NR$^a$C$_{2-6}$alkylNR$^a$R$^a$ and —NR$^a$C$_{2-6}$alkylOR$^a$;

$R^3$ is independently at each instance H, C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

$R^4$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$Ra or —NR$^a$C$_{2-6}$alkylOR$^a$;

$R^5$ is H or C$_{1-6}$alkyl substituted by 0, 1, 2 or 3 substituents independently selected from R$^d$ and additionally substituted by 0 or 1 substituents selected from R$^f$;

$R^6$ is H, R$^f$, R$^d$, or a C$_{1-6}$alkyl substituted by 1, 2 or 3 substituents independently selected from R$^d$ and additionally substituted by 0 or 1 substituents selected from R$^f$;

$R^7$ is independently, at each instance, H or C$_{1-6}$alkyl;

$R^a$ is independently, at each instance, H or R$^b$;

$R^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, and —N(C$_{1-4}$alkyl)C$_{1-4}$alkyl;

$R^c$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

$R^e$ is independently at each instance R$^d$ or H; and $R^f$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1 or 2 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylN-R$^a$R$^a$ and —NR$^a$C$_{2-6}$alkylOR$^a$.

In another embodiment, in conjunction with the above and below embodiments, J is NH.

In another embodiment, in conjunction with the above and below embodiments, J is N(R$^b$).

In another embodiment, in conjunction with the above and below embodiments, J is O.

In another embodiment, in conjunction with the above and below embodiments, n is 1.

In another embodiment, in conjunction with the above and below embodiments, n is 2.

In another embodiment, in conjunction with the above and below embodiments, R$^1$ is selected from

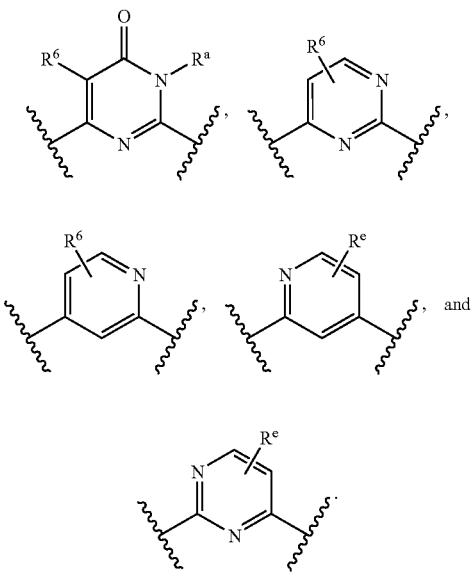

In another embodiment, in conjunction with the above and below embodiments, R$^1$ is selected from

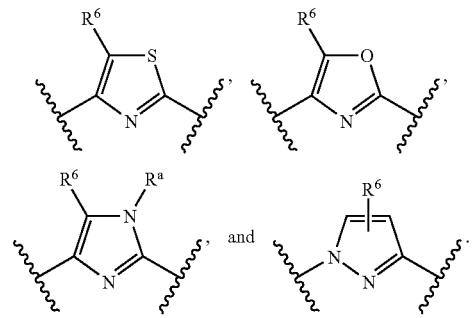

In another embodiment, in conjunction with the above and below embodiments, $R^1$ is selected from

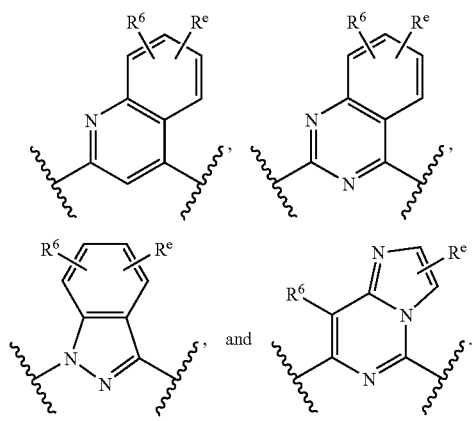

In another embodiment, in conjunction with the above and below embodiments, $R^1$ is

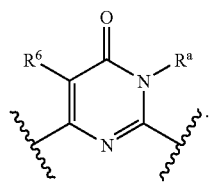

In another embodiment, in conjunction with the above and below embodiments, $R^1$ is

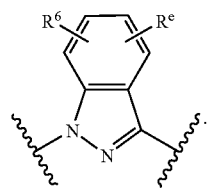

In another embodiment, in conjunction with the above and below embodiments, $R^1$ is

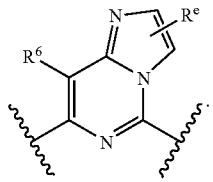

In another embodiment, in conjunction with the above and below embodiments, $R^1$ is selected from

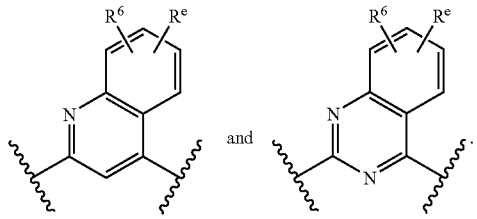

In another embodiment, in conjunction with the above and below embodiments, $R^1$ is

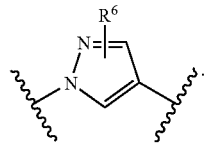

In another embodiment, in conjunction with the above and below embodiments, $R^1$ is

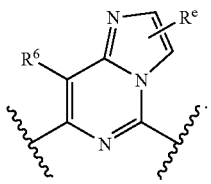

In another embodiment, in conjunction with the above and below embodiments, $R^2$ is a saturated, partially saturated or unsaturated 5-, 6- or 7-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$^aC_{2-6}$alkylN$R^aR^a$ and —N$R^aC_{2-6}$alkylO$R^a$.

In another embodiment, in conjunction with the above and below embodiments, $R^2$ is a saturated, partially saturated or unsaturated 5-, 6- or 7-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups, and wherein the ring is substituted by 1, 2 or 3 substituents independently selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with the above and below embodiments, $R^2$ is a saturated, partially saturated or unsaturated 6-, 7-, 8-, 9-, 10- or 11-member bicyclic ring containing 1, 2, 3 or 4 atoms selected from N, O and S, so long as the combination of O and S atoms is not greater than 2, wherein the carbon atoms of the ring are substituted by 0, 1 or 2 oxo groups, and wherein the ring is substituted by 0, 1 or 2 substituents independently selected from $C_{1-8}$alkyl, $C_{1-4}$haloalkyl, halo, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with the above and below embodiments, R$^2$ is a saturated, partially saturated or unsaturated 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups, and wherein the ring is substituted by 1, 2 or 3 substituents independently selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with the above and below embodiments, R$^2$ is a ring selected from phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofriryl, pyrrolyl, pyazolyl, imidazolyl, triazolyl, thiazolyl, oxazolyl, isoxazolyl, isothiazolyl, indolyl, isoindolyl, indolinyl, benzodioxyl, benzofuranyl, dihydrobenzofliranyl, cyclopropyl, cyclobutyl, cyclopentyl, cyclohexyl, cycloheptyl, benzothiophenyl and benzimidazolyl, wherein the carbon atoms of the ring are substituted by 0, 1 or 2 oxo groups, and wherein the ring is substituted by 0, 1, 2 or 3 substituents independently selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with the above and below embodiments, R$^2$ is a ring selected from phenyl, dihydroindenyl, naphthyl, tetrahydronaphthalenyl, pyridyl, pyrimidinyl, pyrrolidinyl, piperidinyl, piperazinyl, morpholinyl, thiophenyl, pyranyl, furyl, dihydrofliryl, tetrahydrofuryl, pyazolyl, imidazolyl, triazolyl, thiazolyl, oxazolyl, isoxazolyl, isothiazolyl, indolyl, isoindolyl, indolinyl, benzodioxyl, benzofuranyl, dihydrobenzofuranyl, cyclopropyl, cyclobutyl, cyclopentyl, cyclohexyl, cycloheptyl, benzothiophenyl and benzimidazolyl, wherein the carbon atoms of the ring are substituted by 0, 1 or 2 oxo groups, and wherein the ring is substituted by 0, 1, 2 or 3 substituents independently selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with the above and below embodiments, R$^3$ is H.

In another embodiment, in conjunction with the above and below embodiments, in at least one occurance, R$^3$ is C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$.

In another embodiment, in conjunction with the above and below embodiments, R$^3$ is independently at each instance H, C$_{1-8}$alkyl, C$_{1-4}$haloalkyl or halo.

In another embodiment, in conjunction with the above and below embodiments, R$^3$ is H, C$_{1-8}$alkyl, C$_{1-4}$haloalkyl, halo, cyano, nitro, —OR$^a$, —OC$_{2-6}$alkylNR$^a$R$^a$, —OC$_{2-6}$alkylOR$^a$, —SR$^a$, —NR$^a$R$^a$, —NR$^a$C$_{2-6}$alkylNR$^a$R$^a$ or —NR$^a$C$_{2-6}$alkylOR$^a$.

In another embodiment, in conjunction with the above and below embodiments, R$^3$ is H, C$_{1-8}$alkyl, C$_{1-4}$haloalkyl, halo, —OR$^a$, —SR$^a$ or —NR$^a$R$^a$.

In another embodiment, in conjunction with the above and below embodiments, R$^3$ is H, C$_{1-8}$alkyl, C$_{1-4}$haloalkyl, halo or —OR$^a$.

In another embodiment, in conjunction with the above and below embodiments, R$^3$ is H, —CH$_3$, —CH$_2$CH$_3$ or —OR$^a$.

In another embodiment, in conjunction with the above and below embodiments, R$^4$ is C$_{1-8}$alkyl, C$_{1-4}$haloalkyl or halo.

In another embodiment, in conjunction with the above and below embodiments, R$^4$ is cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, or —NR$^a$C$_{2-6}$alkylOR$^a$.

In another embodiment, in conjunction with the above and below embodiments, R$^4$ is C$_{1-8}$alkyl, C$_{1-4}$haloalkyl, halo, cyano, nitro, —C(=O)R$^b$, —OR$^a$, —OC$_{2-6}$alkylNR$^a$R$^a$, —OC$_{2-6}$alkylOR$^a$, —SR$^a$, —NR$^a$R$^a$, —NR$^a$C$_{2-6}$alkylNR$^a$R$^a$ or —NR$^a$C$_{26}$alkylOR$^a$.

In another embodiment, in conjunction with the above and below embodiments, R$^4$ is C$_{1-8}$alkyl, C$_{1-4}$haloalkyl, halo, cyano, nitro, —OR$^a$, —SR$^a$, —NR$^a$R$^a$, —NR$^a$C$_{2-6}$alkylNR$^a$R$^a$ or —NR$^a$C$_{2-6}$alkylOR$^a$.

In another embodiment, in conjunction with the above and below embodiments, R$^4$ is H or C$_{1-8}$alkyl.

In another embodiment, in conjunction with the above and below embodiments, R$^4$ is H or is absent.

In another embodiment, in conjunction with the above and below embodiments, R$^5$ is H.

In another embodiment, in conjunction with the above and below embodiments, $R^5$ is $C_{1-6}$alkyl substituted by 0, 1, 2 or 3 substituents independently selected from $R^d$ and additionally substituted by 0 or 1 substituents selected from $R^f$.

In another embodiment, in conjunction with the above and below embodiments, $R^5$ is $C_{1-6}$alkyl substituted by 1, 2 or 3 substituents independently selected from Rd and additionally substituted by 0 or 1 substituents selected from $R^f$.

In another embodiment, in conjunction with the above and below embodiments, $R^5$ is $C_{1-6}$alkyl substituted by 0, 1, 2 or 3 substituents independently selected from $R^d$ and additionally substituted by 1 substituent selected from $R^f$.

In another embodiment, in conjunction with the above and below embodiments, $R^5$ is H, —$CH_3$, —$CH_2CH_3$, —C(=O)CH(OH)$CH_3$, —$SO_2CH_3$, —C(=O)CH($CH_3$)OC(=O)$CH_3$, -propyl, -isopropyl, —$CH_2CHF_2$, -n-butyl, -t-butyl, -isobutyl, —$(CH_2)_2$COOH, —$(CH_2)_2$COO$CH_3$, —$(CH2)_2$OPh, —CH($CH_3$)ethyl, —CH(CH3)$CF_3$, -cyclopentyl or —$OR^a$.

In another embodiment, in conjunction with the above and below embodiments, $R^5$ is H.

In another embodiment, in conjunction with the above and below embodiments, $R^6$ is H.

In another embodiment, in conjunction with the above and below embodiments, R6 is $R^f$, $R^d$, or a $C_{1-6}$alkyl substituted by 1, 2 or 3 substituents independently selected from $R^d$ and additionally substituted by 0 or 1 substituents selected from $R^f$.

In another embodiment, in conjunction with the above and below embodiments, $R^6$ is H, —$CH_3$ or —$CH_2CH_3$.

In another embodiment, in conjunction with the above and below embodiments, $R^6$ is H or $C_{1-6}$alkyl.

In another embodiment, in conjunction with the above and below embodiments, $R^6$ is $R^c$, $R^d$, or a $C_{1-6}$alkyl substituted by 1, 2 or 3 substituents independently selected from $R^d$ and additionally substituted by 0 or 1 substituents selected from $R^f$.

In another embodiment, in conjunction with the above and below embodiments, R6 is H.

In another embodiment, in conjunction with the above and below embodiments, $R^6$ is independently, at each instance, $C_{1-6}$alkyl.

In accordance with another embodiment of the present invention, there are provided compounds of formula II:

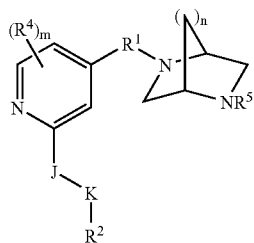

or a pharmaceutically acceptable salt thereof, wherein
J is NH, N($P^b$), O or S;
K is —C($R_3R_3$)m, —C(=O), —C(=O)O—, —C(=O)N($R^a$)—, —C(=N$R^a$)N($R^a$)—O—, —OC(=O)—, —OC(=O)N($R^a$)—, —O$C_{2-6}$alkylN($R^a$), —O$C_{2-6}$alkylO—, —S—, —S(=O)—, —S(=O)$_2$—, —S(=O)$_2$N($R^a$)—, —N($R^a$)—, —N($R^a$)C(=O)—, —N($R^a$)C(=O)O—, —N($R^a$)C(=O)N($R^a$)—, —N($R^a$)C(=N$R^a$)N($R^a$)—, —N($R^a$)S(=O)$_2$—, —N($R^a$)S(=O)$_2$N($R^a$)— or —N($R^a$)$C_{2-6}$alkylN($R^a$);

$R^1$ is selected from

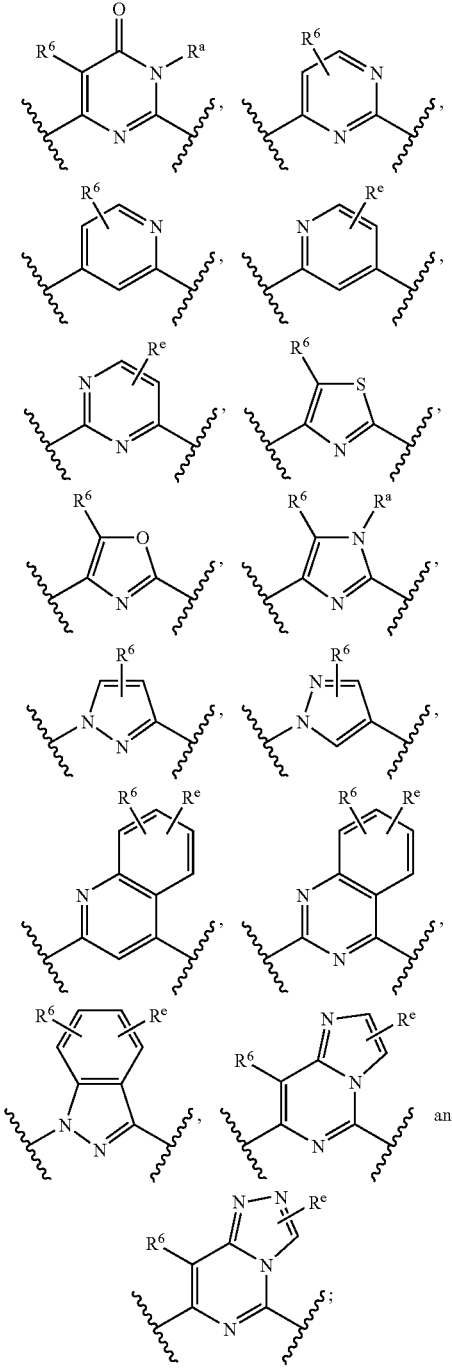

$R^2$ is a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N (R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)R$^b$, —S(=O)$_2$N(R$^a$)C(=O)NR$^a$R$^a$, —NR$^a$R$^a$, —N(R$^a$)C(=O) R$^b$, —N(R$^a$)C(=O)OR$^b$, —N(R$^a$)C(=O)NR$^a$R$^a$, —N(R$^a$)C (=NR$^a$)NR$^a$R$^a$, —N(R$^a$)S(=O)$_2$R$^b$, —N(R$^a$)S(=O)$_2$ NR$^a$R$^a$, —NR$^a$C$_{2-6}$alkylNR$^a$R$^a$ and —NR$^a$C$_{2-6}$alkylOR$^a$;

R$^3$ is independently at each instance H, C$_{1-8}$alkyl, C$_{1-8}$alkylOR$^a$, C$_{1-4}$haloalkyl, C$_{1-4}$haloalkylOR$^a$, halo, cyano, nitro, oxo, —C(=O)R$^b$, —C(=O)OR$^b$, —C(=O) NR$^a$R$^a$, —C(=NR$^a$)NR$^a$R$^a$, —OR$^a$, —OC(=O)R$^b$, —OC (=O)NR$^a$R$^a$, —OC(=O)N(R$^a$)S(=O)$_2$R$^b$, —OC$_{2-6}$alkyl-NR$^a$R$^a$, —OC$_{2-6}$alkylOR$^a$, —SR$^a$, —S(=O)R$^b$, —S(=O)$_2$ R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O) NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$) S(=O)$_2$R$^b$, —N(R$^a$)S(=O)$_2$NR$^a$R$^a$, —NR$^a$C$_{2-6}$alkylN-R$^a$R$^a$ or —NR$^a$C$_{2-6}$alkylOR$^a$;

R$^4$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O) R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O) R$^b$, —S(=O)$_2$R$^b$, —S(=O)$_2$NR$^a$R$^a$, —S(=O)$_2$N(R$^a$)C (=O)R$^b$, —S(=O)$_2$N(R$^a$)C(=O)OR$^b$, —S(=O)$_2$N(R$^a$)C (=O)NR$^a$R$^a$, —NR$^a$R$^a$, —N(R$^a$)C(=O)R$^b$, —N(R$^a$)C (=O)OR$^b$, —N(R$^a$)C(=O)NR$^a$R$^a$, —N(R$^a$)C(=NR$^a$) NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^5$ is H, C(=O)R$^b$, S(O)$_p$R$^b$, C(=O)R$^c$, S(O)$_p$R$^c$, or C$_{1-6}$alkyl substituted by 0, 1, 2 or 3 substituents independently selected from R$^d$ and additionally substituted by 0 or 1 substituents selected from R$^f$;

R6 is H, R$^c$, R$^d$, or a C$_{1-6}$alkyl substituted by 1, 2 or 3 substituents independently selected from R$^d$ and additionally substituted by 0 or 1 substituents selected from R$^f$;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, and —N(C$_{1-4}$alkyl)C$_{1-4}$alkyl;

R$^c$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

R$^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O) R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O) R$^b$, —S(=O)$_2$R$^b$, —S(=O)$_2$NR$^a$R$^a$, —S(=O)$_2$N(R$^a$)C (=O)R$^b$, —S(=O)$_2$N(R$^a$)C(=O)OR$^b$, —S(=O)$_2$N(R$^a$)C (=O)NR$^a$R$^a$, —NR$^a$R$^a$, —N(R$^a$)C(=O)R$^b$, —N(R$^a$)C (=O)OR$^b$, —N(R$^a$)C(=O)NR$^a$R$^a$, —N(R$^a$)C(=NR$^a$) NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^e$ is independently at each instance R$^d$ or H;

R$^f$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O) NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N (R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$) S(=O)$_2$R$^b$, —N(R$^a$)S(=O)$_2$NR$^a$R$^a$, —NR$^a$C$_{2-6}$alkylN-R$^a$R$^a$ and —NR$^a$C$_{2-6}$alkylOR$^a$;

m is independently at each instance 0, 1, 2 or 3;

n is 1; and p is 0, 1 or 2.

In another embodiment, in conjunction with the above and below embodiments, J is NH.

In another embodiment, in conjunction with the above and below embodiments, J is NCH$_3$.

In another embodiment, in conjunction with the above and below embodiments, K is —C(R$_3$R$_3$)$_m$—, —C(=O)—, —C(=O) O—, —C(=O)N(R$^a$)—, —C(=NR$^a$)N(R$^a$)—, —S(=O)—, —S(=O)$_2$—, —S(=O)$_2$N(R$^a$)— or —N(R$^a$)—.

In another embodiment, in conjunction with the above and below embodiments, K is —C(R$_3$R$_3$)$_m$—, —C(=O)—, —C(=O) N(R$^a$)—, —S(=O)—, —S(=O)$_2$—or —S(=O)$_2$N(R$^a$)—.

In another embodiment, in conjunction with the above and below embodiments, R$^1$ is selected from

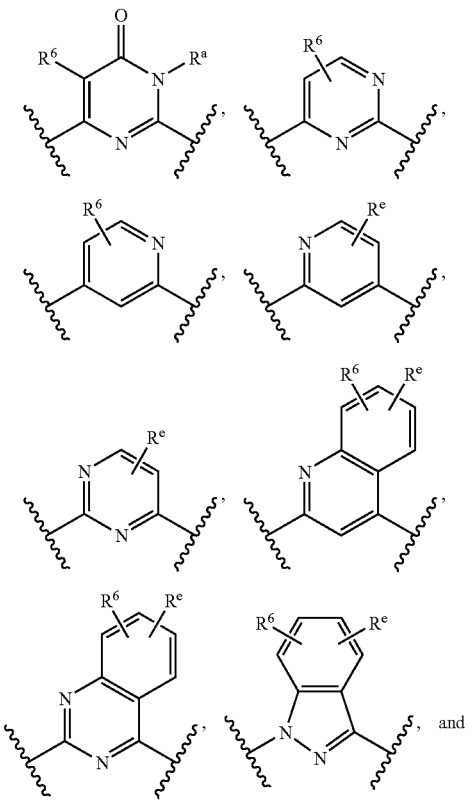

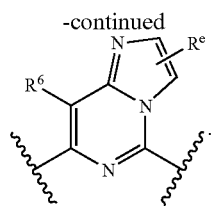

In another embodiment, in conjunction with the above and below embodiments, $R^1$ is selected from

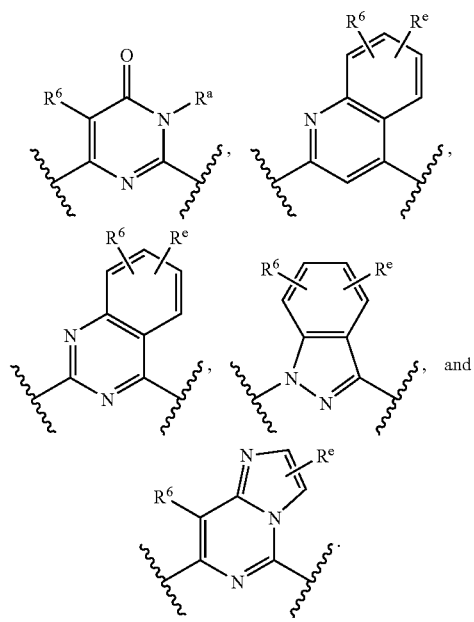

In another embodiment, in conjunction with the above and below embodiments, $R^2$ is a ring selected from phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzodioxyl, benzofuranyl, dihydrobenzofuranyl, cyclopropyl, cyclobutyl, cyclopentyl, cyclohexyl, cycloheptyl, benzothiophenyl and benzimidazolyl, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)$R^b$, —C(=O)O$R^b$, C(=O)N$R^aR^a$, C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylOR$^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —NR$^a$C$_{2-6}$alkylN$R^aR^a$ and —NR$^a$C$_{2-6}$alkylOR$^a$.

In another embodiment, in conjunction with the above and below embodiments, $R^2$ is a ring selected from phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzodioxyl, benzofuranyl, dihydrobenzofuranyl, cyclopropyl, cyclobutyl, cyclopentyl, cyclohexyl, cycloheptyl, benzothiophenyl and benzimidazolyl, wherein the carbon atoms of the ring are substituted by 0, 1 or 2 oxo groups, and wherein the ring is substituted by 1, 2 or 3 substituents independently selected from $C_{1-8}$alkyl, $C_{1-4}$haloalkyl, halo, cyano, nitro, —C(=O)$R^b$, —C(=O)O$^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylOR$^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)OR$^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —NR$^a$C$_{2-6}$alkylN$R^aR^a$ and —NR$^a$C$_{2-6}$alkylOR$^a$.

In another embodiment, in conjunction with the above and below embodiments, $R^3$ is H, $C_{1-6}$alkyl, $C_{1-4}$haloalkyl, halo or —O$R^a$.

In another embodiment, in conjunction with the above and below embodiments, $R^3$ is independently at each instance H, $C_{1-8}$alkyl, $C_{1-4}$haloalkyl, halo, —O$R^a$, —S$R^a$ or —N$R^aR^a$.

In another embodiment, in conjunction with the above and below embodiments, $R^4$ is H or $C_{1-6}$alkyl.

In another embodiment, in conjunction with the above and below embodiments, $R^4$ is H.

In another embodiment, in conjunction with the above and below embodiments, $R^4$ is $C_{1-8}$alkyl, $C_{1-4}$haloalkyl, halo, cyano, nitro, —O$R^a$, —S$R^a$, —N$R^aR^a$, —NR$^a$C$_{2-6}$alkylN$R^aR^a$ or —NR$^a$C$_{2-6}$alkylOR$^a$.

In another embodiment, in conjunction with the above and below embodiments, $R^5$ is H, C(=O)$R^b$, S(O)$_pR^b$, C(=O)$R^c$, S(O)$_pR^c$, or $C_{1-6}$alkyl substituted by 0, 1, 2 or 3 substituents independently selected from $R^d$ and additionally substituted by 0 or 1 substituents selected from $R^f$.

In another embodiment, in conjunction with the above and below embodiments, $R^5$ is H.

In another embodiment, in conjunction with the above and below embodiments, $R^6$ is $C_{1-6}$alkyl.

In another embodiment, in conjunction with the above and below embodiments, $R^6$ is H.

In accordance with another embodiment, the invention provides compounds of Formula II wherein J is NH or NCH$_3$;

K is —C($R_3R_3$)$_m$, —C(=O), —C(=O)O—, —C(=O)N($R^a$)—, —C(=N$R^a$)N($R^a$)—, —S(=O)—, —S(=O)$_2$—, —S(=O)$_2$N($R^a$)— or —N($R^a$)—;

$R^1$ is selected from

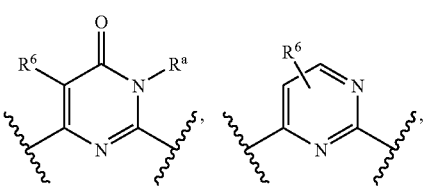

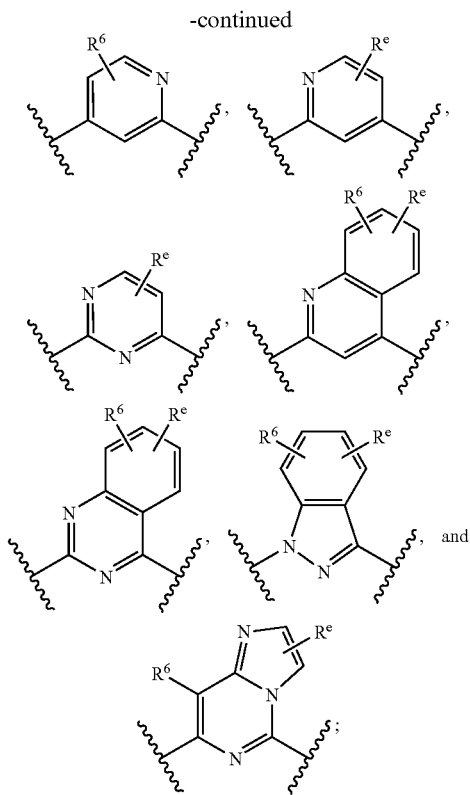

R² is a ring selected from phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyrazolyl, imidazolyl, triazolyl, thiazolyl, oxazolyl, isoxazolyl, isothiazolyl, indolyl, isoindolyl, indolinyl, benzodioxyl, benzofuranyl, dihydrobenzofuranyl, cyclopropyl, cyclobutyl, cyclopentyl, cyclohexyl, cycloheptyl, benzothiophenyl and benzimidazolyl, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R³ is independently at each instance H, $C_{1-8}$alkyl, $C_{1-4}$haloalkyl, halo, —OR$^a$, —SR$^a$ or —NR$^a$R$^a$;

R⁴ is independently at each instance $C_{1-8}$alkyl, $C_{1-4}$haloalkyl, halo, cyano, nitro, —OR$^a$, —SR$^a$, —NR$^a$R$^a$, —NR$^a$C$_{2-6}$alkylNR$^a$R$^a$ or —NR$^a$C$_{2-6}$alkylOR$^a$;

R⁵ is H, C(=O)R$^b$, S(O)$_p$R$^b$, C(=O)R$^c$, S(O)$_p$R$^c$, or $C_{1-6}$alkyl substituted by 0, 1, 2 or 3 substituents independently selected from R$^d$ and additionally substituted by 0 or 1 substituents selected from R$^f$;

R6 is H, R$^c$, R$^d$, or a $C_{1-6}$alkyl substituted by 1, 2 or 3 substituents independently selected from R$^d$ and additionally substituted by 0 or 1 substituents selected from R$^f$, R$^a$ is independently, at each instance, H or R$^b$;

R$^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —OC$_{1-4}$alkyl, —NH$_2$, —NHC$_{1-4}$alkyl and —N(C$_{1-4}$alkyl)C$_4$alkyl;

R$^c$ is independently, at each instance, phenyl, naphthyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyrazolyl, imidazolyl, triazolyl, thiazolyl, oxazolyl, isoxazolyl, isothiazolyl, indolyl, isoindolyl, indolinyl, benzofuranyl, dihydrobenzofuranyl, cyclopropyl, cyclobutyl, cyclopentyl, cyclohexyl, cycloheptyl, benzothiophenyl or benzimidazolyl, wherein the carbon atoms of the ring are substituted by 0, 1 or 2 oxo groups;

R$^d$ is independently at each instance $C_{1-8}$alkyl, $C_{1-4}$haloalkyl, halo, cyano, nitro, —C(=O)R$^b$, —C(=O)OR$^b$, —C(=O)NR$^a$R$^a$, C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C2-6alkylOR$^a$;

R$^e$ is independently at each instance R$^d$ or H;

R$^f$ is independently at each instance phenyl, naphthyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyrazolyl, imidazolyl, triazolyl, thiazolyl, oxazolyl, isoxazolyl, isothiazolyl, indolyl, isoindolyl, indolinyl, benzofuranyl, dihydrobenzofuranyl, cyclopropyl, cyclobutyl, cyclopentyl, cyclohexyl, cycloheptyl, benzothiophenyl or benzimidazolyl, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)R$^b$, —C(=O)NR$^a$R$^a$, —OR$^a$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

m is independently at each instance 0, 1, 2 or 3;

n is 1; and p is 0, 1 or 2.

In accordance with another embodiment, the invention provides compounds of Formula II wherein J is NH or NCH$_3$;

K is —C(R$_3$R$_3$)$_m$—, —C(=O)—, —C(=O)N(R$^a$)—, —S(=O)—, —S(=O)$_2$— or —S(=O)$_2$N(R$^a$)—;

$R^1$ is selected from

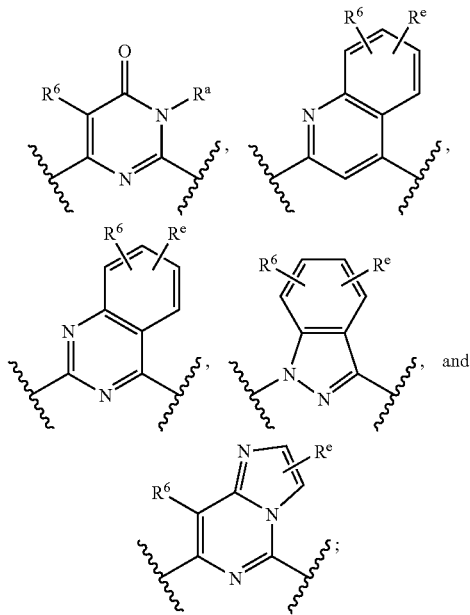

$R^2$ is a ring selected from phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzodioxyl, benzofuranyl, dihydrobenzofuranyl, cyclopropyl, cyclobutyl, cyclopentyl, cyclohexyl, cycloheptyl, benzothiophenyl and benzimidazolyl, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$ and —N$R^a C_{2-6}$alkylO$R^a$;

$R^3$ is independently at each instance H, $C_{1-6}$alkyl, $C_{1-4}$haloalkyl, halo or —O$R^a$;

$R^4$ is H or $C_{1-6}$alkyl;

$R^5$ is H, C(=O)$R^b$, S(O)$_p R^b$, C(=O)$R^c$, S(O)$_p R^c$, or $C_{1-6}$alkyl substituted by 0, 1, 2 or 3 substituents independently selected from $R^d$ and additionally substituted by 0 or 1 substituents selected from $R^f$;

$R^6$ is H or $C_{1-6}$alkyl;

$R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl and —N($C_{1-4}$alkyl)$C_{1-4}$alkyl;

$R^c$ is independently, at each instance, phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzodioxyl, benzofuranyl, dihydrobenzofuranyl, cyclopropyl, cyclobutyl, cyclopentyl, cyclohexyl, cycloheptyl, benzothiophenyl or benzimidazolyl, wherein the carbon atoms of the ring are substituted by 0, 1 or 2 oxo groups;

$R^d$ is independently at each instance $C_{1-8}$alkyl, $C_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$ or —N$R^a C_{2-6}$alkylO$R^a$;

$R^e$ is independently, at each instance, H, Cl, F, Br, I, $CH_3$, $NO_2$, $NHSO_2CH_3$, OH, $CF_3$ or N-Acetyl;

$R^f$ is independently, at each instance, phenyl, pyridyl, pyrimidinyl, pyrrolidinyl, piperidinyl, piperazinyl, triazinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzofuranyl, dihydrobenzofuranyl, cyclopropyl, cyclobutyl, cyclopentyl, cyclohexyl, cycloheptyl, benzothiophenyl or benzimidazolyl, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)N$R^a R^a$, —O$R^a$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —N$R^a R^a$, —N($R^a$)C(=O)$R^b$, —N($R^a$)C(=O)N$R^a R^a$, —N($R^a$)S(=O)$_2 R^b$, —N($R^a$)S(=O)$_2$N$R^a R^a$, —N$R^a C_{2-6}$alkylN$R^a R^a$ and —N$R^a C2-6$alkylO$R^a$;

m is independently at each instance 0, 1, 2 or 3;

n is 1; and p is 0, 1 or 2.

In accordance with another embodiment, the invention provides specific compounds of Formula I and/or II, which are described in the examples herein.

Another aspect of the invention relates to a pharmaceutical composition comprising at least one compound according to any one of the above embodiments and a pharmaceutically acceptable carrier.

Another aspect of the invention relates to a method of treatment of arthritis, rheumatoid arthritis, psoriatic arthritis or osteoarthritis, organ transplant, acute transplant or heterograft and homograft rejection, ischemic and reperfusion injury, transplantation tolerance induction, multiple sclerosis, inflammatory bowel disease, ulcerative colitis, Crohn's disease, lupus, graft vs. host diseases, T-cell mediated hypersensitivity diseases, contact hypersensitivity, delayed-type hypersensitivity, gluten-Sensitive enteropathy, Type 1 diabetes, psoriasis, contact dermatitis, Hashimoto's thyroiditis, Sjogren's syndrome, autoimmune hyperthyroidism, Graves' Disease, Addison's disease, autoimmune polyglandular disease, autoimmune alopecia, pernicious anemia, vitiligo, autoimmune hypopituatarism, Guillain-Barre syndrome, autoimmune diseases, glomerulonephritis, serum sickness, uticaria, respiratory allergies, asthma, hayfever, allergic rhinitis, skin allergies, scleracielma, mycosis flugoides, acute inflammatory responses, acute respiratory distress syndrome, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea; type II diabes; insulin resistance; diabetic retinopathy; diabetic macular edema; diabetic neuropathy; and cardiovascular disease in a mammal comprising administering an effective amount of a compound according to any one of the above embodiments to a mammal in need thereof.

Another aspect of the invention relates to a of method treating cancers where PKC theta or other PKC-family kinases are activated, overexpressed or facilitate tumor growth or survival or resistance to chemotherapeutic drugs of tumor cells, T cell leukemia, thymoma, T and B cell lymphoma, colon carcinoma, breast carcinoma and lung carcinoma comprising administering an effective amount of a compound according to any one of the above embodiments to a mammal in need thereof.

Another aspect of the invention relates to a method of treating a disease or disorder mediated by PKC-theta, the method comprising administering an effective amount of a compound according to any of the above embodiments within Formulas I or II, to a mammal.

Another aspect of the invention relates to a method of treating a disease or disorder associated with the activation of T cells, the method comprising administering to the mammal an effective amount of a compound according to any of the above embodiments within Formulas I or II, to a mammal.

Another aspect of the invention relates to the manufacture of a medicament comprising a compound according to any one of the above embodiments.

Another aspect of the invention relates to the manufacture of a medicament for the treatment of arthritis, rheumatoid arthritis, psoriatic arthritis or osteoarthritis, organ transplant, acute transplant or heterograft and homograft rejection, ischemic and reperfusion injury, transplantation tolerance induction, multiple sclerosis, inflammatory bowel disease, ulcerative colitis, Crohn's disease, lupus, graft vs. host diseases, T-cell mediated hypersensitivity diseases, contact hypersensitivity, delayed-type hypersensitivity, gluten-Sensitive enteropathy, Type 1 diabetes, psoriasis, contact dermatitis, Hashimoto's thyroiditis, Sjogren's syndrome, autoimmune hyperthyroidism, Graves' Disease, Addison's disease, autoimmune polyglandular disease, autoimmune alopecia, pernicious anemia, vitiligo, autoimmune hypopituatarism, Guillain-Barre syndrome, autoimmune diseases, glomerulonephritis, serum sickness, uticaria, respiratory allergies, asthma, hayfever, allergic rhinitis, skin allergies, scleracielma, mycosis flngoides, acute inflammatory responses, acute respiratory distress syndrome, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea, type II diabes; insulin resistance; diabetic retinopathy; diabetic macular edema; diabetic neuropathy; and cardiovascular disease in a mammal comprising administering an effective amount of a compound according to any one of the above embodiments.

Another aspect of the invention relates to the manufacture of a medicament for the treatment of cancers where PKC theta or other PKC-family kinases are activated, overexpressed or facilitate tumor growth, survival of tumor cells, resistance to chemotherapeutic agents or radiation, T cell leukemia, thymoma, T and B cell lymphoma, colon carcinoma, breast carcinoma, and lung carcinoma in a mammal comprising administering an effective amount of a compound according to any one of the above embodiments.

The compounds of this invention may have in general several asymmetric centers and are typically depicted in the form of racemic mixtures. This invention is intended to encompass racemic mixtures, partially racemic mixtures and separate enantiomers and diastereomers.

The specification and claims contain listing of species using the language "selected from . . . and . . ." and "is . . . or . . ." (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Unless otherwise specified, the following definitions apply to terms found in the specification and claims:

"Aryl" means a phenyl or naphthyl radical, wherein the phenyl may be fused with a $C_{3-4}$cycloalkyl bridge.

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

"$C_{\alpha-\beta}$alkyl" means an alkyl group comprising from $\alpha$ to $\beta$ carbon atoms in a branched, cyclical or linear relationship or any combination of the three. The alkyl groups described in this section may also contain double or triple bonds. Examples of $C_{1-8}$alkyl include, but are not limited to the following:

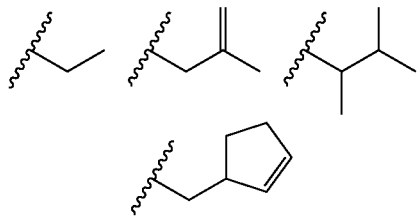

"Halogen" and "halo" mean a halogen atoms selected from F, Cl, Br and I.

"$C_{\alpha-\beta}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

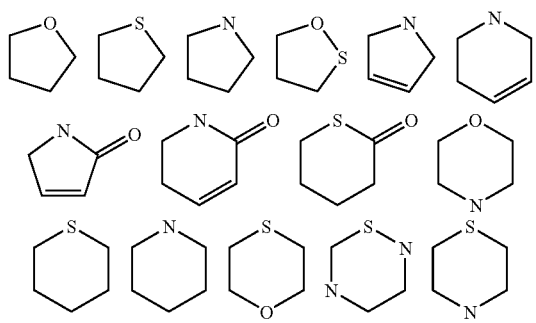

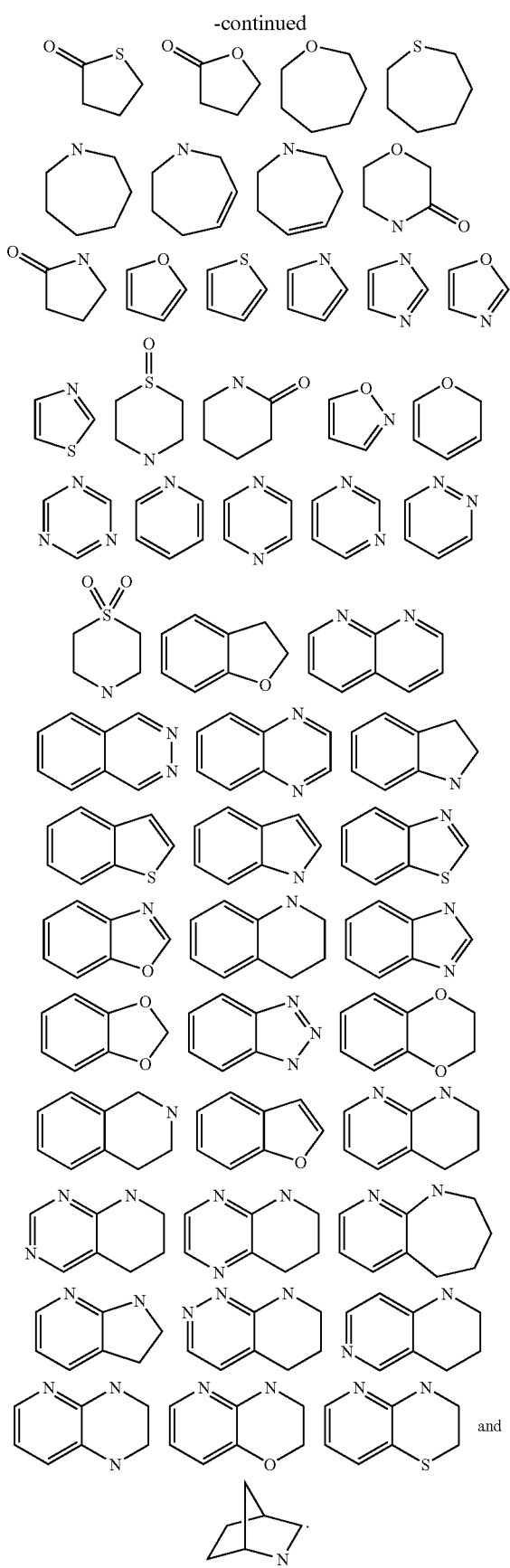

"Oxo" means an oxygen atom covalently bound to a carbon atom by a double bond, also commonly referred to as a carbonyl group. It is readily appreciated that given an aromatic ring (fully unsaturated), the ring cannot be substituted with an "oxo" group, i.e., there cannot be any carbonyl groups on the ring. However, where the ring is partially or fully saturated, it may contain a carbonyl group. For example, a pyrimidin one ring is a partially saturated 6-membered heteroaryl ring wherein one of the carbon atoms in the ring is a ketone.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Treatment" of diseases and disorders herein is intended to include the administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-Substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups are commonly used to protect amines, as well as hydroxyl and mercapto groups, as appreciated by those of ordinary skill in the art. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-Silylamino groups. Silylation of aminoalcohol compounds can lead to a N,N,O-tri-Silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions, which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O,S, NR), and the like, which are illustrated in the following examples:

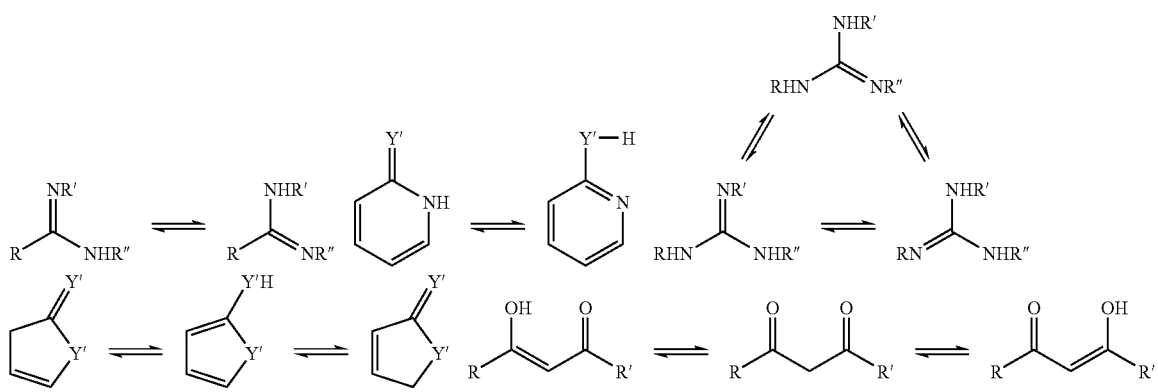

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives, which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981 discloses Mannich-base hydroxamic acid prodrugs, their preparation and use.

"Cytokine" means a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Acronyms

Acronyms utilized throughout the specification shall have the following meaning:
BINAP: 2,2'-bis-diphenylphosphanyl-[1,1']binaphthalenyl
DCM: dichloromethane
DIEA: N,N-diisopropylethylamine
DME: 1,2-dimethoxyethane
DMF: dimethylformamide
LHMS: lithium bis(trimethylsilyl)amide
NMP: N-methyl-2-pyrrolidone
rac-BINAP: racemic 2,2'-bis-diphenylphosphanyl-[1,1']binaphthalenyl
RBF: round bottom flask
TBAF: tetra-butyl ammonium fluoride
TBDPSCl: tert-butyldiphenylsilyl chloride
THF: tetrahydrofuran
TMS: trimethyl silane
TMSCH$_2$CN: trimethylsilanylacetonitrile
TsCl: tosyl chloride Synthesis of 5-Chloro-7-(2-chloro-pyridin-4-yl)-imidazo[1,2-c]pyrimidine

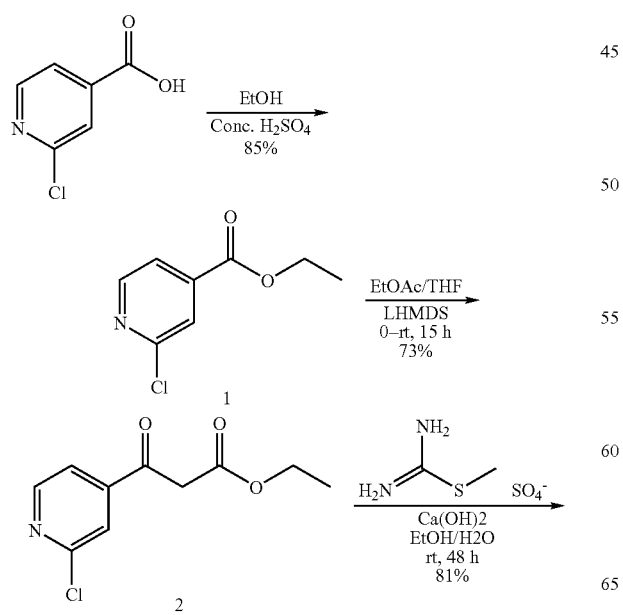

-continued

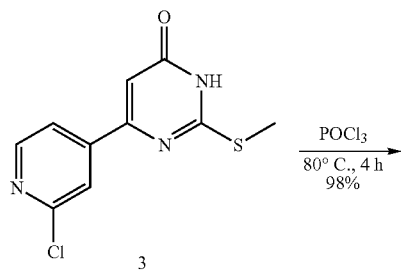

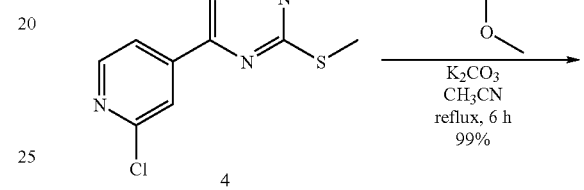

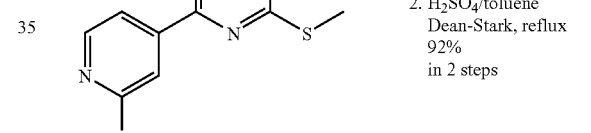

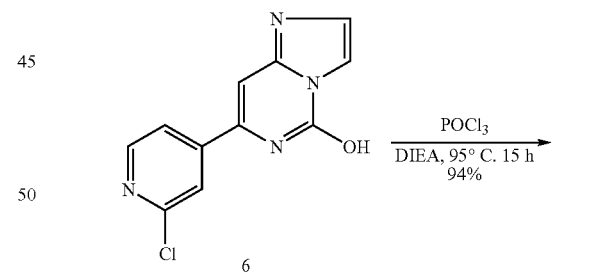

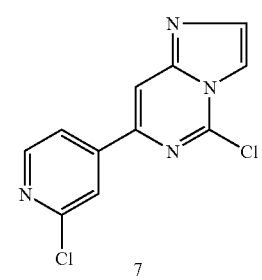

EXAMPLE 1

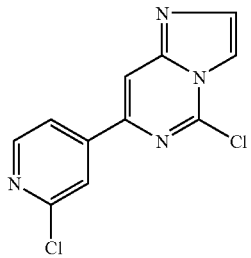

Step A: 2-Chloro-isonicotinic acid ethyl ester (1).

The mixture of 2-chloro-isonicotinic acid (16.8 g, 0.107 mol), 100 mL absolute ethanol and concentrate H₂SO₄ (3.28 mL, 0.118 mol) was refluxed under nitrogen for 15 h. After all starting material converted, the mixture was cool down to rt, and vacuumed down all ethanol. The resulted mixture was diluted with 250 mL ethyl acetate, washed with sat. NaHCO₃, dried over anhydrous Na₂SO₄. Purified by a short column, the title compound was obtained as a pale yellow liquid. MS (ES+): 186 (M+H)⁺.

Step B: 3-(2-Chloro-pyridin-4-yl)-3-oxo-propionic acid ethyl ester (2)

The mixture of 15 g 2-chloro-isonicotinic acid ethyl ester (1)(81.4 mmol), and 8.75 mL ethyl acetate (88 mmol) in 200 mL anhydrous THF was stirred at 0° C. under nitrogen. The mixture was treated with 100 mL LHMS (1.0 M in THF) in 30 min. The resulted mixture was stirred at 0° C.—rt for 15 h, then quenched with 200 mL sat. NH₄Cl at 0° C. and adjusted pH 6-7. The water layer was extracted with ethyl acetate 3×50 mL. The combined organic was dried over anhydrous Na₂SO₄, and purified by column. The titled compound was obtained as a pale yellow solid.

MS (ES+): 228 (M+H)⁺.

Step C: 6-(2-Chloro-pyridin-4-yl)-2-methylsulfanyl-3H-pyrimidin-4-one (3)

The mixture of 11.2 g 3-(2-chloro-pyridin-4-yl)-3-oxo-propionic acid ethyl ester (2) (49.4 mmol) and 13.74 g 2-methyl-isothiourea sulfate in 182 mL ethanol and 50 mL water was stirred at 0° C. under nitrogen. The mixture was treated with 4.39 g Ca(OH)₂, and stirred 0° C.—rt for 15 h. The mixture was quenched with 200 mL water and adjusted pH 6-7, then filtrated and washed with 200 mL water, and 100 mL hexane. The filtrated cake was dissolved in 1.5 L 10% methanol/DCM and filtrated again. The organic was dried over Na₂SO₄, concentrated. The titled compound was obtained as a white solid. MS (ES+):254 (M+H)⁺.

Step D: 4-Chloro-6-(2-chloro-pyridin-4-yl)-2-methylsulfanyl-pyrimidine (4)

The mixture of 8.6 g 6-(2-chloro-pyridin-4-yl)-2-methylsulfanyl-3H-pyrimidin-4-one (3)(34 mmol) in 100 mL POCl₃ was heated up to 80° C. and stirred under nitrogen for 4 h. TLC showed all starting material was converted. The mixture was cooled down to rt and vacuumed down all POCl₃. The black cake was dissolved in 200 mL DCM, washed with sat NaHCO₃ carefully, dried over anhydrous Na₂SO₄. The crude product was purified by column and obtained the titled compound as white solid. MS (ES+):272 (M+H)⁺.

Step E: [6-(2-Chloro-pyridin-4-yl)-2methylsulfanyl-pyrimidin-4-yl]-(2,2-dimethoxy-ethyl)-amine (5)

To a 250 mL (RBF) was added 5.95 g (21.96mmol) 4-chloro-6-(2-chloro-pyridin-4-yl)-2-methylsulfanyl-pyrimidine (4), 100 mL CH₃CN and 20 mL DCM. The mixture was stirred at rt under nitrogen, and was treated with 3.0 g K₂CO₃ (21.96 mmol) and 4.73 mL (43.9 mmol) aminoacetaldehyde dimethylacetal at rt. The mixture obtained was refluxed under nitrogen for 6 h. TLC and MS showed all starting materials were converted. The mixture was cooled down to rt and quenched with 200 mL water, extracted with DCM 3×100 mL. The combined organic was washed with brine and dried over Na₂SO₄. The crude product was purified by column (run by hexane/ethyl acetate/methanol:1:1:0.05), and obtained the titled compound as a white solid. MS (ES+): 341 (M+H)⁺.

Step F: 7-(2-Chloro-pyridin-4-yl)-imidazo[1,2-c]pyrimidin-5-ol (6)

To a 500 mL RBF was added 7.5 g (21.96 mmol) [6-(2-chloro-pyridin-4-yl)-2-methylsulfanyl-pyrimidin-4-yl]-(2,2-dimethoxy-ethyl)-amine (5) and 100 mL 2N HCl water solution, the mixture was refluxed for 2 h. MS showed all starting materials were converted. The mixture was cooled down to rt, 100 mL toluene and 5 mL concentrate H₂SO₄ was added at rt, and the mixture was refluxed with a Dean-Stark trap for 4 h. The reaction was followed using MS. After all starting materials were consumed, the mixture was cooled down to rt. The toluene layer was decanted, the water layer was diluted with 100 mL water and neutralized with 5N NaOH to pH 7 carefully. A pale yellow solid precipitated out and was filtrated and washed with 50 mL water. The crude product (6) was azotropic dried with toluene 2×50 mL at first, then dried in 50° C. in a vacuum oven for 24 h. The crude product was used directly in next step without further purification. The crude product should be kept very dry for the next step). MS (ES+): 265 (M+H)⁺.

Step G: 5-Chloro-7-(2-chloro-pyridin-4-yl)-imidazo[1,2-c]pyrimidine (7)

To a 250 mL RBF was added 5.5 g (20.3 mmol) 7-(2-chloro-pyridin-4-yl)-imidazo[1,2-c]pyrimidin-5-ol (6) and 100 mL POCl₃, the mixture was treated with 3.55 mL DIEA (20 mmol) at first. The mixture was sonicated to dissolve all starting material. The mixture was warmed up to 95° C. and treated with another 3.55 mL DIEA (20 mmol) slowly. The mixture was stirred at 95 ° C. for 4 h, and all starting materials were converted. TLC and MS was used to follow the reaction. All POCl₃ was vacuumed down. The residue was dissolved in 500 mL DCM, washed with saturated NaHCO₃ and carefully adjusted to pH 8. The organic phase was dried over Na₂SO₄, concentrated and purified by column (run by 4:1 to 1:1:0.05 hexane/ethyl acetate/methanol), and yielded a pale yellow product (7). MS (ES+):265 (M+H)⁺.

EXAMPLE 2

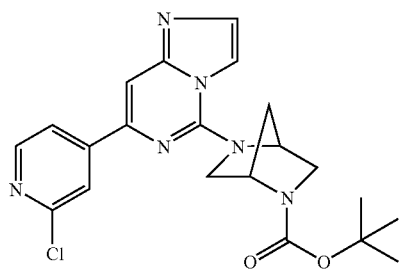

5-[7-(2-Chloro-pyridin-4-yl)-imidazo[1,2-c]pyrimidin-5-yl]-(1S,4S)-2,5-diaza-bicyclo[2.2.1]heptane-2-carboxylic acid tert-butyl ester To a 100 mL RBF was added 5-chloro-7-(2-chloro-pyridin-4-yl)-imidazo[1,2-c]pyrimidine (2.0 g, 7.6 mmol), 20 mL NMP, (S)—N-Boc-2,5-Diaza-bicyclo[2.2.1]heptane (1.6 g, 8.3 mmol), $K_2CO_3$ (1.05 g, 7.6 mmol) and DIEA (1.3 mL, 7.6 mmol). The mixture was stirred at rt under nitrogen for 15 h, and all starting material was converted. The reaction mixture was added to a 100 mL ice water slowly, and a white solid was precipitated out. The precipitate was filtrated and washed with 50 mL water, and further purified by flash chromatograph. The title compound was obtained. MS (ES+):427 (M+H)+.

EXAMPLE 3

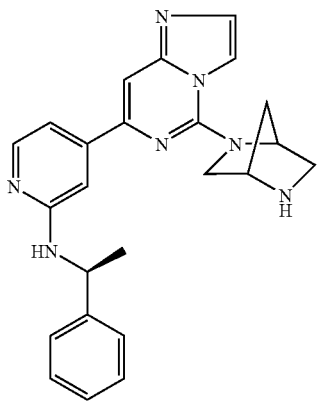

(S)-{4-[5-((1S,4S)-2,5-Diaza-bicyclo[2.2.1]hept-2-yl)-imidazo[1,2-c]pyrimidin-7-yl]-pyridin-2-yl}-(1-phenyl-ethyl)-amine Step A: To a 100 mL RBF, was added 5-[7-(2-chloro-pyridin-4-yl)-imidazo[1,2-c]pyrimidin-5-yl]-2,5-diaza-bicyclo[2.2.1]heptane-2-carboxylic acid tert-butyl ester (0.426 g, 1 mmol), 50 mL toluene and 2.5 mL DMF, and (S)-α-methylbenzylamine (0.14 mL, 1.08 mmol). The mixture was degassed by nitrogen bubbled through for 1 h. After Pd(OAc)2 (23 mg, 0.1 mmol), BINAP (62 mg, 0.1 mmol) and NaOtBu (0.192 g, 2.0 mmol) were added, the mixture was warmed to 90° C. and stirred for 2 h under nitrogen. The mixture was cooled down to rt, diluted with 100 mL DCM, washed with 20 mL sat. $NaHCO_3$, and dried over anhydrous $Na_2SO_4$. After purification by flash chromatography, obtained the 5-{7-[2-(1-phenyl-ethylamino)-pyridin-4-yl]-imidazo[1,2-c]pyrimidin-5-yl}-2,5-diaza-bicyclo[2.2.1]heptane-2-carboxylic acid tert-butyl ester in as a pale yellow solid. MS (ES+): 512 (M+H)+.

Step B: To a 50 mL RBF was added 0.5 g (0.98 mmol) 5-{7-[2-(1-phenyl-ethylamino)pyridin-4-yl]-imidazo[1,2-c]pyrimidin-5-yl}-2,5-diaza-bicyclo[2.2.1]-heptane-2-carboxylic acid tert-butyl ester, 10mL methanol and stirred at rt under nitrogen. The mixture was treated with and 2.5 mL 4N HCl in dioxane and was stirred at rt for 1 h. The mixture was diluted with 100 mL DCM, washed with 20 mL sat. $NaHCO_3$, and dried over anhydrous $Na_2SO_4$. After purification by flash chromatography, obtained the title compound as a pale yellow solid. MS (ES+):412 (M+H)+.

EXAMPLE 4

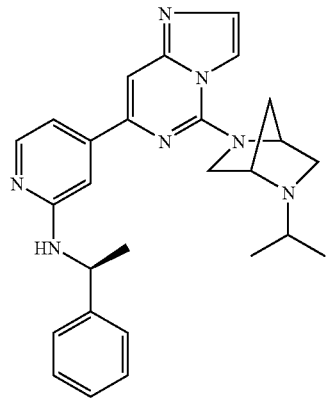

(S)-{4-[5-(5-Isopropyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine The mixture of 100 mg (0.24 mmol) {4-[5-(2,5-diaza-bicyclo[2.2.1]hept-2-yl)-imidazo [1,2-c]pyrimidin-7-yl]-pyridin-2-yl}-(1-phenyl-ethyl)-amine in 5 mL chloroform was treated with 0.2 mL (2.4 mmol) acetone, 45 mg (0.72 mmol) $NaBH_3(CN)$ and 1 mL methanol consequently. The mixture was stirred at rt for 15 h. MS showed all starting materials were converted. The mixture was diluted with 100 mL DCM, washed with 20 mL sat. $NaHCO_3$, dried over anhydrous $Na_2SO_4$. After purification by chromatography, the title compound was obtained as a yellow solid. MS (ES+):454 (M+H)+.

EXAMPLE 5

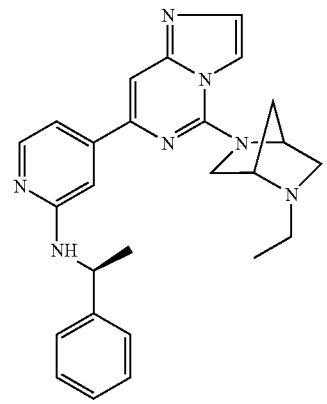

(S)-{4-[5-(5-Ethyl-(1S,4S)-2,5-diaza-bicyclo[2.2.1]
hept-2-yl)-imidazo[1,2-c]pyrimidin-7-yl]-pyridin-2-
yl}-(1-phenyl-ethyl)-amine The mixture of 50 mg (0.12 mmol) {4-[5-(2,5-diaza-bicyclo[2.2.1]hept-2-yl)-imidazo [1,2-c]pyrimidin-7-yl]-pyridin-2-yl}-(1-phenyl-ethyl)-amine in 20 mL CH$_3$CN was treated with 26 mg (0.24 mmol) bromoethane and 33 mg (0.24 mmol) K$_2$CO$_3$. The mixture was stirred at rt for 15 h. MS showed all starting materials were converted. The mixture was diluted with 50 mL DCM, washed with 20 mL sat. NaHCO$_3$, dried over anhydrous Na$_2$SO$_4$. After purification by chromatography, obtained the title compound in 20 mg as a yellow solid. MS (ES+): 440 (M+H)$^+$.

EXAMPLE 6

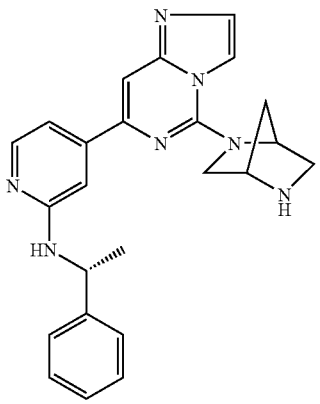

(R)-{4-[5-((1S,4S)-2,5-Diaza-bicyclo[2.2.1]hept-2-
yl)-imidazo[1,2-c]pyrimidin-7-yl]-pyridin-2-yl}-(1-
phenyl-ethyl)-amine Step A: To a 100 mL RBF, was added 5-[7-(2-chloro-pyridin-4-yl)-imidazo[1,2-c]pyrimidin-5-yl]-2,5-diaza-bicyclo[2.2.1]heptane-2-carboxylic acid tert-butyl ester (0.22 g, 0.5 mmol), 50 mL toluene and 2.5 mL DMF, and (R)-α-methylbenzylamine (0.07 mL, 0.55 mmol). The mixture was degassed by nitrogen through for 1 h. After Pd(OAc)$_2$ (12 mg, 0.05 mmol), BINAP (31 mg, 0.05 mmol) and NaOtBu (0.69 g, 1.0 mmol) were added, the mixture was warmed up to 90° C. and stirred for 2 h under nitrogen. The mixture was cooled down to rt, diluted with 100 mL DCM, washed with 20 mL sat. NaHCO$_3$, and dried over anhydrous Na$_2$SO$_4$. After purification by flash chromatography, obtained the (R)-5-{7-[2-(1-phenyl-ethylamino)-pyridin-4-yl]-imidazo[1,2-c]pyrimidin-5-yl}-2,5-diaza-bicyclo[2.2.1]heptane-2-carboxylic acid tert-butyl ester in as pale yellow solid. MS (ES+): 512 (M+H)$^+$.

Step B: To a 50 mL RBF was added 0.25 g (0.49 mmol)(R)-5-{7-[2-(1-phenyl-ethylamino)-pyridin-4-yl]-imidazo[1,2-c]pyrimidin-5-yl}-2,5-diaza-bicyclo[2.2.1]-heptane-2-carboxylic acid tert-butyl ester, 5 mL methanol and stirred at rt under nitrogen. The mixture was treated with and 2.0 mL 4N HCl in dioxane and was stirred at rt for 1 h. The mixture was diluted with 100 mL DCM, washed with 20 mL sat. NaHCO$_3$, and dried over anhydrous Na$_2$SO$_4$. After purification by flash chromatography, obtained the title compound as a pale yellow solid. MS (ES+): 412 (M+H)$^+$.

EXAMPLE 7

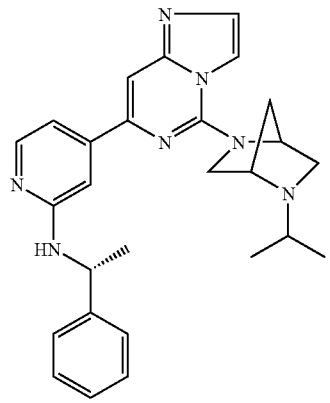

(R)-{4-[5-(5-Isopropyl-(1S,4S)-2,5-diaza-bicyclo
[2.2.1]hept-2-yl)-imidazo[1,2-c]pyrimidin-7-yl]-
pyridin-2-yl}-(1-phenyl-ethyl)-amine The mixture of 100 mg (0.24 mmol)(R)-{4-[5-(2,5-diaza-bicyclo[2.2.1]hept-2-yl)-imidazo[1,2-c]pyrimidin-7-yl]-pyridin-2-yl}-(1-phenyl-ethyl)-amine in 5 mL chloroform was treated with 0.2 mL (2.4 mmol) acetone, 45 mg (0.72 mmol) NaBH$_3$(CN) and 1 mL methanol. The mixture was stirred at rt for 15 h. MS showed all starting materials were converted. The mixture was diluted with 100 mL DCM, washed with 20 mL sat. NaHCO$_3$, dried over anhydrous Na$_2$SO$_4$. After purification by chromatography, obtained the title compound as a yellow solid. MS (ES+): 454 (M+H)$^+$.

EXAMPLE 8

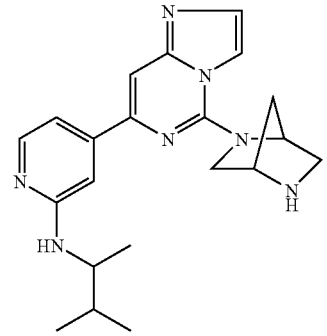

{4-[5-((1S,4S)-2,5-Diaza-bicyclo[2.2.1]hept-2-yl)-
imidazo[1,2-c]pyrimidin-7-yl]-pyridin-2-yl}-(1
,2-dimethyl-propyl)-amine Step A: To a 100 RBF, was added 5-[7-(2-chloro-pyridin-4-yl)-imidazo[1,2-c]pyrimidin-5-yl]-2,5-diaza-bicyclo[2.2.1]heptane-2-carboxylic acid tert-butyl ester (0.14 g, 0.33 mmol), 20 mL toluene and 2.5 mL DMF, and 1,2-dimethyl-propylamine (0.057 g, 0.66 mmol). The mixture was degassed by nitrogen through for 1 h. After Pd(OAc)$_2$ (7.4 mg, 0.033 mmol), BINAP (21 mg, 0.033 mmol) and NaOtBu (0.063 g, 0.66 mmol) were added, the mixture was warmed up to 90° C. and stirred for 2 h under nitrogen. The mixture was cooled down to rt, diluted with 100 mL DCM, washed with 20 mL sat. NaHCO$_3$, and dried over anhydrous Na$_2$SO$_4$. After purification by flash chromatography, obtained the 5-{7-[2-(1,2-dimethyl-propylamino)-pyridin-4-yl]-imidazo[1,2-c]pyrimidin-5-yl}-2,5-diaza-bicyclo[2.2.1]heptane-2-carboxylic acid tert-butyl ester as a pale yellow solid. MS (ES+): 478 (M+H)+.

Step B: To a 50 mL RBF was added 0.1 g (0.21 mmol) 5-{7-[2-(1,2-dimethyl-propylamino)-pyridin-4-yl]-imidazo[1,2-c]pyrimidin-5-yl}-2,5-diaza-bicyclo[2.2.1]-heptane-2-carboxylic acid tert-butyl ester, 5 mL methanol and stirred at rt under nitrogen. The mixture was treated with and 2.0 mL 4N HCl in dioxane and was stirred at rt for 1 h. The mixture was diluted with 100 mL DCM, washed with 20 mL sat. NaHCO3, and dried over anhydrous Na2SO4. After purification by flash chromatography, obtained the title compound as a pale yellow solid. MS (ES+): 378 (M+H)+.

EXAMPLE 9

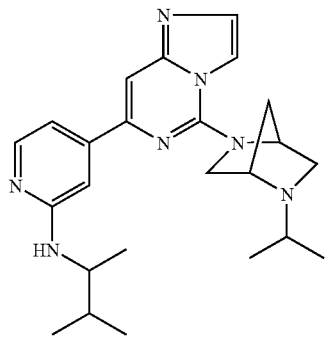

(1,2-Dimethyl-propyl)-{4-[5-(5-isopropyl-(1S,4S)-2,5-diaza-bicyclo[2.2.1]hept-2-yl)-imidazo[1,2-c]pyrimidin-7-yl]-pyridin-2-yl}-amine The mixture of 25 mg (0.066 mmol) {4-[5-(2,5-diaza-bicyclo[2.2.1]hept-2-yl-)-imidazo[1,2-c]pyrimidin-7-yl]-pyridin-2-yl}-(1,2-dimethyl-propyl)-amine in 5 mL chloroform was treated with 38 mg (0.66 mmol) acetone, 41 mg (0.66 mmol) NaBH3(CN) and 1 mL methanol. The mixture was stirred at rt for 15 h. MS showed all starting materials were converted. The mixture was diluted with 100 mL DCM, washed with 20 mL sat. NaHCO3, dried over anhydrous Na2SO4. After purification by chromatography, obtained the title compound as a yellow solid. MS (ES+): 420 (M+H)+.

EXAMPLE 10

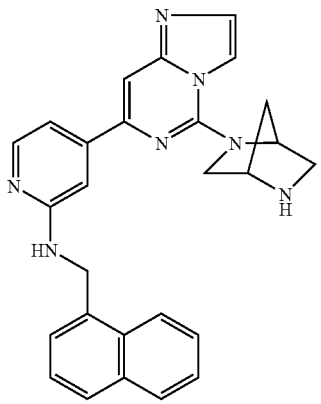

{4-[5-((1S,4S)-2,5-Diaza-bicyclo[2.2.1]hept-2-yl)-imidazo[1,2-c]pyrimidin-7-yl]-pyridin-2-yl}-Naphthalen-1-ylmethyl-amine Step A: To a 100 mL RBF, was added 5-[7-(2-chloro-pyridin-4-yl)-imidazo[1,2-c]pyrimidin-5-yl]-2,5-diaza-bicyclo[2.2.1]heptane-2-carboxylic acid tert-butyl ester (0.22 g, 0.5 mmol), 50 mL toluene and 2.5 mL DMF, and C-Naphthalen-1-yl-methylamine (94 mg, 0.6 mmol). The mixture was degassed by nitrogen bubbled through for 1 h. After Pd(OAc)2 (12 mg, 0.05 mmol), BINAP (31 mg, 0.05 mmol) and NaOtBu (0.69 g, 1.0 mmol) were added, the mixture was warmed up to 90° C. and stirred for 2 h under nitrogen. The mixture was cooled down to rt, diluted with 100 mL DCM, washed with 20 mL sat. NaHCO3, and dried over anhydrous Na2SO4. After purification by flash chromatography, obtained the 5-(7-{2-[(naphthalen-1-ylmethyl)-amino]-pyridin-4-yl}-imidazo[1,2-c]pyrimidin-5-yl)-2,5-diaza-bicyclo[2.2.1]heptane-2-carboxylic acid tert-butyl ester in 0.25 g as a pale yellow solid. MS (ES+): 548 (M+H)+.

Step B: To a 50 mL RBF was added 0.25 g (0.46 mmol) 5-(7-{2-[(naphthalen-1-ylmethyl)-amino]-pyridin-4-yl}-imidazo[1,2-c]pyrimidin-5-yl)-2,5-diaza-bicyclo[2.2.1]heptane-2-carboxylic acid tert-butyl ester, 5 mL methanol and stirred at rt under nitrogen. The mixture was treated with and 2.0 mL 4N HCl in dioxane and was stirred at rt for 1 h. The mixture was diluted with 100 mL DCM, washed with 20 mL sat. NaHCO3, and dried over anhydrous Na2SO4. After purification by flash chromatography, obtained the title compound as a pale yellow solid. MS (ES+): 448(M+H)+.

EXAMPLE 11

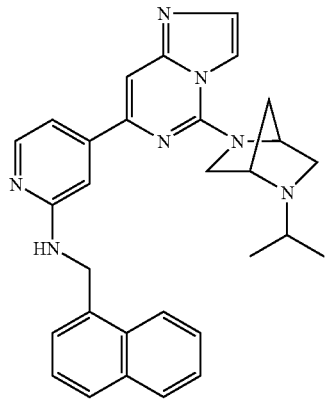

{4-[5-(5-Isopropyl-(1S,4S)-2,5-diaza-bicyclo[2.2.1]hept-2-yl)-imidazo[1,2-c]pyrimidin-7-yl]-pyridin-2-yl}—Naphthalen-1-ylmethyl-amine The mixture of 92 mg (0.2 mmol) {4-[5-(2,5-diaza-bicyclo[2.2.1]hept-2-yl)-imidazo[1,2-c]pyrimidin-7-yl]-pyridin-2-yl}-Naphthalen-1-ylmethyl-amine in 5 mL chloroform was treated with 0.12 g (2.0 mmol) acetone, 41 mg (0.66 mmol) NaBH3(CN) and 1 mL methanol. The mixture was stirred at rt for 15 h. MS showed all starting materials were converted. The mixture was diluted with 100 mL DCM, washed with 20 mL sat. NaHCO₃, and dried over anhydrous Na₂SO₄. After purification by chromatography, the title compound was obtained as a yellow solid.
MS (ES+): 490 (M+H)⁺.

EXAMPLE 12

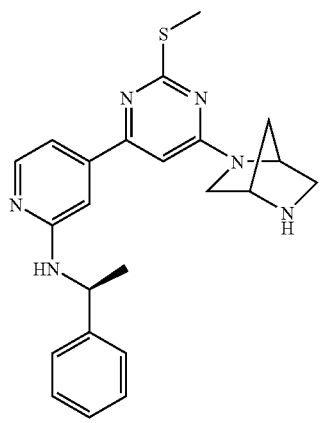

(S)-{4-[6-((1S,4S)-2,5-Diaza-bicyclo[2.2.1]hept-2-yl)-2-methylsulfanyl-pyrimidin-4-yl]-pyridin-2-yl}-(1-phenyl-ethyl)-amine Step A: To a 250 mL RBF was added 4-chloro-6-(2-chloro-pyridin-4-yl)-2-methylsulfanyl-pyrimidine (2.13 g, 7.86 mmol), 100 mL CH₃CN, (S)-N-Boc-2,5-diaza-bicyclo[2.2.1]heptane (1.71 g, 8.65 mmol), K₂CO₃ (1.1 g, 7.86 mmol). The mixture was refluxed under nitrogen for 4 h, and all starting material was converted. The reaction mixture was cooled down to rt, diluted with 200 mL ethyl acetate, washed with 50 ml sat. NaHCO₃, and dried over anhydrous Na₂SO₄. After purification by flash chromatograph, the intermediate 5-[6-(2-chloro-pyridin-4-yl)-2-methylsulfanyl-pyrimidin-4-yl]-2,5-diaza-bicyclo[2.2.1]heptane-2-carboxylic acid tert-butyl ester was obtained. MS (ES+): 434 (M+H)⁺.

Step B: To a 100 mL RBF, was added 5-[6-(2-chloro-pyridin-4-yl)-2-methyl-sulfanylpyrimidin-4-yl]-2,5-diaza-bicyclo[2.2.1]heptane-2-carboxylic acid tert-butyl ester (0.433 g, 1 mmol), 50 mL toluene, and (S)-α-methylbenzylamine (0.15 mL, 1.2 mmol). The mixture was degassed by nitrogen bubbled through for 1 h. After Pd(OAc)₂ (23 mg, 0.1 mmol), BINAP (62 mg, 0.1 mmol) and NaOtBu (0.192 g, 2.0 mmol) were added, the mixture was warmed up to 90° C. and stirred for 2 h under nitrogen. The mixture was cooled down to rt, diluted with 100 mL DCM, washed with 20 mL sat. NaHCO₃, and dried over anhydrous Na₂SO₄. After purification by flash chromatography, obtained the 5-{2-methylsulfanyl-6-[2-(1-phenyl-ethylamino)-pyridin-4-yl]-pyrimidin-4-yl}-2,5-diaza-bicyclo[2.2.1]heptane-2-carboxylic acid tert-butyl ester as pale yellow solid. MS (ES+): 519 (M+H)⁺.

Step C: To a 50 mL RBF was added 0.4 g (0.77 mmol) 5-{2-methylsulfanyl-6-[2-(1-phenyl-ethylamino)-pyridin-4-yl]-pyrimidin-4-yl}-2,5-diaza-bicyclo[2.2.1]heptane-2-carboxylic acid tert-butyl ester, 10 mL methanol and stirred at rt under nitrogen. The mixture was treated with and 2.5 mL 4N HCl in dioxane and was stirred at rt for 1 h. The mixture was diluted with 100 mL DCM, washed with 20 mL sat. NaHCO₃, and dried over anhydrous Na₂SO₄. After purification by flash chromatography, obtained the title compound as a pale yellow solid. MS (ES+): 419 (M+H)⁺.

EXAMPLE 13

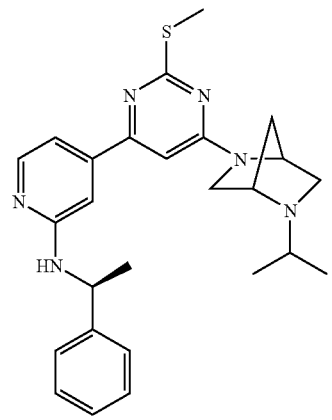

(S)-{4-[6-(5-Isopropyl-(1S,4S)-2,5-diaza-bicyclo[2.2.1]hept-2-yl)-2-methylsulfanyl-pyrimidin-4-yl]-pyridin-2-yl}-(1-phenyl-ethyl)-amine The mixture of 0.13 g (0.31 mmol) {4-[6-(2,5-diaza-bicyclo[2.2.1]hept-2-yl)-2-methylsulfanyl-pyrimidin-4-yl]-pyridin-2-yl}-(1-phenyl-ethyl)-amine in 5 mL chloroform was treated with 0.2 mL (3.1 mmol) acetone, 0.19 g (3.1 mmol) NaBH₃(CN) and 1 mL methanol. The mixture was stirred at rt for 15 h. MS showed all starting materials were converted. The mixture was diluted with 100 mL DCM, washed with 20 mL sat. NaHCO₃, dried over anhydrous Na₂SO₄. After purification by chromatography, the title compound was obtained as a yellow solid. MS (ES+): 461 (M+H)⁺.

EXAMPLE 14

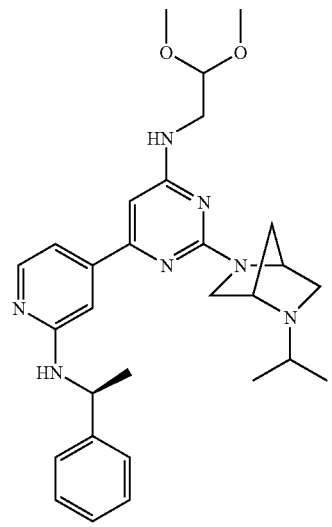

(S)-(2,2-Dimethoxy-ethyl)-{2-(5-isopropyl-(1S,4S)-2,5-diaza-bicyclo[2.2.1]hept-2-yl)-6-[2-(1-phenyl-ethylamino)-pyridin-4-yl]-pyrimidin-4-yl}-amine Step A: The mixture of 0.36 g (1.06 mmol) [6-(2-chloro-pyridin-4-yl)-2-methylsulfanyl-pyrimidin-4-yl]-(2,2-dimethoxy-ethyl)-amine in 15 mL methanol and 10 mL acetone was treated with 0.37 g (0.6 mmol) Oxone and 32 mg (0.106 mmol) tetrabutylammonium nitrate in 4 mL water at 0° C. The mixture was stirred at 0° C. for 4 h, all starting material was converted. The reaction mixture was treated with 10 mL sat. Na$_2$S$_2$O$_3$, extracted with DCM 3×50 mL, dried with anhydrous Na$_2$SO$_4$. After purification by flash chromatograph, the intermediate [6-(2-chloro-pyridin-4-yl)-2-methanesulfinyl-pyrimidin-4-yl]-(2,2-dimethoxy-ethyl)-amine was obtained. MS (ES+): 357 (M+H)$^+$.

Step A: To a 100 mL RBF was added [6-(2-chloro-pyridin-4-yl)-2-methanesulfinyl-pyrimidin-4-yl]-(2,2-dimethoxy-ethyl)-amine (0.21 g, 0.59 mmol), 10 mL DMF, (S)-2-isopropyl-2,5-diaza-bicyclo[2.2.1]heptane hydrochloride salt (0.15 g, 0.7 mmol), K$_2$CO$_3$ (0.24 g, 1.77 mmol). The mixture was stirred at 100° C. under nitrogen for 15 h, and all starting material was converted. The reaction mixture was cooled down to rt, diluted with 100 mL DCM, washed with 50 mL sat. NaHCO$_3$, and dried over anhydrous Na$_2$SO$_4$. After purification by flash chromatograph, the intermediate [6-(2-chloro-pyridin-4-yl)-2-(5-isopropyl-2,5-diaza-bicyclo[2.2.1]hept-2-yl)-pyrimidin-4-yl]-(2,2-dimethoxy-ethyl)-amine was obtained. MS (ES+): 433 (M+H)$^+$.

Step B: To a 100 mL RBF, was added [6-(2-chloro-pyridin-4-yl)-2-(5-isopropyl-2,5-diaza-bicyclo[2.2.1]hept-2-yl)-pyrimidin-4-yl]-(2,2-dimethoxy-ethyl)-amine (0.2 g, 0.46 mmol), 25 mL toluene, and (S)-α-methylbenzylamine (0.071 mL, 0.55 mmol). The mixture was degassed by nitrogen bubbled through for 1 h. After Pd(OAc)$_2$ (11 mg, 0.046 mmol), BINAP (29 mg, 0.046 mmol) and NaOtBu (0.088 g, 0.92 mmol) were added, the mixture was warmed up to 90° C. and stirred for 2 h under nitrogen. The mixture was cooled down to rt, diluted with 100 mL DCM, washed with 20 mL sat. NaHCO$_3$, and dried over anhydrous Na$_2$SO$_4$. After purification by flash chromatography, the compound was obtained as a pale yellow solid. MS (ES+): 518 (M+H)$^+$.

EXAMPLE 15

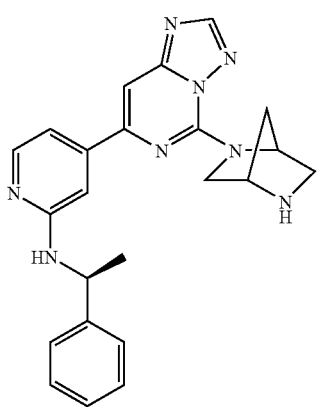

(S)-{4-[5-((1S,4S)-2,5-Diaza-bicyclo[2.2.1]hept-2-yl)-[1,2,4]triazolo[1,5-c]pyrimidin-7-yl]-pyridin-2-yl}-(1-phenyl-ethyl)-amine To 5-{7-[2-(1-phenyl-ethylamino)-pyridin-4-yl]-[1,2,4]triazolo[4,3-c]pyrimidin-5-yl}-2,5-diaza-bicyclo[2.2.1]hep-tene-2-carboxylic acid tert-butyl ester (0.022 g, 0.043 mmol) were added 4N HCl (1 mL) in dioxane and a few drops of methanol. After 1 h, the reaction was concentrated in vacuo and the residue was taken up in water and extracted with ethyl acetate. The aqueous layer was neutralized with saturated sodium bicarbonate and extracted with chloroform (3×). The combined organic extract was dried (K$_2$CO$_3$), filtered, and concentrated in vacuo to give the title compound as a golden yellow solid. MS (ES+): 413.1 [M+H]+, 411.2 [M−H]−.

EXAMPLE 16

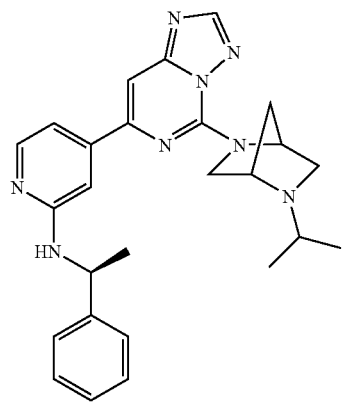

(S)-{4-[5-(5-Isopropyl-(1S,4S)-2,5-diaza-bicyclo[2.2.1]hept-2-yl)-[1,2,4]triazolo[1,5-c]pyrimidin-7-yl]-pyridin-2-yl}-(1-phenyl-ethyl)-amine A solution of {4-[5-(2,5-diaza-bicyclo[2.2.1]hept-2-yl)-[1,2,4]triazolo[4,3-c]pyrimidin-7-yl]-pyridin-2-yl}-(1-phenyl-ethyl)-amine (0.25 g, 0.61 mmol) in chloroform (5 mL) were added acetone (1 mL) and sodium triacetoxyborohydride (0.45 g, 2.14 mmol) and stirred at 70° C. for 2 h. Upon cooling to room temperature, the reaction was diluted with methylene chloride and washed with saturated sodium bicarbonate, brine, and dried (K$_2$CO$_3$). Flash chromatography of the crude product with 1% 2M NH$_3$ in MeOH/CHCl$_3$ afforded the title compound as an off-white solid. MS (ES+): 455.2 [M+H]+, 453.2 [M−H]−.

EXAMPLE 17

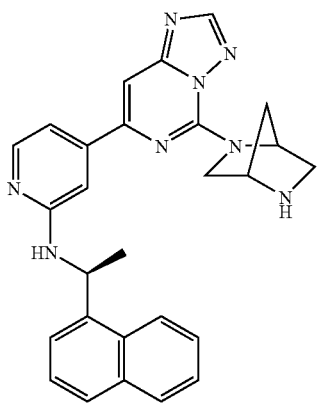

(S)-{4-[5-((1S,4S)-2,5-Diaza-bicyclo[2.2.1]hept-2-yl)-[1,2,4]triazolo[1,5-c]pyrimidin-7-yl]-pyridin-2-yl}-(1-naphthalen-1-yl-ethyl)-amine The title compound was prepared analogously by following the procedure described in Example 2 from 5-{7-[2-(1-naphthalen-1-yl-ethylamino)-pyridin-4-yl]-[1,2,4]triazolo-[4,3-c]pyrimidin-5-yl}-2,5-diaza-bicyclo[2.2.1]heptene-2-carboxylic acid tert-butyl ester. MS (ES+): 463.3 [M+H]+, 461.3 [M−H]−.

EXAMPLE 18

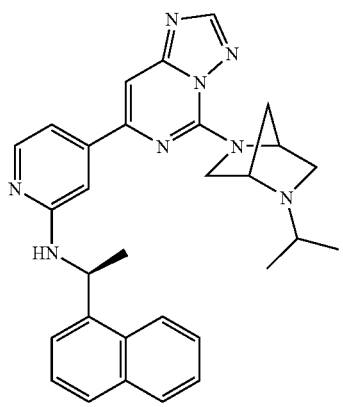

(S)-{4-[5-(5-Isopropyl-(1S,4S)-2,5-diaza-bicyclo[2.2.1]hept-2-yl)-[1,2,4]triazolo[1,5-c]pyrimidin-7-yl]-pyridin-2-yl}-(1-naphthalen-1-yl-ethyl)-amine The title compound was prepared analogously by following the procedure described in Example 3 from {4-[5-(2,5-diaza-bicyclo[2.2.1]hept-2-yl)-[1,2,4]triazolo[4,3-c]pyrimidin-7-yl]-pyridin-2-yl}-(1-naphthalen-1-yl-ethyl)-amine. MS (ES+): 505.3 [M+H]+, 503.4 [M−H]−.

EXAMPLE 19

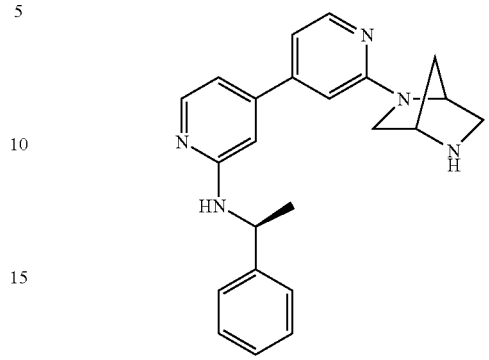

(S)-[2'-((1S,4S)-2,5-Diaza-bicyclo[2.2.1]hept-2-yl)-[4,4']bipyridinyl-2-yl]-(1-phenyl-ethyl)-amine To 5-[2'-(1-phenyl-ethylamino)-[4,4']bipyridinyl-2-yl]-2,5-diazabicyclo[2.2.1]-heptane-2-carboxylic acid tert-butyl ester (0.027 g, 0.058 mmol) were added 4N HCl (1 mL) in dioxane and a few drops of methanol. After 1 h, the reaction was concentrated in vacuo and the residue was taken up in water and extracted with ethyl acetate. The aqueous layer was neutralized with saturated sodium bicarbonate and extracted with chloroform (3×). The combined organic extract was dried (K$_2$CO$_3$), filtered, and concentrated in vacuo to give the title compound as a golden yellow solid. MS (ES+): 372.4 [M+H]+, 370.3 [M−H]−.

EXAMPLE 20

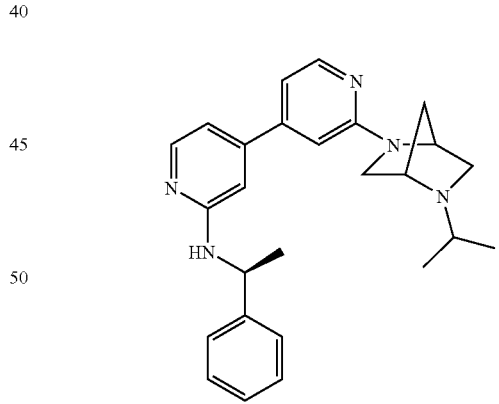

(S)-[2'-(5-Isopropyl-(1S,4S)-2,5-diaza-bicyclo[2.2.1]hept-2-yl)-[4,4']bipyridinyl-2-yl]-(1-phenyl-ethyl)-amine The title compound was prepared analogously by following the procedure described in Example 3 from [2'-(2,5-diaza-bicyclo[2.2.1]hept-2-yl)-[4,4']bipyridinyl-2-yl]-(1-phenyl-ethyl)-amine. MS (ES+): 414.2 [M+H]+, 412.3 [M−H]−.

EXAMPLE 21

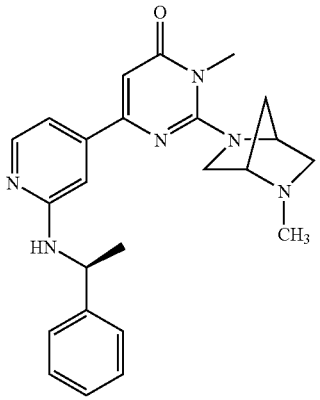

3-Methyl-2-(5-methyl-(1S,4S)-2,5-diaza-bicyclo
[2.2.1]hept-2-yl)-6-[2-(S)-(1-phenyl-ethylamino)-
pyridin-4-yl]-3H-pyrimidin-4-one To a solution of 2-(2,5-diaza-bicyclo[2.2.1]hept-2-yl)-3-methyl-6-[2-(1-phenyl-ethylamino)-pyridin-4-yl]-3H-pyrimidin-4-one (0.05 g, 0.13 mmol, 1.00 equiv) in methanol 15 mL was added formaldehyde (37% wt, 0.07 g, 5.40 mmol, 20 equiv) and sodium triacetoxyboronhydride (0.06 g, 0.27 mmol, 2.00 equiv) at 0° C. The reaction was warmed to room temperature overnight, after that solvent was evaporated. Filtration and purification by HPLC give the desired product as an off-white solid. ¹H NMR (CDCl₃, 400 MHz): δ 8.13 (d, J=5.2 Hz, 1H), 7.39 (d, J=8.4 Hz, 2H), 7.337-7.35 (m, 2H), 6.98 (dd, J=5.2, 1.6 Hz, 1H), 6.76 (s, 1H), 6.35 (s, 1H), 5.09 (s, br, 1H), 4.78-4.74 (m, 1H), 4.42 (s, 1h), 3.51-3.42 (m, 6H), 3.05 (d, J=10.4 Hz, 1H), 2.89 (dd, J=6.0, 2.4 Hz, 1H), 2.43 (s, 3H), 1.95 (d, J=9.6 Hz, 1H), 1.74 (d, J=10.0 Hz, 1H), 1.58 (d, J=6.8 Hz, 3H); ¹³C NMR (CDCl₃, 400 MHz): δ 165.25, 158.66, 157.76, 156.90, 148.57, 145.93, 144.52, 128.71, 127.07, 125.82, 110.56, 104.18, 101.38, 63.30, 61.55, 59.63, 54.20, 52.21, 41.28, 34.49, 32.71, 24.51 ppm; MS (ES+): 417.2 (M+H)⁺; (ES−): 415.5 (M−H)−. HRMS calcd for C₂₄H₂₉N₆O 417.2403, found 417.2414.

EXAMPLE 22

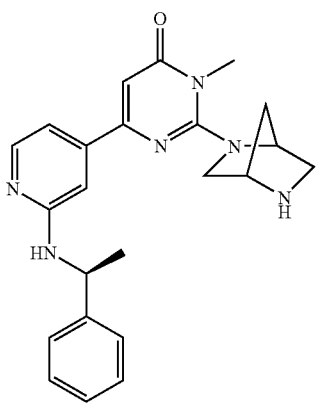

2-((1S,4S)-2,5-Diaza-bicyclo[2.2.1]hept-2-yl)-3-
methyl-6-[2-((S)-1-phenyl-ethylamino)-pyridin-4-
yl]-3H-pyrimidin-4-one Step A: 3-(2-Chloro-pyridin-4-yl)-3-oxo-propionic acid ethyl ester To 60.8 mL of LHMS (1.0 M in THF) was added slowly a solution of 2-chloro-isonicotinic acid ethyl ester (10.28 g, 55 mmol) and 4.8 g of ethyl acetate (65 mmol) in 5 mL anhydrous THF at 0° C. under nitrogen. The resulted mixture was stirred at 0° C.—rt for 15 h, then quenched with 900 mL of hexanes. After stirring for 2 h at room temperature, the solids formed were filtered and washed with hexanes to give 3-(2-chloro-pyridin-4-yl)-3-oxo-propionic acid ethyl ester lithium enolate.

Step B: 6-(2-Chloro-pyridin-4-yl)-2-methylsulfanyl-3-methyl-pyrimidin-4-one

The mixture of 7.44 g of 3-(2-chloro-pyridin-4-yl)-3-oxo-propionic acid ethyl ester lithium enolate (32 mmol), thiourea (2.42 g, 32 mmol), and potassium carbonate (4.6 g, 33 mmol) in 10 mL ethanol and 10 mL DMF was heated at 95° C. under nitrogen overnight. The mixture was cooled to room temperature, and treated with methyl iodide (4.8 mL) and then stirred overnight. The mixture was quenched with 150 mL ice water. The solids formed were filtered and washed with water to give the titled compound. MS (ES+): 268 (M+H)⁺.

Step C: 1,1-Dimethylethyl 5-(1-methyl-6-oxo-4-(2-chloro-4-pyridinyl)-1,6-dihydro-2-pyrimidinyl)-2,5-diazabicyclo[2.2.1]heptane-2-carboxylate To 6-(2-chloro-pyridin-4-yl)-2-methylsulfanyl-3-methyl-pyrimidin-4-one (2.39 g, 8.9 mmol) in acetonitrile (50 mL) at 0° C. was added 33 mL of trifluoroperacetic acid solution, formed in situ from urea hydrogen peroxide addition compound (Aldrich, 10.44 g, 110 mmol) and trifluoro acetic anhydride (46.8 g, 222 mmol) in 78 mL of acetonitrile at 0° C. The mixture was stirred at 0° C. for 40 min, and sodium carbonate (18.4 g) was added slowly. After 20 min, (1S,4S)-2,5-diazabicyclic[2.2.1]heptane-2-carboxylic acid 1,1- (Aldrich, 2.3 g, 11.6 mmol) was added. The mixture was stirred 0° C. to room temperature overnight. Ethyl acetate (700 mL) was added and the mixture was washed with brine (4×100 mL), dried, filtered, and evaporated to give the crude product. Column chromatograph purification (silica gel, 20-75% EtOAc/hexanes) gave 1,1-dimethylethyl 5-(1-methyl-6-oxo-4-(2-chloro-4-pyridinyl)-1,6-dihydro-2-pyrimidinyl)-2,5-diazabicyclo[2.2.1]heptane-2-carboxylate. MS (ES+): 418.3 (M+H)⁺.

Step D: 2-(2,5-Diaza-bicyclo[2.2.1]hept-2-yl)-3-methyl-6-[2-((1S)-1-phenylethyl)-amino)-pyridin-4-yl]-3H-pyrimidin-4-one The titled compound was made from 1,1-dimethylethyl 5-(1-methyl-6-oxo-4-(2-chloro-4-pyridinyl)-1,6-dihydro-2-pyrimidinyl)-2,5-diazabicyclo[2.2.1]heptane-2-carboxylate according to the procedures described in Example 3. MS (ES+): 403.4 (M+H)⁺.

EXAMPLE 23

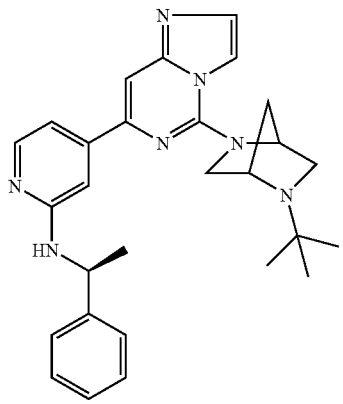

(S)-{4-[5-(5-tert-Butyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine Step A: To a 250 mL RBF, was added trans-4-hydroxy-L-proline, (2S,4R)-4-hydroxy-pyrrolidine-2-carboxylic acid) (13.1 g, 100 mmol), and 50 mL absolute ethanol. The above mixture was cooled down to 0° C. and saturated with HCl gas until all of the suspension was dissolved. The mixture was refluxed under nitrogen for 2 h. The mixture was cooled down to rt, and all solvent was removed by vacuum. The residue was kept in the refrigerator for 15 h, the white precipitate was filtered and washed with anhydrous ether 3×50 mL, to obtain the (2S,4R)-4-hydroxy-pyrrolidine-2-carboxylic acid ethyl ester HCl salt as a white solid. MS (ES+): 160 (M+H)$^+$.

Step B: The mixture of 19.5 g (100 mmol) (2S,4R)-4-hydroxy-pyrrolidine-2-carboxylic acid ethyl ester HCl salt in 250 mL 1 N NaOH was cooled down to 0° C. and stirred under nitrogen. The mixture was treated with 26 g (Boc)$_2$O, and the mixture was stirred at 0° C. to rt for 1 h. The mixture was quenched with 100 mL sat. NH$_4$Cl, extracted with ethyl acetate 3×100 mL. The combined organic was washed with brine 50 mL, and dried over anhydrous Na$_2$SO$_4$. After purification by flash chromatography, obtained (2S,4R) 4-hydroxy-pyrrolidine-1,2-dicarboxylic acid 1-tert-butyl ester 2-ethyl ester 23 g as white solid. MS (ES+): 260 (M+H)$^+$.

Step C: The mixture of 5.2 g (20 mmol) (2S, 4R)-4-hydroxy-pyrrolidine-1,2-dicarboxylic acid 1-tert-butyl ester 2-ethyl ester in 100 mL THF was treated with 0.76 g (20 mmol) LAH at 0° C. The mixture was stirred at 0° C. to rt for 3.5 h. The mixture was cooled down to 0° C., the excess LAH was quenched with 10 mL ethyl acetate. Sat. NH$_4$Cl was added carefully until fine white precipitate was formed, filtered and washed with ethyl acetate 3×100 mL. The combined organic layers was dried over anhydrous Na$_2$SO$_4$. After purification by flash chromatography, obtained (2S,4R) 4-hydroxy-2-hydroxymethyl-pyrrolidine-1-carboxylic acid tert-butyl ester as a colourless oil. MS (ES+): 218 (M+H)$^+$.

Step D: The mixture of 4.0 g (18 mmol) (2S,4R) 4-hydroxy-2-hydroxymethyl-pyrrolidine-1-carboxylic acid tert-butyl ester in 20 mL pyridine was cooled down to 0° C. and stirred under nitrogen. The mixture was treated with 14 g (74 mmol) TsCl. The mixture was stirred at 0° C. to rt for 15 h. The mixture was added to 100 mL ice water and stirred for 10 min. The pale yellow solid was collected and further purified by flash chromatography, obtained as Ts protected (2S, 4R)-4-hydroxy-2-hydroxymethyl-pyrrolidine-1-carboxylic acid tert-butyl ester 6.7 g as a white solid.
MS (ES+): 548 (M+Na)+.

Step E: The mixture of 0.52 g (1 mmol) Ts protected (2S,4R)-4-hydroxy-2-hydroxymethyl-pyrrolidine-1-carboxylic acid tert-butyl ester, and 1.1 mL (10 mmol) tert-butylamine in 10 mL toluene was heated up to 110° C. in a sealed tube and stirred for 15 h. The mixture was cooled down to rt, all solvent was removed by vacuum, and purified by flash chromatography. The (1S, 4S)-5-tert-butyl-2,5-diaza-bicyclo[2.2.1]heptane-2-carboxylic acid tert-butyl ester was obtained in as a white solid. MS (ES+): 255 (M+H)$^+$.

Step F: To a 50 mL RBF was added 0.12 g (0.47 mmol) (1S, 4S)-5-tert-butyl-2,5-diaza-bicyclo[2.2.1]heptane-2-carboxylic acid tert-butyl ester, 10 mL methanol and stirred at rt under nitrogen. The mixture was treated with 2.5 mL 4 N HCl in dioxane and was stirred at rt for 1 h. The solvent was removed by vacuum to give crude (1S,4S)-2-tert-butyl-2,5-diaza-bicyclo[2.2.1]heptane as a pale yellow solid.
MS (ES+): 155 (M+H)$^+$ Step G: The mixture of above crude 0.15 g (1S, 4S)-2-tert-butyl-2,5-diaza-bicyclo[2.2.1]heptane in 20 mL DCM was treated 0.245 mL DIEA (1.3 mmol) and 0.124 g (0.6 mmol) 5-chloro-7-(2-chloro-pyridin-4-yl)-imidazo[1,2-c]pyrimidine. The mixture was stirred at rt under nitrogen for 15 h. The mixture was diluted with 100 mL DCM, washed with 20 mL sat. NaHCO$_3$, dried over anhydrous Na$_2$SO$_4$. After purification by flash chromatography, obtained the (S,S)-7-(2-chloro-pyridin-4-yl)-5-(5-tert-butyl-2,5-diaza-bicyclo[2.2.1]hept-2-yl)-imidazo[1,2-c]pyrimidine as a yellow solid. MS (ES+): 383 (M+H)$^+$.

Step H: To a 100 mL RBF, was added (S,S)-7-(2-chloro-pyridin-4-yl)-5-(5-tert-butyl-2,5-diaza-bicyclo[2.2.1]hept-2-yl)-imidazo[1,2-c]pyrimidine (0.15 g, 0.39 mmol), 20 mL toluene, and (S)-α-methylbenzylamine (0.061 mL, 0.47 mmol). The mixture was degassed by nitrogen bubbled through for 1 h. After Pd(OAc)$_2$ (9 mg, 0.039 mmol), BINAP (25 mg, 0.039 mmol) and NaOtBu (0.075 g, 0.78 mmol) were added, the mixture was warmed up to 90° C. and stirred for 2 h under nitrogen. The mixture was cooled down to rt, diluted with 100 mL DCM, washed with 20 mL sat. NaHCO$_3$, and dried over anhydrous Na$_2$SO$_4$. After purification by flash chromatography, obtained the title compound as a pale yellow solid. MS (ES+): 468 (M+H)$^+$.

EXAMPLE 24

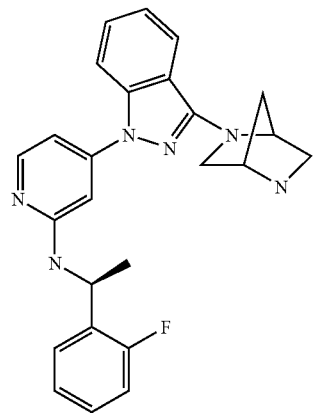

(S)-{4-[3-((1S,4S)-2,5-Diaza-bicyclo[2.2.1]hept-2-yl)-indazol-1-yl]-pyridin-2-yl}-[1-(2-fluoro-phenyl)-ethyl]-amine The title compound was analogously synthesized by the method described in example 1. 2-Bromo-benzoic acid, instead of 2-bromo-4-fluoro-benzoic acid was used. 1-(2-Fluoro-phenyl)-ethylamine, instead of 1-phenyl-ethylamine, was used. MS (ES+): 427 (M+H)+; (ES−): 425 (M−H)−.

EXAMPLE 25

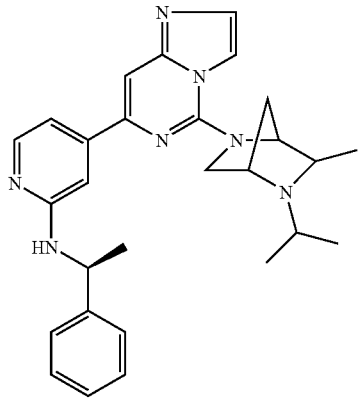

(S)-{4-[5-(5-Isopropyl-6-methyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine Step A: The mixture of 4.2 g (16.2 mmol) (2S, 4R) 4-hydroxy-pyrrolidine-1,2-dicarboxylic acid 1-tert-butyl ester 2-ethyl ester in 20 mL DMF was treated with 1.65 g (24.3 mmol) imidazole, and 5.1 mL (19.5 mmol) TBDPSCl consequently at 0° C. The mixture was stirred at 0° C. to rt for 2 h. The mixture was diluted with 200 mL ethyl acetate, washed with H$_2$O 3×50 mL, brine 50 mL, and dried over anhydrous Na$_2$SO$_4$. After purification by flash chromatography, obtained (2S,4R)-4-TBDPShydroxy-2-hydroxymethyl-pyrrolidine-1-carboxylic acid tert-butyl ester as a colourless oil. MS (ES+): 498 (M+H)+.

Step B: The mixture of 1.0 g (2 mmol) (2S,4R)-4-TBDPShydroxy-2-hydroxymethyl-pyrrolidine-1-carboxylic acid tert-butyl ester and 0.23 g (2.4 mmol) N,O-dimethylhydroxylamine HCl salt in 50 mL THF was cooled down to 0° C. and stirred under nitrogen. The mixture was treated with 7.2 mL (10 mmol) MeMgBr dropwise. The mixture was stirred at 0° C. to rt for 4 h. The mixture was added to 100 mL ice water containing 1N HCl 10 mL and stirred for 10 min. The mixture was extracted ethyl acetate 3×50 mL. The combined organic was washed with brine 50 mL, dried over anhydrous Na$_2$SO$_4$. After purification by flash chromatography, obtained (2S,4R)-2-acetyl-4-TBDPShydroxy-pyrrolidine-1-carboxylic acid tert-butyl ester as a pale yellow oil. MS (ES+): 468 (M+H)+.

Step C: The mixture of 0.65 g (1.39 mmol) (2S,4R)-2-acetyl-4-TBDPShydroxy-pyrrolidine-1-carboxylic acid tert-butyl ester in 20 mL THF/H$_2$O (9:1) was treated with 0.11 g (2.78 mmol) NaBH$_4$ at 0° C. The mixture was stirred at 0° C. to rt for 2 h, diluted with 100 mL ethyl acetate, washed with sat. NaHCO$_3$, dried over anhydrous Na$_2$SO$_4$. After purification by flash chromatography, obtained (2S,4R)-4-TBDPShydroxy-2-(1-hydroxy-ethyl)-pyrrolidine-1-carboxylic acid tert-butyl ester as a pale yellow oil. MS (ES+): 470 (M+H)+.

Step D: The mixture of 0.36 g (0.77 mmol) (2S, 4R) 4-TBDPShydroxy-2-(1-hydroxy-ethyl)-pyrrolidine-1-carboxylic acid tert-butyl ester in 10 mL THF was treated with 1.2 mL (1.15 mmol) TBAF at 0° C. The mixture was stirred at 0° C. to rt for 1 h, filtered through Celite, and washed with ethyl acetate 3×50 mL. The combined organic layers were dried over anhydrous Na$_2$SO$_4$. The solvent was removed by vacuum giving the crude (2S,4R)-4-hydroxy-2-(1-hydroxy-ethyl)-pyrrolidine-1-carboxylic acid tert-butyl ester as a pale yellow oil. MS (ES+): 242 (M+H)+.

Step E: The mixture of crude 0.18 g (2S, 4R) 4-hydroxy-2-(1-hydroxy-ethyl)-pyrrolidine-1-carboxylic acid tert-butyl ester in 10 1L pyridine was cooled down to 0° C. and stirred under nitrogen. The mixture was treated with 0.6 g (3.1 mmol) TsCl. The mixture was stirred at 0° C. to rt for 15 h. After all solvent was removed by vacuum, the residue was diluted with 100 mL DCM, washed with H$_2$O 3×50 mL, brine 50 mL, dried over anhydrous Na$_2$SO$_4$. The solvent was removed by vacuum, giving the crude Ts protected (2S, 4R) 4-hydroxy-2-(1-hydroxy-ethyl)-pyrrolidine-1-carboxylic acid tert-butyl ester as a pale yellow solid. MS (ES+): 540 (M+H)+.

Step F: The mixture of crude 0.40 g Ts protected (2S,4R)-4-hydroxy-2-(1-hydroxy-ethyl)-pyrrolidine-1-carboxylic acid tert-butyl ester, and 0.6 mL (7.4 mmol) isopropylamine in 10 mL toluene was heated up to 130° C. in a sealed tube and stirred for 15 h. The mixture was cooled down to rt, all solvent was removed by vacuum, and purified by flash chromatography. The 5-isopropyl-6-methyl-2,5-diaza-bicyclo[2.2.1]heptane-2-carboxylic acid tert-butyl ester was obtained as a white solid. MS (ES+): 255 (M+H)+.

Step G: To a 50 mL RBF was added 30 mg (0.12 mmol) (1S,4S)-5-isopropyl-6-methyl-2,5-diazabicyclo[2.2.1]heptane-2-carboxylic acid tert-butyl ester and 2 mL methanol and the mixture was stirred at rt under nitrogen. The mixture was treated with and 0.5 mL 4 N HCl in dioxane and was stirred at rt for 1 h. The solvent was removed by vacuum, giving the crude (1S,4S)-2-isopropyl-3-methyl-2,5-diaza-bicyclo[2.2.1]heptane as a pale yellow solid. MS (ES+): 155 (M+H)+.

Step H: A mixture of crude 20 mg (1S, 4S)-2-isopropyl-3-methyl-2,5-diaza-bicyclo[2.2.1]heptane in 20 mL DCM was treated 0.1 mL DIEA and 40 mg 5-chloro-7-(2-chloropyridin-4-yl)-imidazo[1,2-c]pyrimidine. The mixture was stirred at rt under nitrogen for 15 h. The mixture was diluted with 100 mL DCM, washed with 20 mL sat. NaHCO$_3$, dried over anhydrous Na$_2$SO$_4$. Purification by flash chromatography gave (S,S)-7-(2-chloro-pyridin-4-yl)-5-(5-isopropyl-6-methyl-2,5-diaza-bicyclo[2.2.1]hept-2-yl)-imidazo[1,2-c]pyrimidine as a yellow solid. MS (ES+): 383 (M+H)+.

Step I: To a 100 mL RBF, was added (7-(2-chloro-pyridin-4-yl)-5-(5-isopropyl-6-methyl-2,5-diaza-bicyclo[2.2.1]hept-2-yl)-imidazo[1,2-c]pyrimidine (20 mg), 20 mL toluene, and (S)-α-methylbenzylamine (0.061 mL, 0.47 mmol). The mixture was degassed by nitrogen bubbled through for 1 h. After Pd(OAc)$_2$ (9 mg, 0.039 mmol), BINAP (25 mg, 0.039 mmol) and NaOtBu (0.075 g, 0.78 mmol) were added, the mixture was warmed up to 90° C. and stirred for 2 h under nitrogen. The mixture was cooled down to rt, diluted with 100 mL DCM, washed with 20 mL sat. NaHCO$_3$, and dried over anhydrous Na$_2$SO$_4$. After purification by flash chromatography, obtained the title compound as a pale yellow solid. MS (ES+): 468 (M+H)+.

EXAMPLE 26

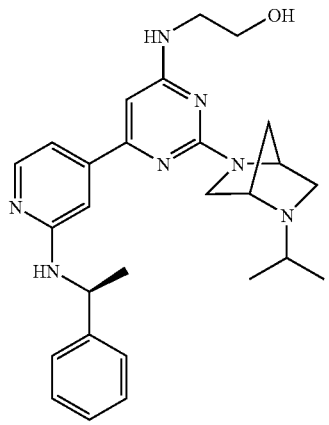

2-{2-(5-Isopropyl-(1S,4S)-2,5-diaza-bicyclo[2.2.1]
hept-2-yl)-6-[2-(S)-(1-phenyl-ethylamino)-pyridin-4-
yl]-pyrimidin-4-ylamino}-ethanol Step A: To a 250 mL RBF was added 4-chloro-6-(2-chloro-pyridin-4-yl)-2-methylsulfanyl-pyrimidine (0.54 g, 2.0 mmol), 50 mL CH₃CN, 2-aminoethanol (0.24 mL, 4.0 mmol), K₂CO₃ (0.27 g, 2.0 mmol). The mixture was refluxed under nitrogen for 4 h, and all starting material was converted. The reaction mixture was cooled down to rt, diluted with 200 mL ethyl acetate, washed with 50 mL sat. NaHCO₃, and dried over anhydrous Na₂SO₄. After purification by flash chromatograph, the intermediate 2-[6-(2-chloro-pyridin-4-yl)-2-methylsulfanyl-pyrimidin-4-ylamino]-ethanol was obtained. MS (ES+): 297 (M+H)⁺.

Step B: A mixture of 0.47 g (1.58 mmol) 2-[6-(2-chloro-pyridin-4-yl)-2-methylsulfanyl-pyrimidin-4-ylamino]-ethanol in 3 mL DMF was stirred at 0° C. under nitrogen. The mixture was treated with 0.45 mL (1.74 mmol) TBDP-SCI and stirred at 0° C. to rt for 15 h. The mixture was diluted with 100 mL ethyl acetate, washed with H₂O 3×50 mL, brine 20 mL, dried over anhydrous Na₂SO₄. After purification by flash chromatograph, the intermediate [2-(tert-butyl-diphenyl-silanyloxy)-ethyl]-[6-(2-chloro-pyridin-4-yl)-2-methylsulfanyl-pyrimidin-4-yl]-amine was obtained. MS (ES+): 535 (M+H)⁺.

Step C: A mixture of 0.73 g (1.36 mmol) 2-(tert-butyl-diphenyl-silanyloxy)-ethyl]-[6-(2-chloro-pyridin-4-yl)-2-methylsulfanyl-pyrimidin-4-yl]-amine in 20 mL THF was treated with 0.5 g (0.82 mmol) Oxone and 41 mg (0.136 mmol) tetrabutyl-ammonium nitrate in 4 mL H₂O at 0° C. The mixture was stirred at 0° C. for 4 h, all starting material was converted. The reaction mixture was treated with 10 mL sat. Na₂S₂O₃, extracted with DCM 3×50 mL, and dried with anhydrous Na₂SO₄. After purification by flash chromatograph, the intermediate [2-(tert-butyl-diphenyl-silanyloxy)-ethyl]-[6-(2-chloro-pyridin-4-yl)-2-methanesulfinyl-pyrimidin-4-yl]-amine was obtained. MS (ES+): 551 (M+H)⁺.

Step D: To a 100 mL RBF was added [2-(tert-butyl-diphenyl-silanyloxy)-ethyl]-[6-(2-chloro-pyridin-4-yl)-2-methanesulfinyl-pyrimidin-4-yl]-amine (0.5 g, 0.91 mmol), 10 mL DMF, (S)-2-isopropyl-2,5-diaza-bicyclo[2.2.1]heptane hydrochloride salt (0.23 g, 1.1 mmol), K₂CO₃ (0.313 g, 2.28 mmol). The mixture was stirred at 100° C. under nitrogen for 15 h, and all starting material was converted. The reaction mixture was cooled down to rt, diluted with 100 m]L DCM, washed with 50 mL sat. NaHCO₃, H₂O 3×50 mL, brine 20 mL, and dried over anhydrous Na₂SO₄. After purification by flash chromatograph, the intermediate [2-(tert-butyl-diphenyl-silanyloxy)-ethyl]-[6-(2-chloro-pyridin-4-yl)-2-(5-isopropyl-2,5-diaza-bicyclo[2.2.1]hept-2-yl)-pyrimidin-4-yl]-amine was obtained. MS (ES+): 627 (M+H)⁺.

Step E: To a 100 mL round bottom flask, was added [2-(tert-butyl-diphenyl-silanyloxy)-ethyl]-[6-(2-chloro-pyridin-4-yl)-2-(5-isopropyl-2,5-diaza-bicyclo[2.2.1]hept-2-yl)-pyrimidin-4-yl]-amine (0.35 g, 0.6 mmol), 50 mL toluene, and (S)-α-methylbenzylamine (0.11 mL, 0.84 mmol). The mixture was degassed by nitrogen bubbled through for 1 h. After Pd(OAc)₂ (14 mg, 0.06 mmol), BINAP (37 mg, 0.06 mmol) and NaOtBu (0.12 g, 1.2 mmol) were added, the mixture was warmed up to 90° C. and stirred for 2 h under nitrogen. The mixture was cooled down to rt, diluted with 100 mL DCM, washed with 20 mL sat. NaHCO₃, and dried over anhydrous Na₂SO₄. After purification by flash chromatography, obtained intermediate [2-(tert-butyl-diphenyl-silanyloxy)-ethyl]-{2-(5-isopropyl-2,5-diaza-bicyclo[2.2.1]hept-2-yl)-6-[2-(1-phenyl-ethylamino)-pyridin-4-yl]-pyrimidin-4-yl}-amine as a pale yellow solid. MS (ES+): 712 (M+H)⁺.

Step F: [2-(tert-Butyl-diphenyl-silanyloxy)-ethyl]-{2-(5-isopropyl-2,5-diaza-bicyclo[2.2.1]hept-2-yl)-6-[2-(1-phenyl-ethylamino)-pyridin-4-yl]-pyrimidin-4-yl}-amine (0.15 g, 0.2 mmol) in 10 mL THF was stirred at 0° C. under nitrogen and was treated with 0.32 mL (0.32 mmol) TBAF (1.0 M in THF), and stirred for 1 h. The mixture was quenched with 20 mL sat. NH₄Cl, extracted with DCM 3×50 mL. The combined organic was dried over anhydrous Na₂SO₄. After purification by flash chromatography, obtained the title compound as a pale yellow solid. MS (ES+): 474 (M+H)⁺.

EXAMPLE 27

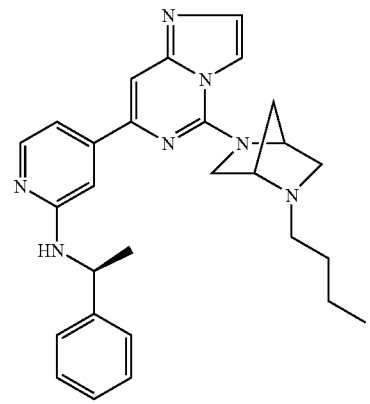

(S)-{4-[5-(5-n-Butyl-(1S,4S)-2,5-diaza-bicyclo
[2.2.1]hept-2-yl)-imidazo[1,2-c]pyrimidin-7-yl]-
pyridin-2-yl}-(1-phenyl-ethyl)-amine A solution of 25 mg (0.061 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 1 mL chloroform was treated with 0.011 mL (0.12 mmol) butyraldehyde and 26 mg (0.12 mmol) NaBH₃(CN) before 1 mL methanol was consequently added. The mixture was stirred at ambient temperature for 15 h when MS showed that all starting materials had converted to product. The reaction mixture was diluted with 20 mL DCM, washed with 20 mL satd. NaHCO$_3$, and dried over anhydrous Na$_2$SO$_4$. After purification by chromatography, the title compound was obtained. MS (ES+): 468 (M+H)$^+$.

EXAMPLE 28

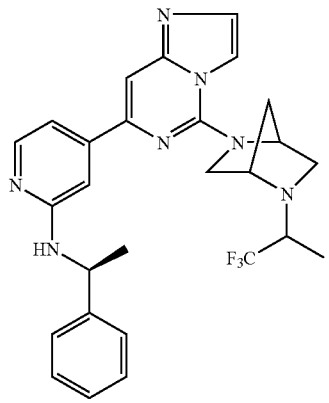

(S)-{4-[5-(5-(2,2,2-Trifluoro-1-methyl-ethyl)-(1S, 4S)-2,5-diaza-bicyclo[2.2.1]hept-2-yl)-imidazo[1,2-c]pyrimidin-7-yl]-pyridin-2-yl}-(1-phenyl-ethyl)-amine A solution of 40 mg (0.098 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 1 mL chloroform was treated with 1 mL (large excess) trifluoracetone and 62 mg (0.29 mmol) NaBH$_3$(CN), followed by addition of 1 mL methanol. The mixture was stirred at ambient temperature for 15 h when it was quenched before complete conversion to product. The reaction mixture was diluted with 20 mL DCM, washed with 20 mL satd. NaHCO$_3$, and dried over anhydrous Na$_2$SO$_4$. After purification by chromatography, the title compound was obtained as a mixture of diasteriomers (9:1 by HPLC). MS (ES+): 508 (M+H)$^+$.

EXAMPLE 29

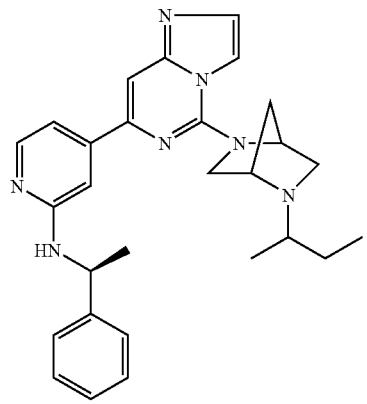

(S)-{4-[5-(5-sec-Butyl-(1S,4S)-2,5-diaza-bicyclo[2.2.1]hept-2-yl)-imidazo[1,2c]pyrimidin-7-yl]-pyridin-2-yl}-(1-phenyl-ethyl)-amine A solution of 130 mg (0.32 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 3 mL chloroform was treated with 0.29 mL (3.2 mmol) 2-butanone and 210 mg (1.0 mmol) NaBH$_3$(CN), followed by the addition of 5 mL methanol. The mixture was stirred at ambient temperature for 3 h when MS showed that all starting materials had converted to product. The reaction mixture was diluted with 50 mL DCM, washed with 50 mL satd. NaHCO$_3$, and dried over anhydrous Na$_2$SO$_4$. After purification by HPLC, the title compound was obtained. MS (ES+): 468 (M+H)$^+$.

EXAMPLE 30

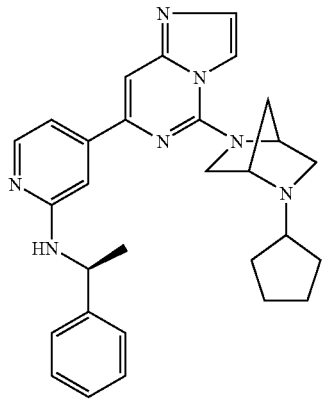

(S)-{4-[5-(5-Cyclopentyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine A solution of 120 mg (0.28 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 3 mL chloroform was treated with 0.25 mL (2.8 mmol) cyclopentanone and 180 mg (0.84 mmol) NaBH$_3$(CN), followed by addition of 5 mL methanol. The mixture was stirred at ambient temperature for 3 h when MS showed that all starting materials had converted to product. The reaction mixture was diluted with 50 mL DCM, washed with 50 mL satd. NaHCO$_3$, and dried over anhydrous Na$_2$SO$_4$. After purification by HPLC, the title compound was obtained. MS (ES+): 480 (M+H)$^+$.

EXAMPLE 31

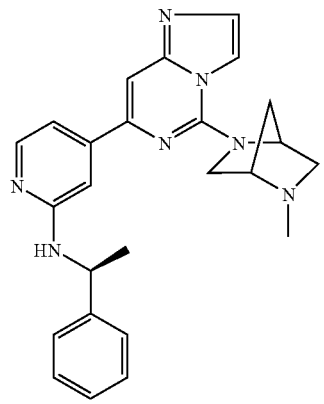

(S)-{4-[5-(5-Methyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine A solution of 96 mg (0.23 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 3 mL methanol was treated with 0.17 mL (2.3 mmol) formaldehyde (37% in water) and 150 mg (0.70 mmol) NaBH$_3$(CN). The mixture was stirred at ambient temperature for 1 h when MS showed that all starting materials had converted to product. The reaction mixture was diluted with 50 mL DCM, washed with 50 mL satd. NaHCO$_3$, and dried over anhydrous Na$_2$SO$_4$. After purification by HPLC, the title compound was obtained. MS (ES+): 426 (M+H)$^+$.

EXAMPLE 32

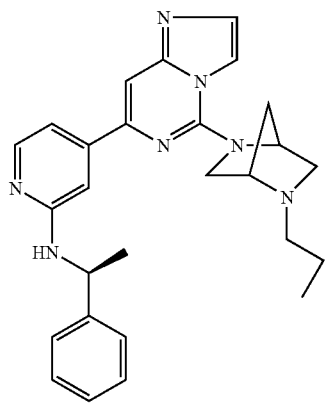

(S)-{4-[5-(5-Propyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine A solution of 113 mg (0.27 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 2.5 mL chloroform was treated with 0.20 mL (2.7 mmol) propionaldehyde and 180 mg (0.82 mmol) NaBH$_3$(CN), followed by addition of 2.5 mL methanol. The mixture was stirred at ambient temperature for 1 h when MS showed that all starting materials had converted to product. The reaction mixture was diluted with 50 mL DCM, washed with 50 mL satd. NaHCO$_3$, and dried over anhydrous Na$_2$SO$_4$. After purification by HPLC, the title compound was obtained. MS (ES+): 454 (M+H)$^+$.

EXAMPLE 33

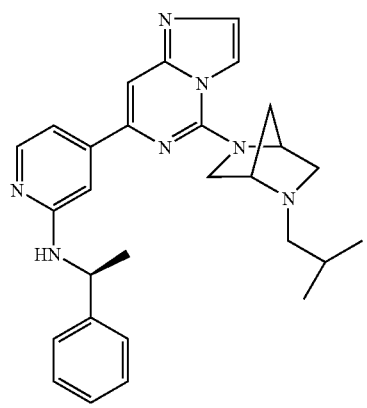

(S)-{4-[5-(5-Isobutyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine A solution of 110 mg (0.26 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 2.5 mL chloroform was treated with 0.24 mL (2.6 mmol) isobutyraldehyde and 170 mg (0.78 mmol) NaBH$_3$(CN), followed by the addition of 2.5 mL methanol. The mixture was stirred at ambient temperature for 1 h when MS showed that all starting materials had converted to product. The reaction mixture was diluted with 50 mL DCM, washed with 50 mL satd. NaHCO$_3$, and dried over anhydrous Na$_2$SO$_4$. After purification by HPLC, the title compound was obtained. MS (ES+): 468 (M+H)$^+$.

EXAMPLE 34

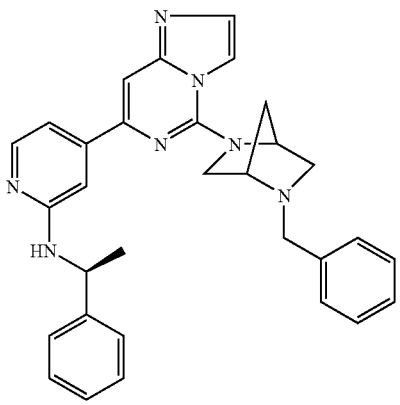

(S)-{4-[5-(5-Benzyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine A solution of 100 mg (0.24 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 2.5 mL chloroform was treated with 0.25 mL (2.4 mmol) benzaldehyde and 160 mg (0.73 mmol) NaBH$_3$(CN), followed by the addition of 2.5 mL methanol. The mixture was stirred at ambient temperature for 5 min when MS showed that all starting materials had converted to product. The reaction mixture was diluted with 50 mL DCM, washed with 50 mL satd. NaHCO$_3$, and dried over anhydrous Na$_2$SO$_4$. After purification by HPLC, the title compound was obtained. MS (ES+): 502 (M+H)$^+$.

EXAMPLE 35

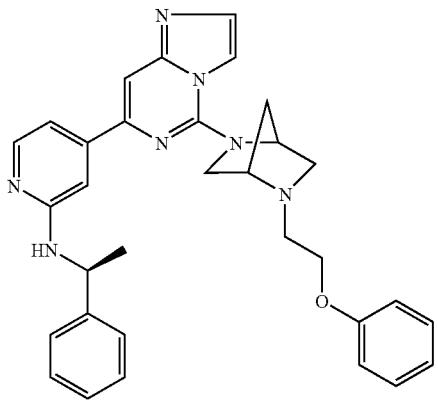

(S)-{4-[5-(5-(2-Phenoxy-ethyl)-(1S,4S)-2,5-diaza-bicyclo[2.2.1]hept-2-yl)-imidazo [1,2-c]pyrimidin-7-yl]-pyridin-2-yl}-(1-phenyl-ethyl)-amine A solution of 100 mg (0.24 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine and 70 mg (0.48 mmol) potassium carbonate in 5 mL acetonitrile was treated with 0.074 mL (0.48 mmol) β-bromophenetole at 0° C. The mixture was stirred at 50° C. for 8 h before it was cooled to ambient temperature for 16 h at which time MS showed that all starting materials had converted to product. The reaction mixture was diluted with 50 mL DCM, washed with 50 mL satd. NaHCO$_3$, and dried over anhydrous Na$_2$SO$_4$. After purification by chromotography, the title compound was obtained. MS (ES+): 532 (M+H)$^+$.

EXAMPLE 36

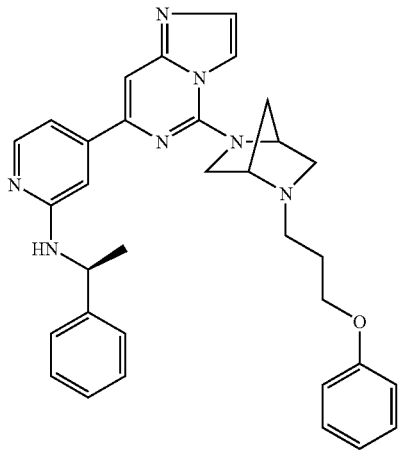

(S)-{4-[5-(5-(2-Phenoxy-propyl)-(1S,4S)-2,5-diaza-bicyclo[2.2.1]hept-2-yl)-imidazo[1,2-c]pyrimidin-7-yl]-pyridin-2-yl}-(1-phenyl-ethyl)-amine A solution of 50 mg (0.12 mmol) {4-[5-(2,5-diaza-bicyclo [2.2. I]hept-2-yl)-imidazo[1,2-c]pyrimidin-7-yl]-pyridin-2-yl}-(1-phenyl-ethyl)-amine and 30 mg (0.24 mmol) potassium carbonate in 2 mL acetonitrile was treated with 0.040 mL (0.24 mmol) 3-phenoxy-propyl bromide at 0° C. The mixture was stirred at 50° C. for 16 h at which time MS showed that all starting materials had converted to product. The reaction mixture was cooled to ambient temperature, diluted with 50 mL DCM, washed with 50 mL satd. NaHCO$_3$, and dried over anhydrous Na$_2$SO$_4$. After purification by BPLC, the title compound was obtained. MS (ES+): 546 (M+H)$^+$.

EXAMPLE 37

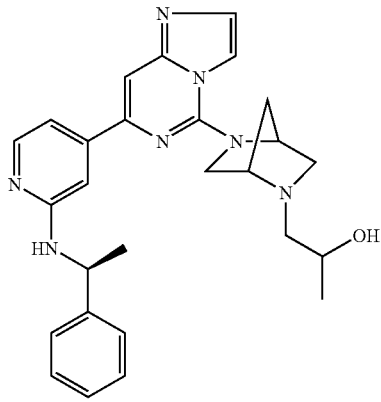

(S)-{4-[5-(5-(2-Phenoxy-propyl)-(1S,4S)-2,5-diaza-bicyclo[2.2.1]hept-2-yl)-imidazo[1,2-c]pyrimidin-7-yl]-pyridin-2-yl}-(1-phenyl-ethyl)-amine A solution of 100 mg (0.25 mmol) {4-[5-(2,5-diaza-bicyclo[2.2.1]hept-2-yl)-imidazo[1,2-c]pyrimidin-7-yl]-pyridin-2-yl}-(1-phenyl-ethyl)-amine in 20 mL methanol was treated with 5 mL (excess) propylene oxide at 0° C. The mixture was stirred at ambient temperature for 16 h at which time MS showed that all starting materials had converted to product. The reaction mixture was cooled to ambient temperature and was concentrated in vacuum. After purification by chromatography, the title compound was obtained. MS (ES+): 470 (M+H)$^+$.

EXAMPLE 38

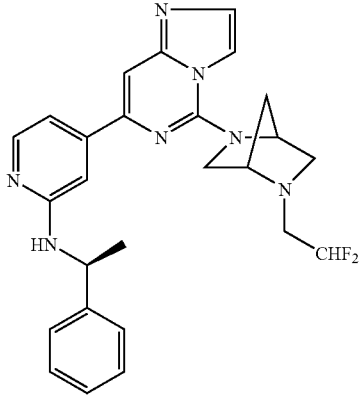

(S)-(4-{5-[5-(2,2-Difluoro-ethyl)-(1S,4S)-2,5-diaza-bicyclo[2.2.1]hept-2-yl]imidazo[1,2-c]pyrimidin-7-yl}-pyridin-4-yl)-(1-phenyl-ethyl)-amine Step A: 7-(2-Chloro-pyridin-4-yl)-5-[5-(2,2-difluoro-ethyl)-2,5-diaza-bicyclo[2.2.1]-hept-2-yl]-imidazo[1,2-c]pyrimidine To an RBF was added 5-chloro-7-(2-chloro-pyridin-4-yl)-imidazo[1,2-c]pyrimidine (54 mg, 0.17 mmol), trifluoromethanesulfonic acid 2,2-difluoroethyl ester (32 mg, 0.18 mmol), K$_2$CO$_3$ (27 mg, 0.20 mmol), and 5 mL acetonitrile.

The mixture was stirred at reflux under nitrogen for 4 h, at which time no starting material was observed. The reaction mixture was cooled to ambient temperature, diluted with 50 mL DCM, washed with 50 mL satd. NaHCO$_3$, and dried over anhydrous Na$_2$SO$_4$. After purification by silica gel chromatography, the title compound was obtained.

MS (ES+): 391 (M+H)$^+$.

Step B: (4-{5-[5-(2,2-Difluoro-ethyl)-2,5-diaza-bicyclo[2.2.1]hept-2-yl]-imidazo[1,2-c]pyrimidin-7-yl}-pyridin-4-yl)-(1-phenyl-ethyl)-amine To an RBF was added 7-(2-chloro-pyridin-4-yl)-5-[5-(2,2-difluoro-ethyl)-2,5-diaza-bicyclo[2.2.1]hept-2-yl]-imidazo[1,2-c]pyrimidine (40 mg, 0.10 mmol), 1 mL toluene, and (S)-α-methylbenzylamine (0.015 mL, 0.11 mmol). The mixture was degassed by bubbling nitrogen through solution for 1 h. After Pd(OAc)$_2$ (2 mg, 0.01 mmol), rac-BINAP (6 mg, 0.01 mmol), and NaOtBu (0.20 mg, 0.21 mmol) were added, the mixture was warmed up to 90° C. and stirred for 3 h under nitrogen. The mixture was cooled down to ambient temperature, diluted with 50 mL DCM, washed with 20 mL sat. NaHCO$_3$, and dried over anhydrous Na$_2$SO$_4$. After purification by preparatory TLC, the title compound was obtained. MS (ES+): 476 (M+H)$^+$.

EXAMPLE 39

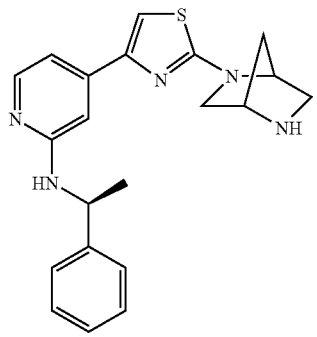

(S)-{4-[2-((1S,4S)-2,5-Diaza-bicyclo[2.2.1]hept-2-yl)-thiazol-4-yl]-pyridin-2-yl}-(1-phenyl-ethyl)-amine Step A: To a 250 mL RBF, was added 2-chloro-isonicotinic acid (7.9 g, 50 mmol), 100 mL DCM. The above mixture was cooled down to 0° C. and treated with 8.7 mL (100 mmol) (COCl)$_2$ and 1 mL DMF. The mixture was warmed up and refluxed under nitrogen for 2 h. The mixture was cooled down to rt, all solvent was removed by vacuum. The residue was dissolved in CH$_3$CN/THF (1:1) 100 mL, cooled down to 0° C., and treated with TMSCH$_2$CN 2.0 M in hexane (38 mL, 75 mmol). The mixture was stirred at 0° C. to rt for 2 h, all solvent was removed by vacuum. The residue was dissolved in 100 mL DCM, cooled down to 0° C., and treated with 1N HCl in ether (100 mL, 100 mmol). The mixture was stirred at 0° C. to rt for 15 h. The mixture was poured on to 100 g ice, stirred for 30 min, extracted with DCM 3×50 mL. The combined organics was washed with brine 50 mL, and dried over anhydrous Na$_2$SO$_4$. After purification by flash chromatography, obtained 2-chloro-1-(2-chloro-pyridin-4-yl)-ethanone as a yellow solid. MS (ES+): 190 (M+H)$^+$.

Step B: The mixture of 3.75 mL (26.6 mmol) TMSisothiocyanate in 50 mL THF stirred under nitrogen was treated with 3.52 g (17.8 mmol) 2,5-diaza-bicyclo[2.2.1]-heptane-2-carboxylic acid tert-butyl ester. The mixture was stirred at rt for 15 h, then warmed up to 50° C. and stirred for 2 h. The mixture was cooled down to 0° C., quenched with 20 mL H$_2$O extracted with DCM 2×50 mL. The combined organics were washed with brine 50 mL, and dried over anhydrous Na$_2$SO$_4$. After purification by flash chromatography, 5-thiocarbamoyl-2,5-diaza-bicyclo[2.2.1]heptane-2-carboxylic acid tert-butyl ester was obtained as pale yellow solid. MS (ES+): 258 (M+H)$^+$.

Step C: A mixture of 0.19 g (1 mmol) 2-chloro-1-(2-chloro-pyridin-4-yl)-ethanone and 0.257 g (1 mmol) 5-thiocarbamoyl-2,5-diaza-bicyclo[2.2.1]heptane-2-carboxylic acid tert-butyl ester in 20 mL ethanol was refluxed under nitrogen in a sealed tube for 2 h. The mixture was cooled down to rt, all solvent was removed by vacuum. After purification by flash chromatography, 2-[4-(2-chloro-pyridin-4-yl)-thiazol-2-yl]-2,5-diaza-bicyclo[2.2.1]heptane was obtained as a pale yellow solid.

MS (ES+): 293 (M+H)$^+$. 5-[4-(2-chloro-pyridin-4-yl)-thiazol-2-yl]-2,5-diaza-bicyclo[2.2.1]heptane-2-carboxylic acid tert-butyl ester, MS (ES+): 393 (M+H)$^+$.

Step D: A mixture of 0.17 g (0.58 mmol) [4-(2-chloro-pyridin-4-yl)-thiazol-2-yl]-2,5-diaza-bicyclo[2.2.1]heptane-2-carboxylic acid tert-butyl ester and 0.089 mL (0.7 mmol) (S)-α-methylbenzylamine in 50 mL toluene was degassed by nitrogen bubbled through for 1 h. After Pd(OAc)$_2$ (13 mg, 0.058 mmol), BINAP (36 mg, 0.058 mmol) and NaOtBu (0.11 g, 1.16 mmol) were added, the mixture was warmed up to 90° C. and stirred for 2 h under nitrogen. The mixture was cooled down to rt, diluted with 100 mL DCM, washed with 20 mL sat. NaHCO$_3$, and dried over anhydrous Na$_2$SO$_4$. After purification by flash chromatography, obtained the title compound in 150 mg as a pale yellow solid. MS (ES+): 378 (M+H)$^+$.

EXAMPLE 40

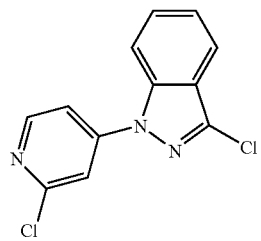

3-Chloro-1-(2-chloro-pyridin-4-yl)-1 H-indazole

To a solution of 3-chloroindazole (1 g, 6.6 mmol) in methylene chloride (25 mL) and methanol (25 mL) were added 2-chloro-4-(4,4,5,5-tetramethyl-[1,3,2]dioxaborolan-2-yl)pyridine (3.6 g, 15 mmol) and copper(II) acetate (1.4 g, 7.5 mmol), followed by triethylamine (2 mL, 15 mmol). The resulting mixture was vigorously stirred at room temperature for 20 h. The reaction was filtered and the gray solid was discarded. The blue filtrate was concentrated in vacuo and the residue was dissolved in methylene chloride and washed with saturated sodium bicarbonate and brine and dried over MgSO$_4$. Flash chromatography of the crude product mixture with 25:10:65 and 35:10:55 EtOAc-CH$_2$Cl$_2$-Hexane gave the title compound as a white solid. MS (ES+): 264.0 [M+H]+.

EXAMPLE 41

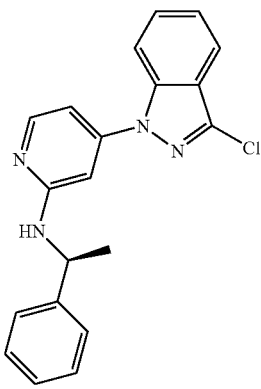

(S)-[4-(3-Chloro-indazol-1-yl)-pyridin-2-yl]-(1-phenyl-ethyl)-amine

To a solution of 3-chloro-1-(2-chloro-pyridin-4-yl)-1H-indazole (0.29 g, 1.1 mmol) in toluene (6 mL) under nitrogen were added palladium acetate (0.025 g, 0.11 mmol), rac-2,2'-bis(diphenylphosphino)-1,1'-binaphthyl (0.069 g, 0.1 mmol), and (S)-(−)-α-methylbenzylamine (0.18 mL, 1.38 mmol), followed by sodium t-butoxide (0.3 g, 3.1 mmol). The resulting mixture was heated at 70° C. for 1 h, during which TLC and HPLC indicated completion of reaction. After cooling to room temperature, the reaction was diluted with methylene chloride and washed with saturated sodium bicarbonate and brine and dried over MgSO$_4$. Flash chromatography of the crude product mixture with 25:10:65, 35:10:55, and 50:10:40 EtOAc-CH$_2$Cl$_2$-hexane gave the title compound as a tan colored solid. MS (ES+): 349.3 [M+H]+, 347.1 [M−H]−.

EXAMPLE 42

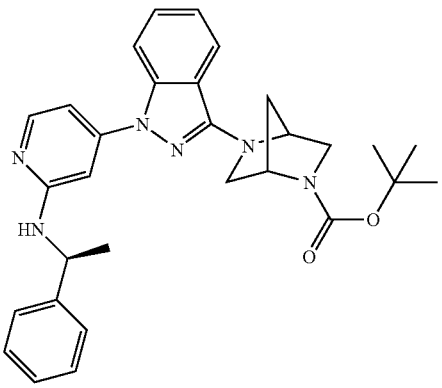

5-{1-[2-((S)-1-Phenyl-ethylamino)-pyridin-4-yl]-1H-indazol-3-yl}-(1S,4S)-2,5-diaza-bicyclo[2.2.1]heptane-2-carboxylic acid tert-butyl ester To a solution of [4-(3-chloro-indazol-1-yl)-pyridin-2-yl]-(1-phenyl-ethyl)-amine (0.17 g, 0.48 mmol) in toluene (3 mL) under nitrogen were added palladium acetate (0.011 g, 0.05 mmol), rac-2,2'-bis(diphenylphosphino)-1,1'-binaphthyl (0.03 g, 0.05 mmol), and t-butyl(1S,4S)-(−)-2,5-diazabicyclo[2.2.1]heptane-2-carboxylate (0.14 g, 0.72 mmol), followed by sodium t-butoxide (0.13 g, 1.3 mmol). The resulting mixture was stirred at 90° C. for 20 h. After cooling to room temperature, the reaction was diluted with methylene chloride and washed with saturated sodium bicarbonate and brine; dried (MgSO$_4$). Flash chromatography of the crude product mixture with 25:10:65, 40:10:50, 50:10:40, 60:10:30, and 70:10:20 EtOAc-CH$_2$Cl$_2$-Hexane gave the title compound. MS (ES+): 511.4 [M+H]+, 509.2 [M−H]−.

EXAMPLE 43

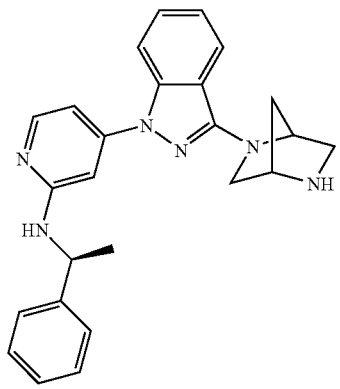

(S)-{4-[3-((1s, 4S)-2,5-Diaza-bicyclo[2.2.1]hept-2-yl)-indazol-1-yl]-pyridin-2-yl}-(1-phenyl-ethyl)-amine To the 5-{1-[2-(1-phenyl-ethylamino)-pyridin-4-yl]-1H-indazol-3-yl}-2,5-diaza-bicyclo[2.2.1]heptane-2-carboxylic acid tert-butyl ester (0.044 g, 0.086 mmol) were added 4N HCl in dioxane (1 mL) and a few drops of methanol. After stirring at room temperature for 30 min, the reaction was concentrated in vacuo and the residue was partitioned between methylene chloride and saturated sodium bicarbonate; the aqueous layer was back-extracted with methylene chloride (2×). The combined organic extract was dried (K$_2$CO$_3$), filtered, and concentrated in vacuo. Flash chromatography with 1%, 3%, and 5% 2M NH$_3$ in MeOH/CHCl$_3$ gave the title compound as a cream colored solid. MS (ES+): 411.3 [M+H]+, 409.5 [M−H]−.

EXAMPLE 44

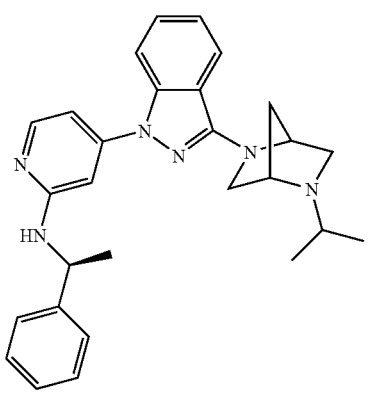

(S)-{4-[3-(5-Isopropyl-(1S,4S)-2,5-diaza-bicyclo[2.2.1]hept-2-yl)-indazol-1-yl]-pyridin-2-yl}-(1-phenyl-ethyl)-amine To a solution of {4-[3-(2,5-diaza-bicyclo[2.2.1]hept-2-yl)-indazol-1-yl]-pyridin-2-yl}-(1-phenyl-ethyl)-amine (0.03 g, 0.074 mmol) in chloroform (1 mL) were added acetone (0.5 mL) and sodium triacetoxyborohydride (0.039 g, 0.18 mmol) and the solution was stirred at 70° C. for 1 h. After cooling to room temperature, the reaction was diluted with methylene chloride and washed with saturated sodium bicarbonate. The aqueous layer was back-extracted with methylene chloride (2×). The combined organic extracts were dried ($K_2CO_3$), filtered, and concentrated in vacuo. Flash chromatography with 1%, 3%, and 5% 2M $NH_3$ in MeOH/$CHCl_3$ gave the title compound as an off-white glass. MS (ES+): 453.3 [M+H]+, 451.4 [M−H]−.

EXAMPLE 45

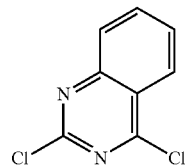

2,4-Dichloro-quinazoline

The title compound was synthesized by following the procedure described in J. Med. Chem. 1988, 31, 2136. MS (ES+): 199.2 [M+H]+.

EXAMPLE 46

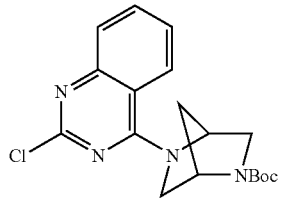

5-(2-Chloro-quinazolin-4-yl)-(1S,4S)-2,5-diaza-bicyclo[2.2.1]heptane-2-carboxylic acid tert-butyl ester To a solution of 2,4-dichloro-quinazoline (0.25 g, 1.26 mmol) in isoprapanol (6 mL) were added t-butyl-(1S,4S)-(−)-2,5-diazabicyclo[2.2.1]heptane-2-carboxylate (0.25 g, 1.26 mmol) and the solution was heated at 60° C. for 4 h. The reaction was concentrated in vacuo and the residue was chromatographed over silica with 25:10:65, 35:10:55, and 50:10:40 EtOAc-$CH_2Cl_2$-Hexane; 1%, 3%, and 5% MeOH/$CH_2Cl_2$ to give the title compound. MS (ES+): 361.1 [M+H]+.

EXAMPLE 47

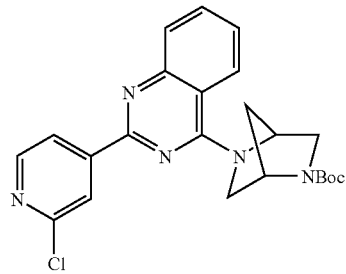

5-[2-(2-Chloro-pyridin-4-yl)-quinazolin-4-yl]-(1S,4S)-2,5-diaza-bicyclo[2.2.1]heptane-2-carboxylic acid tert-butyl ester A solution of 5-(2-chloro-quinazolin-4-yl)-2,5-diaza-bicyclo[2.2.1]heptane-2-carboxylic acid tert-butyl ester (0.145 g, 0.4 mmol) in DME (2 mL) under nitrogen were added palladium acetate (0.0045 g, 0.02 mmol), tri-o-tolylphosphine (0.015 g, 0.048 mmol), and 2-chloro-4-(4,4,5,5-tetramethyl-[1,3,2]dioxaborolan-2-yl)pyridine (0.19 g, 0.8 mmol), followed by 2M $Na_2CO_3$ (0.6 mL, 1.2 mmol). The resulting mixture was heated at 80° C. for 20 h. The reaction was diluted with methylene chloride and washed with saturated sodium bicarbonate and brine and dried ($MgSO_4$). Flash chromatography of the crude product mixture with 25:10:65, 35:10:55, and 50:10:40 EtOAc-$CH_2Cl_2$-Hexane gave the title compound. MS (ES+): 438.2 [M+H]+.

EXAMPLE 48

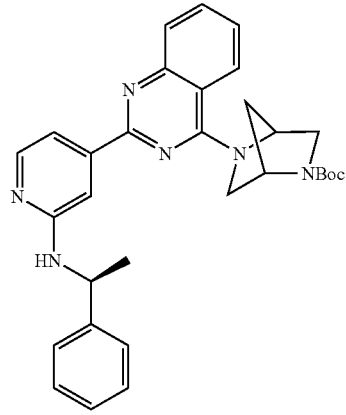

5-{2-[2--((S)-1-Phenyl-ethylamino)-pyridin-4-yl]-quinazolin-4-yl}-(1S,4S)-2,5-diaza-bicyclo[2.2.1]heptane-2-carboxylic acid tert-butyl ester The title compound was analogously synthesized by the procedure described in Example 2 from 5-[2-(2-chloro-pyridin-4-yl)-quinazolin-4-yl]-2,5-diaza-bicyclo[2.2.1]heptane-2-carboxylic acid tert-butyl ester. MS (ES+): 523.3 (M+H)+.

EXAMPLE 49

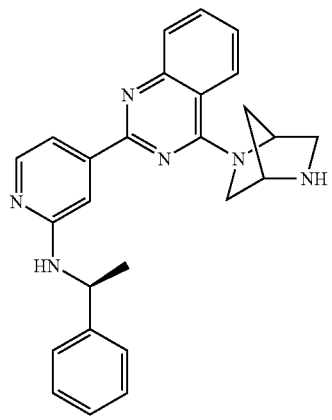

{4-[4-((1S,4S)-2,5-Diaza-bicyclo[2.2.1]hept-2-yl)-quinazolin-2-yl]-pyridin-2-yl}-(S)-(1-phenyl-ethyl)-amine The title compound was analogously synthesized by the procedure described in Example 4 from 5-{2-[2-(1-phenyl-ethylamino)-pyridin-4-yl]-quinazolin-4-yl}-2,5-diaza-bicyclo[2.2.1]heptane-2-carboxylic acid tert-butyl ester. MS (ES+): 423.3 (M+H)+.

EXAMPLE 50

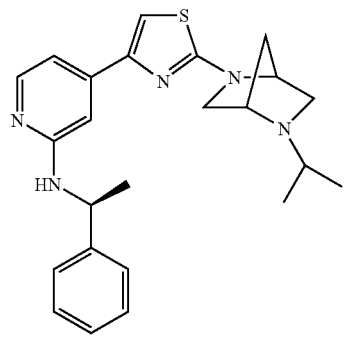

(S)-{4-[2-(5-Isopropyl-(1S,4S)-2,5-diaza-bicyclo [2.2.1]hept-2-yl)-thiazol-4-yl]-pyridin-2-yl}-(1-phenyl-ethyl)-amine A mixture of 75 mg (0.2 mmol) {4-[2-(2,5-diaza-bicyclo [2.2.1]hept-2-yl)-thiazol-4-yl]-pyridin-2-yl}-(1-phenyl-ethyl)-amine in 5 mL chloroform was treated with 0.15 mL (2mmol) acetone, 120 mg (2 mmol) NaBH₃(CN) and 1 mL methanol consequently. The mixture was stirred at rt for 15 h. MS showed all starting materials were converted. The mixture was diluted with 100 mL DCM, washed with 20 mL sat. NaHCO₃, dried over anhydrous Na₂SO₄. After purification by chromatography, obtained the title compound as a yellow solid. MS (ES+): 420 (M+H)+.

EXAMPLE 51

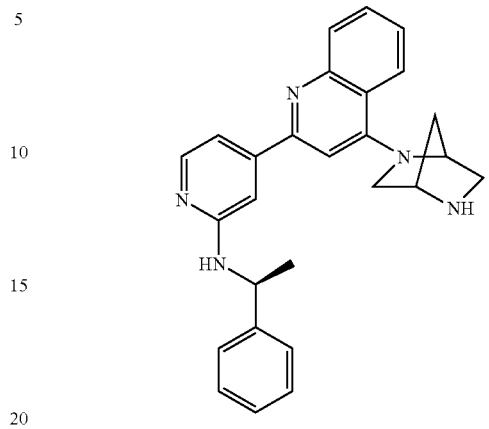

(S)-{4-[4-((1S,4S)-2,5-Diaza-bicyclo[2.2.1]hept-2-yl)-quinolin-2-yl]-pyridin-2-yl}-(1-phenyl-ethyl)-amine Step A: The mixture of 2-chloro-isonicotinic acid (16.8 g, 0.107 mol), 100 mL absolute ethanol and concentrate H₂SO₄ (3.28 mL, 0.118 mol) was refluxed under nitrogen for 15 h. After all starting material converted, the mixture was cool down to rt, and vacuumed down all ethanol. The resulted mixture was diluted with 250 mL ethyl acetate, washed with sat. NaHCO₃, dried over anhydrous Na₂SO₄. Purified by a short column, the 2-chloro-isonicotinic acid ethyl ester was obtained in as a pale yellow liquid. MS (ES+): 186 (M+H)+.

Step B: A mixture of 15 g 2-chloro-isonicotinic acid ethyl ester (81.4 mmol), and 8.75 mL ethyl acetate (88 mmol) in 200 mL anhydrous THF was stirred at 0° C. under nitrogen. The mixture was treated with 100 mL LHMS (1.0 M in THF) in 30 min. The resulted mixture was stirred at 0° C.—rt for 15 h, then quenched with 200 mL sat. NH₄Cl at 0° C. and adjusted pH 6-7. The water layer was extracted with ethyl acetate 3×50 mL. The combined organic was dried over anhydrous Na₂SO₄, and purified by column chromatography. 3-(2-chloro-pyridin-4-yl)-3-oxo-propionic acid ethyl ester was obtained as a pale yellow solid. MS (ES+): 228 (M+H)+.

Step C: A mixture 2.2 mL (24.18 mmol) aniline, 5.49 g (24.18 mmol) 3-(2-chloro-pyridin-4-yl)-3-oxo-propionic acid ethyl ester and 0.36 g (2.4 mmol) TsOH in 100 mL toluene was refluxed with a Dean-Stark trap for 8 h. 10 mL diphenyl ether was added and heated to 180° C. for 2 h. MS showed all starting material was converted to the desired product. The mixture was cooled down to rt, and a pink solid precipitated. The solid was filtrated and washed with hexane, and obtained as a brown solid 2-(2-chloro-pyridin-4-yl)-quinolin-4-ol, MS (ES+): 257 (M+H)+.

Step D: To a 250 mL RBF was added 4.6 g (18 mmol) 2-(2-chloro-pyridin-4-yl)-quinolin-4-ol and 100 mL POCl₃, and the mixture was treated with 3.1 mL DIEA (18 mmol). The mixture was was stirred at rt for 1 h, and all starting material was converted. All POCl₃ was vacuumed down. The residue was dissolved in 250 mL DCM, washed with saturated NaHCO₃ carefully to pH 8. The organic phase was dried over Na₂SO₄, concentrated and purified by column and yielded pale yellow 4-chloro-2-(2-chloro-pyridin-4-yl)-quinoline. MS (ES+): 275 (M+H)+.

Step E: To a 100 mL RBF was added 1.54 g (5.6 mmol) 4-chloro-2-(2-chloro-pyridin-4-yl)-quinoline1.22 g (6.16 mmol) (S)-N-Boc-2,5-diaza-bicyclo[2.2.1]heptane, 0.77 g (5.6 mmol) $K_2CO_3$ and 20 mL DMF. The mixture was refluxed under nitrogen for 15 h, and all starting material was converted. The reaction mixture was added to 300 mL ethyl acetate and washed with $H_2O$ 3×50 mL, brine (50 mL), dried over $Na_2SO_4$, concentrated and purified by column, giving pale yellow 5-[2-(2-chloro-pyridin-4-yl)-quinolin-4-yl]-2,5-diaza-bicyclo[2.2.1]heptane-2-carboxylic acid tert-butyl ester. MS (ES+): 437 (M+H)$^+$.

Step F: To a 250 mL RBF, was added 0.6 g (1.38 mmol) 5-[2-(2-chloro-pyridin-4-yl)-quinolin-4-yl]-2,5-diaza-bicyclo[2.2.1]heptane-2-carboxylic acid tert-butyl ester, 100 mL toluene, and 0.21 mL (1.65 mmol) (S)-α-methylbenzylamine. The mixture was degassed by nitrogen bubbled through for 1 h. After $Pd(OAc)_2$ (15 mg, 0.069 mmol), BINAP (43 mg, 0.069 mmol) and NaOtBu (0.265 g, 2.76 mmol) were added, the mixture was warmed up to 90° C. and stirred for 2 h under nitrogen. The mixture was cooled down to rt, diluted with 300 mL DCM, washed with 20 mL sat. $NaHCO_3$, and dried over anhydrous $Na_2SO_4$. After purification by flash chromatography, 5-{2-[2-(1-phenyl-ethylamino)-pyridin-4-yl]-quinolin-4-yl}-2,5-diaza-bicyclo[2.2.1]heptane-2-carboxylic acid tert-butyl ester was obtained as a pale yellow solid. MS (ES+): 522 (M+H)$^+$.

Step G: To a 50 mL RBF was added 0.35 g (0.67 mmol) 5-{2-[2-(1-phenyl-ethylamino)-pyridin-4-yl]-quinolin-4-yl}-2,5-diaza-bicyclo[2.2.1]heptane-2-carboxylic acid tert-butyl ester, 5 mL methanol and stirred at rt under nitrogen. The mixture was treated with and 2.5 mL 4N HCl in dioxane and was stirred at rt for 1 h. The mixture was diluted with 100 mL DCM, washed with 20 mL sat. $NaHCO_3$, and dried over anhydrous $Na_2SO_4$. After purification by flash chromatography, the title compound was obtained as a pale yellow solid. MS (ES+): 422 (M+H)$^+$.

EXAMPLE 52

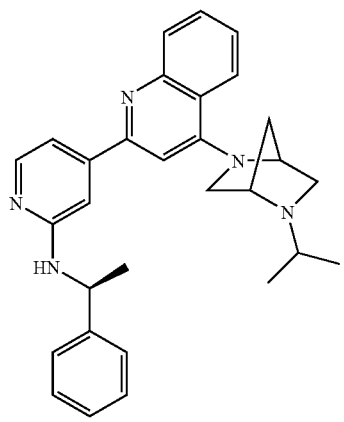

(S)-{4-[4-(5-Isopropyl-(1S,4S)-2,5-diaza-bicyclo[2.2.1]hept-2-yl)-quinolin-2-yl]-pyridin-2-yl}-(1-phenyl-ethyl)-amine A mixture of 60 mg (0.14 mmol) {4-[4-(2,5-diaza-bicyclo[2.2.1]hept-2-yl)-quinolin-2-yl]-pyridin-2-yl}-(1-phenyl-ethyl)-amine in 5 mL chloroform was treated with 0.15 mL (2mmol) acetone, 120 mg (2 mmol) $NaBH_3(CN)$ and 1 mL methanol. The mixture was stirred at rt for 15 h. MS showed all starting materials were converted. The mixture was diluted with 100 mL DCM, washed with 20 mL sat. $NaHCO_3$, dried over anhydrous $Na_2SO_4$. After purification by flash chromatography, the title compound was obtained as a yellow solid. MS (ES+): 464 (M+H)$^+$.

EXAMPLE 53

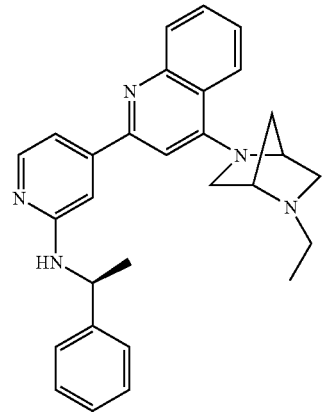

(S)-{4-[4-(5-Ethyl-(1S,4S)-2,5-diaza-bicyclo[2.2.1]hept-2-yl)-quinolin-2-yl]-pyridin-2-yl}-(1-phenyl-ethyl)-amine A mixture of 60 mg (0.14 mmol) {4-[4-(2,5-diaza-bicyclo[2.2.1]hept-2-yl)-quinolin-2-yl]-pyridin-2-yl}-(1-phenyl-ethyl)-amine in 5 mL chloroform was treated with 0.1 mL (1.8 mmol) acetaldehyde, 113 mg (1.8 mmol) $NaBH_3(CN)$ and 1 mL methanol. The mixture was stirred at rt for 15 h. MS showed all starting materials were converted. The mixture was diluted with 100 mL DCM, washed with 20 mL sat. $NaHCO_3$, and dried over anhydrous $Na_2SO_4$. After purification by chromatography, the title compound was obtained as a yellow solid. MS (ES+): 450 (M+H)$^+$.

EXAMPLE 54

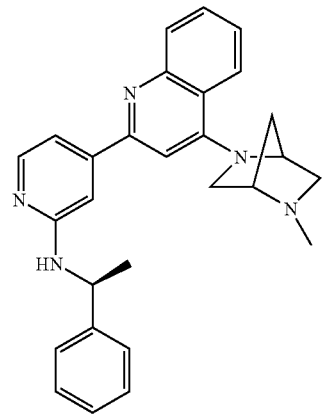

(S)-{4-[4-(5-Methyl-(1S,4S)-2,5-diaza-bicyclo[2.2.1]hept-2-yl)-quinolin-2-yl]-pyridin-2-yl}-(1-phenyl-ethyl)-amine A mixture of 60 mg (0.14 immol) {4-[4-(2,5-diaza-bicyclo[2.2.1]hept-2-yl)-quinolin-2-yl]-pyridin-2-yl}-(1-phenyl-ethyl)-amine in 5 mL chloroform was treated with 0.11 mL (1.42 mmol) formaldehyde 37% water solution, 113 mg (1.8 mmol) NaBH$_3$(CN) and 1 mL methanol. The mixture was stirred at rt for 15 h. MS showed all starting materials were converted. The mixture was diluted with 100 mL DCM, washed with 20 mL sat. NaHCO$_3$, dried over anhydrous Na$_2$SO$_4$. After purification by chromatography, the title compound was obtained as a yellow solid. MS (ES+): 436 (M+H)$^+$.

EXAMPLE 55

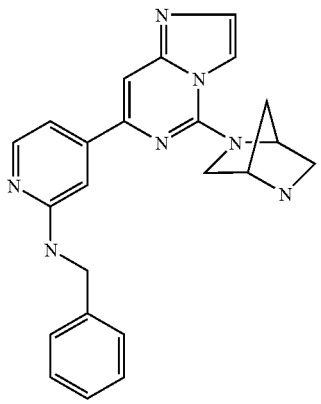

Benzyl-(4-[5-((1S,4S)-2-5-diaza-bicyclo[2,2,1]hept-2-yl)-imidazo[1,2-c]pyrimidin-7-yl]-pyridin-2-yl)-amine Step A: 5-[7-(2-Chloro-pyridin-4-yl)-imidazo[1,2-c]pyrimidin-5-yl]-2,5-diaza-bicyclo[2.2.1]heptane-2-carboxylic acid tert-butyl ester To a solution of 5-chloro-7-(2-chloropyridin-4-yl)-imidazo[1,2-c]pyrimidine (3.615 g) in NMP was added 2,5-diaza-bicyclo[2.2.1]heptane-2-carboxylic acid tert-butyl ester (3 g) followed by potassium carbonate (9.4 g). The reaction mixture was stirred at room temperature for overnight. The crude reaction mixture was worked up to give desired product as an off-while solid. MS (ES+): 497 (M+H)$^+$.

Step B: 5-[7-(2-Benzylaminopyridin-4-yl)-imidazo[1,2-c]pyrimidin-5-yl]-2,5-diaza-bicyclo[2.2.1]heptane-2-carboxylic acid tert-butyl ester To a solution of 5-[7-(2-chloropyridin-4-yl)imidazo[1,2-c]pyrimidin-5-yl]-2,5-diaza-bicyclo[2.2.1]heptane-2-carboxylic acid tert-butyl ester (1.0 g) in toluene was added benzylamine (0.28 g), palladium acetate (0.016 g), BINAP (0.044 g), and sodium tert-butoxide (0.630 g). The reaction mixture was stirred at 70° C. under N$_2$ for 2 h. The reaction mixture was cooled down to room temperature then filtered over a bed of celite and chromatagraphed to give the desired product as light yellow solid. MS (ES+): 143 (M+H)$^+$.

Step C: Benzyl-(4-[5-(2,5-diaza-bicyclo[2.2.1]hept-2-yl)-imidazo[1,2-c]pyrimidin-7-yl]-pyridin-2-yl)-amine To a solution of 5-[7-(2-benzylaminopyridin-4-yl)imidazo[1,2-c]pyrimidin-5-yl]-2,5-diazabicyclo[2.2.1]heptane-2-carboxylic acid tert-butyl ester (0.207 g) was added MeOH (2 mL) followed by 4N HCL in 1,4-dioxane (5 mL) at room temperature. After 30 min, work up between dichloromethane and sodium bicarbonate followed by flash column purification afforded the title compound as an off white solid. MS (ES+): 398 (M+H)$^+$; (ES−): 396 (M−H)$^-$.

EXAMPLE 56

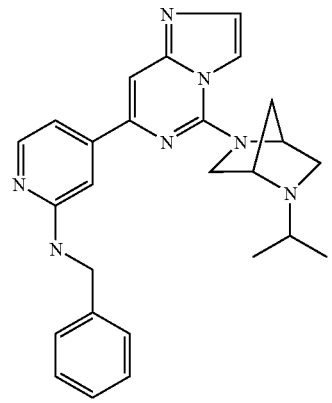

Benzyl-{4-[5-(5-isopropyl-(1S,4S)-2,5-diaza-bicyclo[2.2.1]hept-2-yl)-imidazo[1,2-c]pyrimidin-7-yl]-pyridin-2-yl}-amine Step D: Benzyl-{4-[5-(5-isopropyl-2,5-diaza-bicyclo[2.2.1]hept-2-yl)-imidazo[1,2-c]pyrimidin-7-yl]-pyridin-2-yl}-amine The title compound was analogously synthesized by the method described in Example 55 with the addition of one step. To a solution of benzyl-(4-[5-(2,5-diaza-bicyclo[2.2.1]hept-2-yl)imidazo[1,2-c]pyrimidin-7-yl]pyridin-2-yl)amine (0.400 g) was added chloroform (4 mL) followed by acetone (5 mL), and sodium triacetoxy borohydride (0.600 mg) at 70° C. After 30 min, work up between dichloromethane and sodium bicarbonate followed by flash column purification afforded the title compound as an off white solid. MS (ES+): 440 (M+H)$^+$; (ES−): 438(M−H)$^-$.

EXAMPLE 57

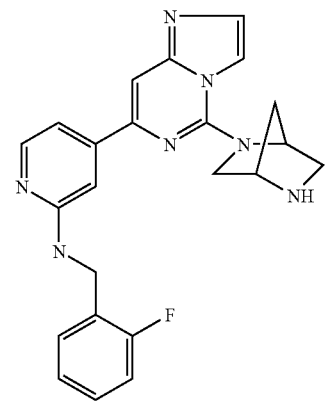

{4-[5-((1S,4S)-2,5-Diaza-bicyclo[2.2.1]hept-2-yl)-imidazo[1,2-c]pyrimidin-7-yl]-pyridin-2-yl}-(2-fluoro-benzyl)-amine The title compound was analogously synthesized by the method described in Example 1, except that 2-fluorobenzylamine, instead of benzylamine, was used. MS (ES+): 416 (M+H)⁺; (ES−): 414 (M−H)⁻.

EXAMPLE 58

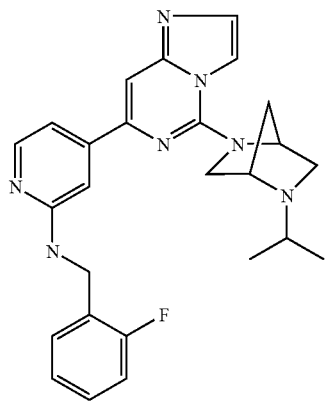

(2-Fluoro-benzyl)-{4-[5-(5-isopropyl-(1S,4S)-2,5-diaza-bicyclo[2.2.1]hept-2-yl)-imidazo[1,2-c]pyrimidin-7-yl]-pyridin-2-yl}-amine The title compound was analogously synthesized by the method described in Example 2, except that 2-fluorobenzylamine, instead of benzylamine was used. MS (ES+): 458 (M+H)⁺; (ES−): 456 (M−H)⁻.

EXAMPLE 59

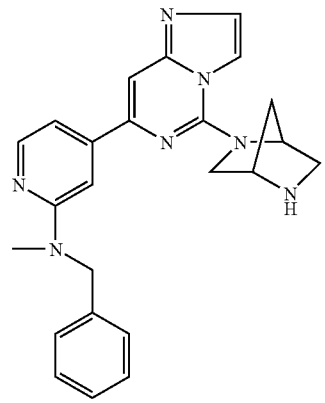

Benzyl {4-[5-((1S,4S)-2,5-diazabicyclo[2.2.1]hept-2-yl)imidazo[1,2-c]pyrimidin-7-yl]pyridin-2-yl}methylamine The title compound was analogously synthesized by the method described in Example 1, except that benzylmethylamine, instead of benzylamine, was used. MS (ES+): 412 (M+H)⁺; (ES−): 410(M−H)⁻.

EXAMPLE 60

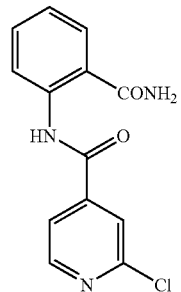

N-(2-Carbamoyl-phenyl)-2-chloro-isonicotinamide

To a solution of anthranilamide (2.36 g, 17.33 mmol) in 100 mL of THF at RT was added 2-chloroisonicotinoyl chloride (3.35 g, 19.04 mmol). A precipitate appeared and the reaction was heated to reflux overnight. The reaction was cooled to RT and concentrated. The precipitate was filtered and washed with $H_2O$, $CH_2Cl_2$, and $Et_2O$ to give N-(2-carbamoyl-phenyl)-2-chloro-isonicotinamide as a light brown solid.

MS (ES−): 274 (M−H)⁻.

EXAMPLE 61

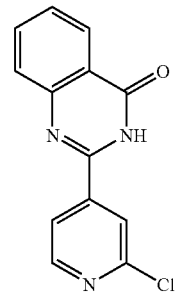

2-(2-Chloro-pyridin-4-yl)-3H-quinazolin-4-one

Sodium hydroxide (5M, 5 mL) was added to a suspension of N-(2-carbamoylphenyl)-2-chloroisonicotinamide (4.14 g, 15.02 mmol) in acetone/water (1/1, 100 mL). The reaction was heated to reflux and stirred overnight. The resulting solid was put into solution with water and was adjusted to pH 7 using 5M HCl. The precipitate was filtered and concentrated with toluene (3×) to give 2-(2-chloro-pyridin-4-yl)-3H-quinazolin-4-one as a light brown solid. MS (ES−): 256 (M−H)⁻.

EXAMPLE 62

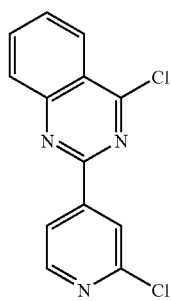

4-Chloro-2-(2-chloro-pyridin-4-yl)-quinazoline

To a suspension of 2-(2-chloro-pyridin-4-yl)-3H-quinazolin-4-one (3.20 g, 12.40 mmol) in POCL₃ (32 mL) was added diisopropylethyl amine (2.16 mL, 12.40 mmol) at RT. The reaction was heated to reflux for 2 h and then cooled and concentrated. The crude product was diluted with CH₂Cl₂ and NaHCO₃ (sat.) was added. The organic layer was separated, dried over Na₂SO₄, filtered and concentrated. The crude product was purified by silica gel chromatography (3/1 Hex/EtOAc) to give 4-chloro-2-(2-chloro-pyridin-4-yl)-quinazoline as a pale yellow solid. MS (ES+): 276 (M+H)⁺.

EXAMPLE 63

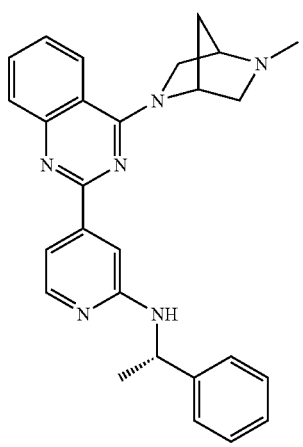

(S)-{4-[4-(5-Methyl-(1S,4S)-2,5-diaza-bicyclo[2.2.1]hept-2-yl)-quinazolin-2-yl]-pyridin-2-yl}-(1-phenyl-ethyl)-amine To a solution of (S)-{4-[4-(2,5-diazabicyclo[2.2.1]hept-2-yl)quinazolin-2-yl]-pyridin-2-yl}-(1-phenyl-ethyl)-amine (105 mg, 0.25 mmol) in 2 mL of CHCl₃ at RT was added formaldehyde (37%, 407 μL, 5.00 mmol), NaCNBH₃ (47 mg, 0.75 mmol) and MeOH (0.4 mL). The reaction stirred at RT overnight and then NaHCO₃ (sat.) was added and the product was extracted with CH₂Cl₂. The combined organic layers were dried over Na₂SO₄, filtered and concentrated. The crude product was purified by silica gel chromatography (gradient elution 1 to 5% MeOH in CH₂Cl₂) to give (S)-{4-[4-(5-methyl-2,5-diaza-bicyclo[2.2.1]hept-2-yl)-quinazolin-2-yl]-pyridin-2-yl}-(1-phenyl-ethyl)-amine as a pale yellow solid. MS (ES+): 437 (M+H)⁺.

EXAMPLE 64

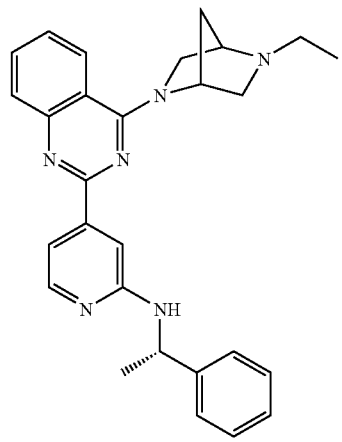

(S)-{4-[4-(5-Ethyl-(1S,4S)-2,5-diaza-bicyclo[2.2.1]hept-2-yl)-quinazolin-2-yl]-pyridin-2-yl}-(1-phenyl-ethyl)-amine The title compound was analogously synthesized by the method described for (S)-{4-[4-(5-Methyl-2,5-diaza-bicyclo[2.2.1]hept-2-yl)-quinazolin-2-yl]-pyridin-2-yl}-(1-phenyl-ethyl)-amine from (S)-{4-[4-(2,5-diaza-bicyclo[2.2.1]hept-2-yl)-quinazolin-2-yl]-pyridin-2-yl}-(1-phenyl-ethyl)-amine. The compound was obtained as a white solid. MS (ES+): 451 (M+H)⁺.

EXAMPLE 65

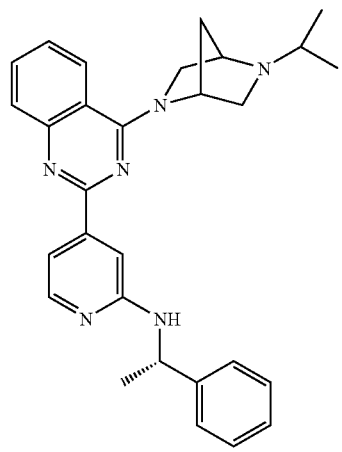

(S)-{4-[4-(5-Isopropyl-(1S,4S)-2,5-diaza-bicyclo[2.2.1]hept-2-yl)-quinazolin-2-yl]-pyridin-2-yl}-(1-phenyl-ethyl)-amine The title compound was analogously synthesized by the method described for (S)-{4-[4-(5-Methyl-2,5-diaza-bicyclo[2.2.1]hept-2-yl)-quinazolin-2-yl]-pyridin-2-yl}-(1-phenyl-ethyl)-amine from (S)-{4-[4-(2,5-diaza-bicyclo[2.2.1]hept-2-yl)-quinazolin-2-yl]-pyridin-2-yl}-(1-phenyl-ethyl)-amine. The compound was obtained as a white solid. MS (ES+): 465 (M+H)+.

EXAMPLE 66

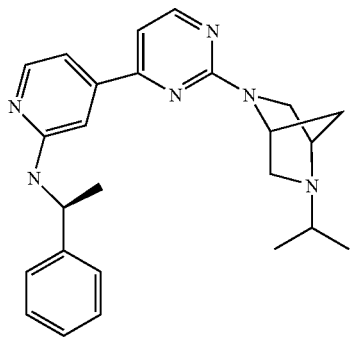

(S)-{4-[2-(5-Isopropyl-(1S,4S)-2,5-diaza-bicyclo[2.2.1]hept-2-yl)-pyrimidin-4-yl]-pyridin-2-yl}-(1-phenyl-ethyl)-amine Step A: 3-(2-Chloro-pyridin-4-yl)-3-oxo-propionic acid ethyl ester (0.35 g, 1.54 mmol) was dissolved in aqueous HCl solution (15 mL, 36.5%) and heated to 50° C. After 3.5 hours, the reaction mixture was cooled down to room temperature and quenched with sodium carbonate until no bubble was generated. The reaction mixture was extracted with EtOAc (3×35 mL) and the organic layers were combined, dried over MgSO4 and concentrated to give the product 1-(2-Chloro-pyridin-4-yl)-ethanone as an off-white solid.

Step B: 1-(2-Chloro-pyridin-4-yl)-ethanone (0.22 g, 1.41 mmol) was dissolved in N,N-dimethyl acetal (25 mL) and heated to reflux overnight. After that, the reaction mixture was cooled down to room temperature. Evaporation of all the solvent under vacuum to give the product 1-(2-chloro-pyridin-4-yl)-3-dimethylamino-propenone as a yellow solid. MS (ES+): 211 (M+H)+.

Step C: To a solution of (tert-butoxycarbonylimino-pyrazol-1-yl-methyl)-carbamic acid tert-butyl ester (0.34 g, 1.09 mmol, 1.00 equiv) in CH3CN were added 2-isopropyl-2,5-diaza-bicyclo[2.2.1]heptane (0.23 g, 1.09 mmol, 1.00 equiv) and 2.00 equivalents of DIEA. The reaction was stirred at room temperature for 13 h, then filtered and extracted with EtOAc (3×50 mL). The combined organic layers were washed with water (1×50 mL) and NaOH (1N, 50 mL), dried over MgSO4 and concentrated to give the product [tert-butoxycarbonylimino-(5-isopropyl-2,5-diaza-bicyclo[2.2.1]hept-2-yl)-methyl]-carbamic acid tert-butyl ester as a white solid Step D: To a solution of [tert-butoxycarbonylimino-(5-isopropyl-2,5-diaza-bicyclo[2.2.1]hept-2-yl)-methyl]-carbamic acid tert-butyl ester (0.38 g, 0.99 mmol) in methanol was added HCl in dioxane (4.0M, 20 mL). After 30 minutes, evaporation of all the solvent to give the product 5-isopropyl-2,5-diaza-bicyclo[2.2.1]heptane-2-carboxamidine HCl salt as a yellow solid 280 mg. MS (ES+): 183 (M+H)+.

Step E: To a solution of 5-isopropyl-2,5-diaza-bicyclo[2.2.1]heptane-2-carboxamidine HCl salt as a yellow solid (0.28 g, 1.10 mmol, 1.00 equiv) and 1-(2-chloro-pyridin-4-yl)-3-dimethylamino-propenone (0.23 g, 1.10 mmol, 1.00 equiv) in isopropanol 25 mL was added KOH (0.19 g, 3.30 mmol, 3.00 equiv). The reaction mixture was heated to reflux for 2 h, then cooled down to room temperature. All the solvent was evaporated and purification by flash chromatography to give the product 2-[4-(2-chloro-pyridin-4-yl)-pyrimidin-2-yl]-5-isopropyl-2,5-diaza-bicyclo[2.2.1]-heptane as a yellow solid.

Step F: To a solution of 2-[4-(2-chloro-pyridin-4-yl)-pyrimidin-2-yl]-5-isopropyl-2,5-diazabicyclo[2.2.1]heptane (0.09 g, 0.27 mmol, 1.00 equiv) in 35 mL toluene was added (S)-α-methylbenzylamine (0.05 g, 0.41 mmol, 1.50 equiv). The mixture was degassed by nitrogen bubbled through for 15 min followed by addition of Pd(OAc)2 (6.13 mg, 0.03 mmol, 0.10 equiv), BINAP (17.27 mg, 0.03 mmol, 0.10 equiv) and NaOtBu (0.192 g, 2.0 mmol) were added, the mixture was warmed to 70° C. and stirred for 2.5 h under nitrogen. The mixture was cooled down to room temperature, filtered and concentrated. Purification by Gilson HPLC gave the product (S)-{4-[2-(5-isopropyl-2,5-diaza-bicyclo[2.2.1]hept-2-yl)-pyrimidin-4-yl]-pyridin-2-yl}-(1-phenyl-ethyl)-amine as a yellow solid. MS (ES+): 415 (M+H)+.

EXAMPLE 67

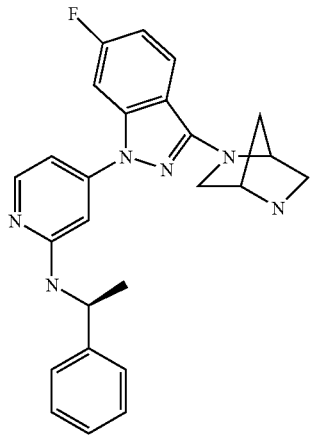

(S)-Benzyl-{4-[3-((1S,4S)-2,5-diaza-bicyclo[2.2.1]hept-2-yl)-6-fluoro-indazol-1-yl]-pyridin-2-yl}-amine Step A: {[Chloro(2-bromo-4-fluorophenyl)methylene]hydrazide}-4-methylbenzene-sulfonic Acid To a solution of 2-bromo-4-fluoro-benzoic acid (10 g) was added thionyl chloride (50 mL). The reaction mixture was stirred at 80° C. for 1 h. The reaction mixture was cooled, and thionyl chloride was removed. To a solution of the 2-bromo-4-fluoro-benzoyl chloride (10.87 g) in dichloromethane was added p-toluenesulfonyl-hydrazide. The heterogeneous reaction was stirred for 1 h at 40° C. Work up by slurry in hexanes gave the desired intermediate as an off-while solid. To the 2-bromo-4-fluoro-benzoic acid tosylated hydrazide (16.2 g) was added thionyl chloride (50 mL). The reaction was stirred at 80° C. for 1 h. Thionyl chloride was removed and the solid was slurryed in heptane to afford the title compound as an off-white solid. MS (ES+): 357(M+H)⁺.

Step B: 5-[(2-Bromo-4-fluoro-phenyl)-((toluene-4-sulfonyl)-hydrazono)-methyl]-2,5-diaza-bicyclo[2.2.1]heptane-2-carboxylic acid tert-butyl ester To a solution of {[chloro(2-bromo-4-fluorophenyl)methylene]hydrazide}-4-methylbenzenesulfonic acid (5.0 g) in THF was added 2,5-diaza-bicyclo[2.2.1]heptane-2-carboxylic acid tert-butyl ester (5.8 g). The reaction mixture was stirred at 65° C. under N₂ overnight. The reaction mixture was cooled to room temperature. Work up between dichloromethane and sodium bicarbonate followed by flash column purification afforded the title compound as an off white solid. MS (ES+): 567 (M+H)⁺; (ES−): 565 (M−H)⁻.

Step C: 5-[6-Fluoro-1-(toluene-4-sulfonyl)-1H-indazol-3-yl]-2,5-diaza-bicyclo[2.2.1]heptane-2-carboxylic acid tert-butyl ester To a solution of 5-[(2-bromo-4-fluoro-phenyl)-((toluene-4-sulfonyl)-hydrazono)-methyl]-2,5-diaza-bicyclo[2.2.1]heptane-2-carboxylic acid tert-butyl ester (3.3 g) in isopropanol (30 mL) was added potassium carbonate (1.0 g), and copper iodide (0.026 g). The reaction mixture was stirred at 84° C. under N₂ for 30 min. The reaction was cooled to r.t., and 60 mL of H₂O was added. The reaction was stirred at 0° C. for 15 min, and the solid was filtered and dried under vacuum to afforded the title compound as an off white solid. MS (ES+): 487 (M+H)⁺.

Step D: 5-(6-Fluoro-1H-indazol-3-yl)-2,5-diaza-bicyclo [2.2.1]heptane-2-carboxylic acid tert-butyl ester To a solution of 5-[6-fluoro-1-(toluene-4-sulfonyl)-1H-indazol-3-yl]-2,5-diaza-bicyclo[2.2.1]heptane-2-carboxylic acid tert-butyl ester (2.5 g in 1:1 ethanol:H₂O 20 mL was added potassium hydroxide (1 g). The reaction was stirred at 78° C. for 16 h then cooled to r.t. and acidified to pH 5 with HCl. Ethanol was evaporated, work up between dichloromethane and sodium bicarbonate followed by flash column purification afforded the title compound as an off white solid. MS (ES+): 333 (M+H)⁺; (ES−): 331 (M−H)⁻.

Step E: 5-[1-(2-Chloro-pyridin-4-yl)-6-fluoro-1H-indazol-3-yl]-2,5-diaza-bicyclo[2.2.1]heptane-2-carboxylic acid tert-butyl ester To a solution of 5-(6-fluoro-1H-indazol-3-yl)-2,5-diazabicyclo[2.2.1]heptane-2-carboxylic acid tert-butyl ester (600 mg) in toluene (10 mL) was added 2-chloro-4-iodo-pyridine (519 mg), copper iodide (17 mg), potassium phosphate (807 mg) and cyclohexane-1,2-diamine. The reaction was stirred at 80° C. for overnight, cooled to r.t., work up between dichloromethane and sodium bicarbonate followed by flash column purification afforded the title compound as an off white solid. MS (ES+): 444 (M+H)⁺.

Step F: 5-{6-Fluoro-1-[2-(1-phenyl-ethylamino)-pyridin-4-yl]-1H-indazol-3-yl}-2,5-diaza-bicyclo[2.2.1]heptane-2-carboxylic acid tert-butyl ester To a solution of 5-[1-(2-chloro-pyridin-4-yl)-6-fluoro-1H-indazol-3-yl]-2,5-diaza-bicyclo[2.2.1]heptane-2-carboxylic acid tert-butyl ester (193 mg) in toluene was added 1-phenylethylamine (0.048 mL), palladium acetate (10 mg), biphenyl naphthalene (27 mg), and sodium tert-butoxide (117 mg). The reaction was stirred at 70° C. for 2 h, cooled to r.t., filtered through a bed of celite, and chromatographed to afforded the title compound as an white solid MS (ES+): 529 (M+H)⁺; (ES−): 527 (M−H)⁻.

Step G: {4-[3-(2,5-Diaza-bicyclo[2.2.1]hept-2-yl)-6-fluoroindazol-1-yl]-pyridin-2-yl}-(1-phenyl-ethyl)-amine To a solution of 5-{6-fluoro-1-[2-(1-phenyl-ethylamino)-pyridin-4-yl]-1H-indazol-3-yl}-2,5-diaza-bicyclo[2.2.1] heptane-2-carboxylic acid tert-butyl ester (160 mg) in MeOH (2 mL) followed by 4N HCL in 1,4 dioxane (5 mL) at room temperature. After 30 min, work up between dichloromethane and sodium bicarbonate followed by flash column purification afforded the title compound as an off white solid. MS (ES+): 429 (M+H)⁺; (ES−): 427 (M−H)⁻.

EXAMPLE 68

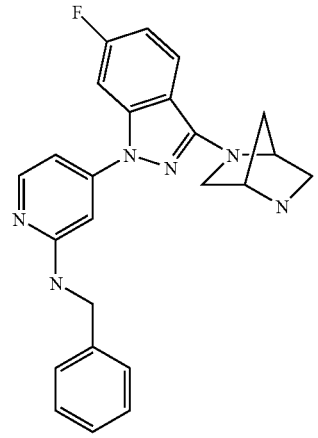

Benzyl-{4-[3-((1S,4S)-2,5-diaza-bicyclo[2.2.1]hept-2-yl)-6-fluoro-indazol-1-yl]-pyridin-2-yl}-amine The title compound was analogously synthesized by the method described in example 1. benzylamine, instead of 1-phenyl-ethylamine, was used. MS (ES+): 415 (M+H)⁺; (ES−): 413 (M−H)⁻.

EXAMPLE 69

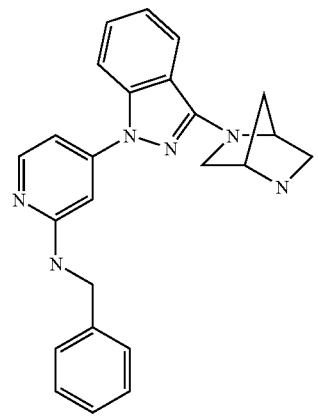

Benzyl-{4-[3-(1S,4S)-2,5-diaza-bicyclo[2.2.1]hept-2-yl)-indazol-1-yl]-pyridin-2-yl}-amine The title compound was analogously synthesized by the method described in example 1. 2-Bromo-benzoic acid, instead of 2-bromo-4-fluoro-benzoic acid was used. MS (ES+): 397 (M+H)⁺; (ES−): 395 (M−H)⁻.

EXAMPLE 70

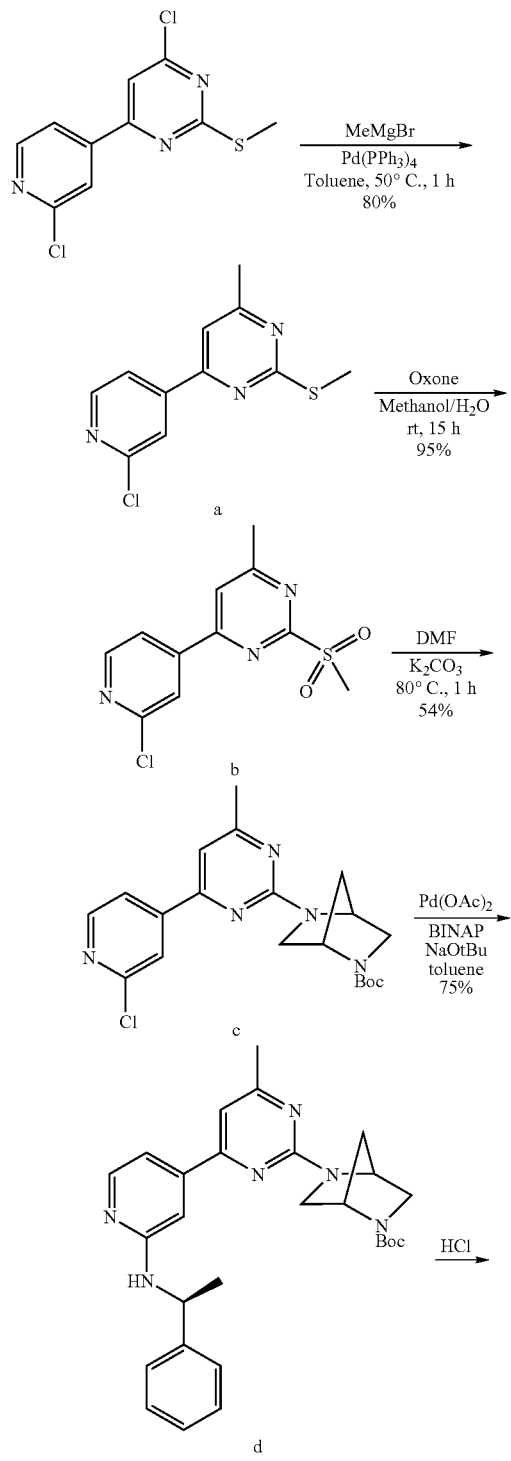

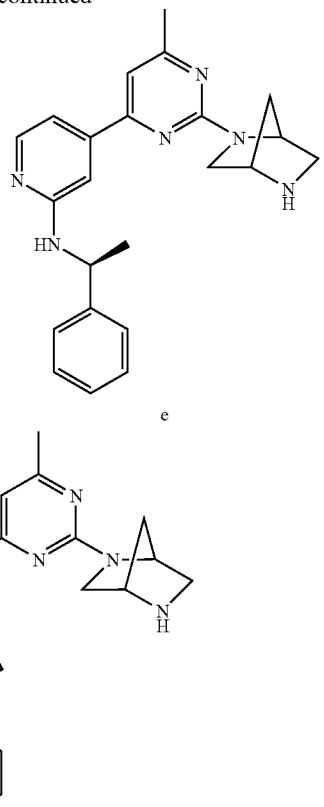

Step A: Synthesis of 4-(2-chloropyridin-4-yl)-6-methyl-2-(methylthio)pyrimidine

The mixture of 4-chloro-6-(2-chloropyridin-4-yl)-2-(methylthio)pyrimidine (8.7 g, 32 mmol) (for synthesis see to Example 1 step D) in 150 ml toluene stirred at room temperature was treated with Pd(PPh₃)₄ (0.37 g, 0.32 mmol) and 25.1 ml 1.4 M MeMgCl in toluene/THF (3:1). The mixture was warmed up to 50° C. and stirred for 2 h. MS showed all starting material was converted. The reaction mixture was cooled down to room temperature and quenched with 100 ml sat. NH₄Cl, extracted with ethyl acetate 3×100 ml. The combined organics was dried over anhydrous Na₂SO₄. After purification by flash chromatography, the title compound was obtained. MS (ES+): 252 (M+H)⁺.

Step B: Synthesis of 4-(2-chloropyridin-4-yl)-6-methyl-2-(methylsulfonyl)pyrimidine The mixture of 4-(2-chloropyridin-4-yl)-6-methyl-2-(methylthio)pyrimidine (4.9 g, 19.5 mmol), Oxone (18 g, 29.3 mmol) in methanol/H₂O (9:1) was stirred at room temperature for 2 h. MS showed all starting material was converted. The reaction mixture was quenched with 100 ml sat. Na₂S₂O₃, extracted with DCM 3×100 ml. The combined organics was dried over anhydrous Na₂SO₄. After purification by flash chromatography, the title compound was obtained. MS (ES+): 268 (M+H)⁺.

Step C: Synthesis of tert-butyl 5-(4-(2-chloropyridin-4-yl)-6-methylpyrimidin-2-yl)-2,5-diaza-bicyclo[2.2.1]heptane-2-carboxylate The mixture of 4-(2-chloropyridin-4-yl)-6-methyl-2-(methylsulfonyl)pyrimidine (6.17 g, 23 mmol), tert-butyl 2,5-diaza-bicyclo[2.2.1]heptane-2-carboxylate (4.8 g, 24.3 mmol) and potassium carbonate (3.2 g, 23 mmol) in 80 DMF was stirred at 80° C. under nitrogen for 1 h. The reaction mixture was cooled down to room temperature and diluted with 300 ml ethyl acetate. The mixture was washed with water 3×100 ml, and brine 100 ml. The organic was dried over anhydrous $Na_2SO_4$. After purification by flash chromatography, the title compound was obtained. MS (ES+): 402 $(M+H)^+$.

Step D: Synthesis of tert-butyl 5-(4-methyl-6-(2-((S)-1-phenylethylamino)pyridin-4-yl)pyrimidin-2-yl)-2,5-diaza-bicyclo[2.2.1]heptane-2-carboxylate To a 100 mL RBF, was added tert-butyl 5-(4-(2-chloropyridin-4-yl)-6-methylpyrimidin-2-yl)-2,5-diaza-bicyclo[2.2.1]heptane-2-carboxylate (4.0 g, 10 mmol), 100 mL toluene, and (S)-α-methylbenzylamine (1.93 mL, 15 mmol). The mixture was degassed by nitrogen bubbled through for 1 h. After $Pd(OAc)_2$ (224 mg, 1.0 mmol), BINAP (622 mg, 1.0 mmol) and NaOtBu (1.92 g, 20 mmol) were added, the mixture was warmed up to 90° C. and stirred for 2 h under nitrogen. The mixture was cooled down to room temperature, diluted with 300 mL DCM, washed with 20 mL sat. $NaHCO_3$, and dried over anhydrous $Na_2SO_4$. After purification by flash chromatography, the title compound was obtained as pale yellow solid. MS (ES+): 487 $(M+H)^+$.

Step E: 4-(2-(2,5-diaza-bicyclo[2.2.1]heptan-2-yl)-6-methylpyrimidin-4-yl)-N-((S)-1-phenylethyl)pyridin-2-amine The mixture of 4.24 g (8.7 mmol) of tert-butyl 5-(4-methyl-6-(2-((S)-1-phenylethylamino)pyridin-4-yl)pyrimidin-2-yl)-2,5-diaza-bicyclo[2.2.1]heptane-2-carboxylate in 10 mL methanol stirred at 0° C. under nitrogen was treated with 20 ml 4 M HCl in dioxane, and stirred for 1 h at room temperature. MS showed all starting material was converted. The reaction mixture was diluted with 300 ml DCM, and washed carefully with sat. $NaHCO_3$. The organic was dried over anhydrous $Na_2SO_4$. After purification by flash chromatography, the title compound was obtained. MS (ES+): 387 $(M+H)^+$.

EXAMPLE 71

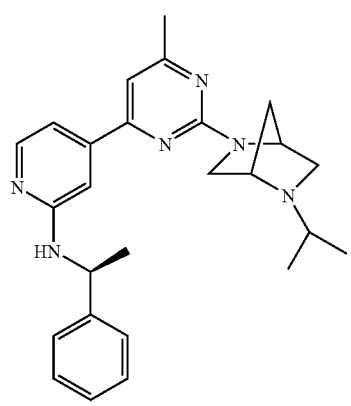

4-(2-(5-isopropyl-2,5-diaza-bicyclo[2.2.1]heptan-2-yl)-6-methylpyrimidin-4-yl)-N-((S)-1-phenylethyl)pyridin-2-amine A solution of 4-(2-(2,5-diaza-bicyclo[2.2.1]heptan-2-yl)-6-methylpyrimidin-4-yl)-N-((S)-1-phenylethyl)pyridin-2-amine (0.23 g, 0.60 mmol) in chloroform (5 mL) were added acetone (1 mL) and sodium triacetoxyborohydride (0.45 g, 2.14 mmol) and stirred at 70° C. for 2 h. Upon cooling to room temperature, the reaction was diluted with methylene chloride and washed with saturated sodium bicarbonate, brine, and dried over anhydrous $K_2CO_3$. Flash chromatography of the crude product with 1% 2M $NH_3$ in $MeOH/CHCl_3$ afforded the title compound as a pale yellow solid. MS (ES+): 429[M+H]+.

The following compounds were synthesized according to the various procedures provided in the examples above, particularly those of examples 1-4, 13, 15, 21, 22, 40-44 and 45-49:

EXAMPLE 72

'6-(2-(((1S)-1-(4-fluorophenyl)ethyl)amino)-4-pyridinyl)-3-methyl-2-(5-methyl-2,5-diazabicyclo[2.2.1]hept-2-yl)-4(3H)-pyrimidinone;

EXAMPLE 73

'2-(2,5-diazabicyclo[2.2.1]hept-2-yl)-3-methyl-6-(2-((2-thienylmethyl)amino)-4-pyridinyl)-4(3H)-pyrimidinone;

EXAMPLE 74

'1,1-dimethylethyl 5-(1-methyl-6-oxo-4-(2-(((1R)-1-phenylethyl)amino)-4-pyridinyl)-1,6-dihydro-2-pyrimidinyl)-2,5-diazabicyclo[2.2.1]heptane-2-carboxylate;

EXAMPLE 75

'3-methyl-2-(5-methyl-2,5-diazabicyclo[2.2.1]hept-2-yl)-6-(2-(((1S)-1-phenylethyl)amino)-4-pyridinyl)-4(3H)-pyrimidinone;

EXAMPLE 76

'3-methyl-2-(5-(1-methylethyl)-2,5-diazabicyclo[2.2.1]hept-2-yl)-6-(2-(((1S)-1-phenylethyl)amino)-4-pyridinyl)-4(3H)-pyrimidinone;

EXAMPLE 77

'4-(5-(2,5-diazabicyclo[2.2.1]hept-2-yl)[1,2,4]triazolo[4,3-c]pyrimidin-7-yl)-N-((1S)-1-phenylethyl)-2-pyridinamine;

EXAMPLE 78

'1,1-dimethylethyl 5-(7-(2-amino-4-pyridinyl)imidazo[1,2-c]pyrimidin-5-yl)-2,5-diazabicyclo[2.2.1]heptane-2-carboxylate;

EXAMPLE 79

'4-(5-(5-(methylsulfonyl)-2,5-diazabicyclo[2.2.1]hept-2-yl)imidazo[1,2-c]pyrimidin-7-yl)-N-((1S)-1-phenylethyl)-2-pyridinamine;

EXAMPLE 80

'(1S)-1-methyl-2-oxo-2-(5-(7-(2-(((1S)-1-phenylethyl)amino)-4-pyridinyl)imidazo[1,2-c]pyrimidin-5-yl)-2,5-diazabicyclo[2.2.1]hept-2-yl)ethyl acetate;

EXAMPLE 81

'1,1-dimethylethyl 5-(7-(2-(((2S)-2-(acetyloxy)propanoyl)amino)-4-pyridinyl)imidazo[1,2-c]pyrimidin-5-yl)-2,5-diazabicyclo[2.2.1]heptane-2-carboxylate;

EXAMPLE 82

'(2S)-1-oxo-1-(5-(7-(2-(((1S)-1-phenylethyl)amino)-4-pyridinyl)imidazo[1,2-c]pyrimidin-5-yl)-2,5-diazabicyclo[2.2.1]hept-2-yl)-2-propanol;

EXAMPLE 83

'N-((1S)-1-cyclohexylethyl)-4-(5-(2,5-diazabicyclo[2.2.1]hept-2-yl)imidazo[1,2-c]pyrimidin-7-yl)-2-pyridinamine;

EXAMPLE 84

'4-(5-(5-ethyl-2,5-diazabicyclo[2.2.1]hept-2-yl)imidazo[1,2-c]pyrimidin-7-yl)-N-((1S)-1-phenylethyl)-2-pyridinamine;

EXAMPLE 85

'N-((1R)-1-cyclopropylethyl)-4-(5-(2,5-diazabicyclo[2.2.1]hept-2-yl)imidazo[1,2-c]pyrimidin-7-yl)-2-pyridinamine;

EXAMPLE 86

'N-((1S)-1-cyclohexylethyl)-4-(5-(5-(1-methylethyl)-2,5-diazabicyclo[2.2.1]hept-2-yl)imidazo[1,2-c]pyrimidin-7-yl)-2-pyridinamine;

EXAMPLE 87

'4-(5-(2,5-diazabicyclo[2.2.1]hept-2-yl)imidazo[1,2-c]pyrimidin-7-yl)-N-((1S)-1-(1-naphthalenyl)ethyl)-2-pyridinamine;

EXAMPLE 88

'4-(5-(5-(1-methylethyl)-2,5-diazabicyclo[2.2.1]hept-2-yl)imidazo[1,2-c]pyrimidin-7-yl)-N-(2-thienylmethyl)-2-pyridinamine;

EXAMPLE 89

'N-(4-(5-(5-(1-methylethyl)-2,5-diazabicyclo[2.2.1]hept-2-yl)imidazo[1,2-c]pyrimidin-7-yl)-2-pyridinyl)benzenesulfonamide;

EXAMPLE 90

'N-(4-(5-(5-(1-methylethyl)-2,5-diazabicyclo[2.2.1]hept-2-yl)imidazo[1,2-c]pyrimidin-7-yl)-2-pyridinyl)benzamide;

EXAMPLE 91

'N-(2-furanylmethyl)-4-(5-(5-(1-methylethyl)-2,5-diazabicyclo[2.2.1]hept-2-yl)imidazo[1,2-c]pyrimidin-7-yl)-2-pyridinamine;

EXAMPLE 92

'N-((1S)-1-(4-fluorophenyl)ethyl)-4-(5-(5-(1-methylethyl)-2,5-diazabicyclo[2.2.1]hept-2-yl)imidazo[1,2-c]pyrimidin-7-yl)-2-pyridinamine;

EXAMPLE 93

'4-(5-(5-(2,2-difluoroethyl)-2,5-diazabicyclo[2.2.1]hept-2-yl)imidazo[1,2-c]pyrimidin-7-yl)-N-((1S)-1-phenylethyl)-2-pyridinamine;

EXAMPLE 94

'4-(5-((1S,4S)-5-butyl-2,5-diazabicyclo[2.2.1]hept-2-yl)imidazo[1,2-c]pyrimidin-7-yl)-N-((1S)-1-phenylethyl)-2-pyridinamine;

EXAMPLE 95

'N-((1S)-1-phenylethyl)-4-(5-((1S,4S)-5-((1S)-2,2,2-trifluoro-1-methylethyl)-2,5-diazabicyclo[2.2.1]hept-2-yl)imidazo[1,2-c]pyrimidin-7-yl)-2-pyridinamine;

EXAMPLE 96

'4-(5-(5-(1-methylethyl)-2,5-diazabicyclo[2.2.1]hept-2-yl)imidazo[1,2-c]pyrimidin-7-yl)-N-(1-naphthalenylmethyl)-2-pyridinamine;

EXAMPLE 97

'4-(2-(2,5-diazabicyclo[2.2.1]hept-2-yl)-1,3-thiazol-4-yl)-N-((1S)-1-phenylethyl)-2-pyridinamine;

EXAMPLE 98

'4-(2-(5-(1-methylethyl)-2,5-diazabicyclo[2.2.1]hept-2-yl)-1,3-thiazol-4-yl)-N-((1S)-1-phenylethyl)-2-pyridinamine;

EXAMPLE 99

'4-(5-(5-(1-methylethyl)-2,5-diazabicyclo[2.2.1]hept-2-yl)imidazo[1,2-c]pyrimidin-7-yl)-N-((1S)-1-(4-(methyloxy)phenyl)ethyl)-2-pyridinamine;

EXAMPLE 100

'4-(5-(2,5-diazabicyclo[2.2.1]hept-2-yl)imidazo[1,2-c]pyrimidin-7-yl)-N-((1S)-1-(4-fluorophenyl)ethyl)-2-pyridinamine;

EXAMPLE 101

'4-(3-(2,5-diazabicyclo[2.2.1]hept-2-yl)-1H-indazol-1-yl)-N-((1S)-1-phenylethyl)-2-pyridinamine;

EXAMPLE 102

'4-(5-(5-((1S)-1-methylpropyl)-2,5-diazabicyclo[2.2.1]hept-2-yl)imidazo[1,2-c]pyrimidin-7-yl)-N-((1S)-1-phenylethyl)-2-pyridinamine;

EXAMPLE 103

'4-(5-(5-((1R)-1-methylpropyl)-2,5-diazabicyclo[2.2.1]hept-2-yl)imidazo[1,2-c]pyrimidin-7-yl)-N-((1S)-1-phenylethyl)-2-pyridinamine;

EXAMPLE 104

'4-(5-(5-cyclopentyl-2,5-diazabicyclo[2.2.1]hept-2-yl)imidazo[1,2-c]pyrimidin-7-yl)-N-((1S)-1-phenylethyl)-2-pyridinamine;

EXAMPLE 105

'1-(5-(7-(2-(((1S)-1-phenylethyl)amino)-4-pyridinyl)imidazo[1,2-c]pyrimidin-5-yl)-2,5-diazabicyclo[2.2.1]hept-2-yl)-2-propanol;

EXAMPLE 106

'4-(5-(5-methyl-2,5-diazabicyclo[2.2.1]hept-2-yl)imidazo[1,2-c]pyrimidin-7-yl)-N-((1S)-1-phenylethyl)-2-pyridinamine;

EXAMPLE 107

'4-(3-(5-(1-methylethyl)-2,5-diazabicyclo[2.2.1]hept-2-yl)-1H-indazol-1-yl)-N-((1S)-1-phenylethyl)-2-pyridinamine;

EXAMPLE 108

'N-((1S)-1-phenylethyl)-4-(5-((1S,4S)-5-(2-(phenyloxy)ethyl)-2,5-diazabicyclo[2.2.1]hept-2-yl)imidazo[1,2-c]pyrimidin-7-yl)-2-pyridinamine;

EXAMPLE 109

'4-(5-((1R,4R)-5-(1-methylethyl)-2,5-diazabicyclo[2.2.1]hept-2-yl)imidazo[1,2-c]pyrimidin-7-yl)-N-((1S)-1-phenylethyl)-2-pyridinamine;

EXAMPLE 110

'N-((1S)-1-phenylethyl)-4-(5-(5-propyl-2,5-diazabicyclo[2.2.1]hept-2-yl)imidazo[1,2-c]pyrimidin-7-yl)-2-pyridinamine;

EXAMPLE 111

'4-(5-(5-(2-methylpropyl)-2,5-diazabicyclo[2.2.1]hept-2-yl)imidazo[1,2-c]pyrimidin-7-yl)-N-((1S)-1-phenylethyl)-2-pyridinamine;

EXAMPLE 112

'4-(5-(2,5-diazabicyclo[2.2.1]hept-2-yl)imidazo[1,2-c]pyrimidin-7-yl)-N-(phenylmethyl)-2-pyridinamine;

EXAMPLE 113

'4-(5-(2,5-diazabicyclo[2.2.1]hept-2-yl)imidazo[1,2-c]pyrimidin-7-yl)-N-methyl-N-(phenylmethyl)-2-pyridinamine;

EXAMPLE 114

'N-((3-chlorophenyl)methyl)-4-(5-(2,5-diazabicyclo[2.2.1]hept-2-yl)imidazo[1,2-c]pyrimidin-7-yl)-2-pyridinamine;

EXAMPLE 115

'4-(5-((1S,4S)-5-(1,1-dimethylethyl)-2,5-diazabicyclo[2.2.1]hept-2-yl)imidazo[1,2-c]pyrimidin-7-yl)-N-((1S)-1-phenylethyl)-2-pyridinamine;

EXAMPLE 116

'1,1-dimethylethyl 5-(7-(2-((phenylmethyl)amino)-4-pyridinyl)imidazo[1,2-c]pyrimidin-5-yl)-2,5-diazabicyclo[2.2.1]heptane-2-carboxylate;

EXAMPLE 117

'4-(5-((1R,4R)-5-(1,1-dimethylethyl)-2,5-diazabicyclo[2.2.1]hept-2-yl)imidazo[1,2-c]pyrimidin-7-yl)-N-((1S)-1-phenylethyl)-2-pyridinamine;

EXAMPLE 118

'1,1-dimethylethyl 5-(7-(2-(((2-fluorophenyl)methyl)amino)-4-pyridinyl)imidazo[1,2-c]pyrimidin-5-yl)-2,5-diazabicyclo[2.2.1]heptane-2-carboxylate;

EXAMPLE 119

'4-(5-(2,5-diazabicyclo[2.2.1]hept-2-yl)imidazo[1,2-c]pyrimidin-7-yl)-N-((3-fluorophenyl)methyl)-2-pyridinamine;

EXAMPLE 120

'N-((1S)-1-(4-fluorophenyl)ethyl)-4-(3-(5-(1-methylethyl)-2,5-diazabicyclo [2.2.1]hept-2-yl)-1H-indazol-1-yl)-2-pyridinamine;

EXAMPLE 121

'4-(4-(2,5-diazabicyclo[2.2.1]hept-2-yl)-1H-pyrazol-1-yl)-N-((1S)-1-phenylethyl)-2-pyridinamine;

EXAMPLE 122

'2-((4-(5-(2,5-diazabicyclo[2.2.1]hept-2-yl)imidazo[1,2-c]pyrimidin-7-yl)-2-pyridinyl)amino)-2-phenylethanol;

EXAMPLE 123

'1,1-dimethylethyl 5-(1-(2-(((1S)-1-phenylethyl)amino)-4-pyridinyl)-1H-indazol-3-yl)-2,5-diazabicyclo[2.2.1]heptane-2-carboxylate;

EXAMPLE 124

'4-(5-((1S,4S,6S)-6-methyl-5-(1-methylethyl)-2,5-diazabicyclo[2.2.1]hept-2-yl)imidazo[1,2-c]pyrimidin-7-yl)-N-((1S)-1-phenylethyl)-2-pyridinamine;

EXAMPLE 125

'4-(5-(5-methyl-2,5-diazabicyclo[2.2.1]hept-2-yl)imidazo[1,2-c]pyrimidin-7-yl)-N-(phenylmethyl)-2-pyridinamine;

EXAMPLE 126

'4-(5-(5-(1-methylethyl)-2,5-diazabicyclo[2.2.1]hept-2-yl)imidazo[1,2-c]pyrimidin-7-yl)-N-(phenylmethyl)-2-pyridinamine;

EXAMPLE 127

'N-((3-fluorophenyl)methyl)-4-(5-(5-(1-methylethyl)-2,5-diazabicyclo[2.2.1]hept-2-yl)imidazo[1,2-c]pyrimidin-7-yl)-2-pyridinamine;

EXAMPLE 128

'4-(3-(5-(1-methylethyl)-2,5-diazabicyclo[2.2.1]hept-2-yl)-1H-indazol-1-yl)-N-(phenylmethyl)-2-pyridinamine;

EXAMPLE 129

'N-((1S)-1-phenylethyl)-4-(5-(5-(3-(phenyloxy)propyl)-2,5-diazabicyclo[2.2.1]hept-2-yl)imidazo[1,2-c]pyrimidin-7-yl)-2-pyridinamine;

EXAMPLE 130

'N-((2-fluorophenyl)methyl)-4-(3-(5-(1-methylethyl)-2,5-diazabicyclo[2.2.1]hept-2-yl)-1H-indazol-1-yl)-2-pyridinamine;

EXAMPLE 131

'4-(3-(2,5-diazabicyclo[2.2.1]hept-2-yl)-1H-indazol-1-yl)-N-((2-fluorophenyl)methyl)-2-pyridinamine;

EXAMPLE 132

'N-((1S)-1-phenylethyl)-4-(5-(5-(phenylmethyl)-2,5-diazabicyclo[2.2.1]hept-2-yl)imidazo[1,2-c]pyrimidin-7-yl)-2-pyridinamine;

EXAMPLE 133

'4-(3-(2,5-diazabicyclo[2.2.1]hept-2-yl)-1H-indazol-1-yl)-N-(phenylmethyl)-2-pyridinamine;

EXAMPLE 134

'N-((2-fluorophenyl)methyl)-4-(5-(5-methyl-2,5-diazabicyclo[2.2.1]hept-2-yl)imidazo[1,2-c]pyrimidin-7-yl)-2-pyridinamine;

EXAMPLE 135

'4-(5-(5-ethyl-2,5-diazabicyclo[2.2.1]hept-2-yl)imidazo[1,2-c]pyrimidin-7-yl)-N-((2-fluorophenyl)methyl)-2-pyridinamine;

EXAMPLE 136

'4-(5-(5-ethyl-2,5-diazabicyclo[2.2.1]hept-2-yl)imidazo[1,2-c]pyrimidin-7-yl)-N-(phenylmethyl)-2-pyridinamine;

EXAMPLE 137

'methyl 3-(5-(7-(2-(((1S)-1-phenylethyl)amino)-4-pyridinyl)imidazo[1,2-c]pyrimidin-5-yl)-2,5-diazabicyclo[2.2.1]hept-2-yl)propanoate;

EXAMPLE 138

'3-(5-(7-(2-(((1S)-1-phenylethyl)amino)-4-pyridinyl)imidazo[1,2-c]pyrimidin-5-yl)-2,5-diazabicyclo[2.2.1]hept-2-yl)propanoic acid;

EXAMPLE 139

'4-(3-(2,5-diazabicyclo[2.2.1]hept-2-yl)-5-fluoro-1H-indazol-1-yl)-N-((1S)-1-phenylethyl)-2-pyridinamine;

EXAMPLE 140

'4-(3-(2,5-diazabicyclo[2.2.1]hept-2-yl)-1H-indazol-1-yl)-N-((2-fluorophenyl)methyl)-2-pyridinamine;

EXAMPLE 141

'4-(3-(5-methyl-2,5-diazabicyclo[2.2.1]hept-2-yl)-1H-indazol-1-yl)-N-(phenylmethyl)-2-pyridinamine;

EXAMPLE 142

'4-(5-fluoro-3-(5-methyl-2,5-diazabicyclo[2.2.1]hept-2-yl)-1H-indazol-1-yl)-N-((1S)-1-phenylethyl)-2-pyridinamine;

EXAMPLE 143

'N-((2-fluorophenyl)methyl)-4-(3-(5-methyl-2,5-diazabicyclo[2.2.1]hept-2-yl)-1H-indazol-1-yl)-2-pyridinamine;

EXAMPLE 144

'4-(3-(5-ethyl-2,5-diazabicyclo[2.2.1]hept-2-yl)-1H-indazol-1-yl)-N-(phenylmethyl)-2-pyridinamine;

EXAMPLE 145

'4-(5-fluoro-3-(5-(1-methylethyl)-2,5-diazabicyclo[2.2.1]hept-2-yl)-1H-indazol-1-yl)-N-((1S)-1-phenylethyl)-2-pyridinamine;

EXAMPLE 146

'2-(7-(2-(3,4-dihydro-2(1H)-isoquinolinyl)-4-pyridinyl)imidazo[1,2-c]pyrimidin-5-yl)-5-(1-methylethyl)-2,5-diazabicyclo[2.2.1]heptane;

EXAMPLE 147

'4-(3-(2,5-diazabicyclo[2.2.1]hept-2-yl)-1H-indazol-1-yl)-N-phenyl-2-pyridinamine;

EXAMPLE 148

'4-(3-(2,5-diazabicyclo[2.2.1]hept-2-yl)-6-fluoro-1H-indazol-1-yl)-N-(phenylmethyl)-2-pyridinamine;

EXAMPLE 149

'4-(3-(2,5-diazabicyclo[2.2.1]hept-2-yl)-1H-indazol-1-yl)-N-((1S)-1-(2-fluorophenyl)ethyl)-2-pyridinamine;

EXAMPLE 150

'4-(3-(2,5-diazabicyclo[2.2.1]hept-2-yl)-6-fluoro-1H-indazol-1-yl)-N-((1S)-1-phenylethyl)-2-pyridinamine;

EXAMPLE 151

'4-(3-((1S,4S)-5-(1-methylethyl)-2,5-diazabicyclo[2.2.1]hept-2-yl)-1H-pyrazol-1-yl)-N-((1S)-1-phenylethyl)-2-pyridinamine;

EXAMPLE 152

'4-(3-(2,5-diazabicyclo[2.2.1]hept-2-yl)-7-fluoro-1H-indazol-1-yl)-N-((1S)-1-phenylethyl)-2-pyridinamine;

EXAMPLE 153

'4-(3-(5-ethyl-2,5-diazabicyclo[2.2.1]hept-2-yl)-7-fluoro-1H-indazol-1-yl)-N-((1S)-1-phenylethyl)-2-pyridinamine;

EXAMPLE 154

'4-(3-(5-ethyl-2,5-diazabicyclo[2.2.1]hept-2-yl)-1H-indazol-1-yl)-N-((1S)-1-phenylethyl)-2-pyridinamine;

EXAMPLE 155

'2-((1S,4S)-2,5-diazabicyclo[2.2.1]hept-2-yl)-5-(3,4-difluorophenyl)-3-methyl-6-(2-((2-phenylethyl)amino)-4-pyridinyl)-4(3H)-pyrimidinone;

EXAMPLE 156

'4-(6-fluoro-3-(5-(1-methylethyl)-2,5-diazabicyclo[2.2.1]hept-2-yl)-1H-indazol-1-yl)-N-(phenylmethyl)-2-pyridinamine;

EXAMPLE 157

'4-(6-fluoro-3-(5-methyl-2,5-diazabicyclo[2.2.1]hept-2-yl)-1H-indazol-1-yl)-N-(phenylmethyl)-2-pyridinamine;

EXAMPLE 158

'4-(4-chloro-3-(2,5-diazabicyclo[2.2.1]hept-2-yl)-1H-indazol-1-yl)-N-((1S)-1-phenylethyl)-2-pyridinamine;

EXAMPLE 159

'4-(4-chloro-3-(5-(1-methylethyl)-2,5-diazabicyclo[2.2.1]hept-2-yl)-1H-indazol-1-yl)-N-((1S)-1-phenylethyl)-2-pyridinamine;

EXAMPLE 160

'4-(4-chloro-3-(5-ethyl-2,5-diazabicyclo[2.2.1]hept-2-yl)-1H-indazol-1-yl)-N-((1S)-1-phenylethyl)-2-pyridinamine;

EXAMPLE 161

'4-(3-(5-ethyl-2,5-diazabicyclo[2.2.1]hept-2-yl)-6-fluoro-1H-indazol-1-yl)-N-(phenylmethyl)-2-pyridinamine;

EXAMPLE 162

'4-(3-(2,5-diazabicyclo[2.2.1]hept-2-yl)-6-nitro-1H-indazol-1-yl)-N-((1S)-1-phenylethyl)-2-pyridinamine;

EXAMPLE 163

'4-(4-chloro-3-((1S,4S)-2,5-diazabicyclo[2.2.1]hept-2-yl)-1H-indazol-1-yl)-N-(phenylmethyl)-2-pyridinamine;

EXAMPLE 164

'4-(6-chloro-3-((1S,4S)-2,5-diazabicyclo[2.2.1]hept-2-yl)-1H-indazol-1-yl)-N-((1S)-1-phenylethyl)-2-pyridinamine;

EXAMPLE 165

'4-(3-((1S,4S)-2,5-diazabicyclo[2.2.1]hept-2-yl)-6-fluoro-1H-indazol-1-yl)-N-methyl-N-(phenylmethyl)-2-pyridinamine;

EXAMPLE 166

'4-(3-((1S,4S)-2,5-diazabicyclo[2.2.1]hept-2-yl)-6-methyl-1H-indazol-1-yl)-N-(phenylmethyl)-2-pyridinamine;

EXAMPLE 167

'1,1-dimethylethyl (1S,4S)-5-(4-chloro-1-(2-((phenylmethyl)amino)-4-pyridinyl)-1H-indazol-3-yl)-2,5-diazabicyclo[2.2.1]heptane-2-carboxylate;

EXAMPLE 168

'4-(3-((1S,4S)-2,5-diazabicyclo[2.2.1]hept-2-yl)-6-methyl-1H-indazol-1-yl)-N-((1R)-1-phenylethyl)-2-pyridinamine;

EXAMPLE 169

'1,1-dimethylethyl (1S,4S)-5-(6-methyl-1-(2-(((1R)-1-phenylethyl)amino)-4-pyridinyl)-1H-indazol-3-yl)-2,5-diazabicyclo[2.2.1]heptane-2-carboxylate;

EXAMPLE 170

'4-(6-methyl-3-((1S,4S)-5-(1-methylethyl)-2,5-diazabicyclo[2.2.1]hept-2-yl)-1H-indazol-1-yl)-N-((1R)-1-phenylethyl)-2-pyridinamine;

EXAMPLE 171

'3-((1S,4S)-2,5-diazabicyclo[2.2.1]hept-2-yl)-1-(2-(((1S)-1-phenylethyl)amino)-4-pyridinyl)-1H-indazol-6-amine;

EXAMPLE 172

'N-(3-((1S,4S)-2,5-diazabicyclo[2.2.1]hept-2-yl)-1-(2-(((1S)-1-phenylethyl)amino)-4-pyridinyl)-1H-indazol-6-yl)acetamide;

EXAMPLE 173

'N-(3-((1S,4S)-2,5-diazabicyclo[2.2.1]hept-2-yl)-1-(2-(((1S)-1-phenylethyl)amino)-4-pyridinyl)-1H-indazol-6-yl)methanesulfonamide;

EXAMPLE 174

'3-((1S,4S)-2,5-diazabicyclo[2.2.1]hept-2-yl)-6-nitro-1-(2-(((1S)-1-phenylethyl)amino)-4-pyridinyl)-1H-indazol-7-ol;

EXAMPLE 175

'4-(3-((1S,4S)-2,5-diazabicyclo[2.2.1]hept-2-yl)-6-(trifluoromethyl)-1H-indazol-1-yl)-N-((1R)-1-phenylethyl)-2-pyridinamine;

EXAMPLE 176

'1,1-dimethylethyl (1S,4S)-5-(1-(2-((phenylmethyl)amino)-4-pyridinyl)-6-(trifluoromethyl)-1H-indazol-3-yl)-2,5-diazabicyclo[2.2.1]heptane-2-carboxylate;

EXAMPLE 177

'4-(3-((1S,4S)-2,5-diazabicyclo[2.2.1]hept-2-yl)-6-(trifluoromethyl)-1H-indazol-1-yl)-N-(phenylmethyl)-2-pyridinamine; and

EXAMPLE 178

'1,1-dimethylethyl (1S,4S)-5-(1-(2-(((1S)-1-phenylethyl) amino)-4-pyridinyl)-6-(trifluoromethyl)-1H-indazol-3-yl)-2,5-diazabicyclo[2.2.1]heptane-2-carboxylate.

The compounds provided herein are useful for treating a variety of diseases or conditions associated with Kinases, and particularly those related to PKCθ. The following biological assays were used to measure activity of the compounds described therein.

PKCθ Homogeneous Time Resolved Fluorescent (HTRF) Kinase Assay:

The HTRF assay begins with PKCθ in the presence of ATP phosphorylating a biotinylated peptide substrate based on a Thr-substituted PKCα pseudosubstrate sequence (YTASQD-VANRFARKGTLRQKNV). The reaction incubates for 60min. To quench the assay detection reagents are added which both stop the reaction by diluting out the enzyme and chelating the metals due to the presence of EDTA. Once the detection reagents are added, the assay incubates for 60 min to allow for equilibration of the detection reagents.

The PKCθ HTRF assay is comprised of 1 μL of compound in 100% DMSO, 10 μL of ATP and biotinylated peptide substrate, and 5 μL of PKCθ KD for a final volume of 50 μL. The final concentration of PKCα pseudosubstrate is 1 μM. The final concentration of ATP is 25 μM (Km app=69 μM) and the final concentration of PKCθ is 100 pM. Buffer conditions are as follows: 50 mM Tris pH 7.5, 10 mM $MgCl_2$, 10% DMSO, 1.5 mM DTT, 0.03% BSA.

Five μL of assay is quenched by adding it to 45 μL of detection reagent. Detection reagents are as follows: Buffer made of 100 mM Tris, pH 7.5, 100 mM NaCl, 5 mM EDTA, 0.1% BSA, 0.1% Tween20. Added to this buffer prior to reading is Streptavidin allophycocyanin (SA-APC) at a final conc. in the assay of 25 nM, and europilated anti-phospho-Threonine Ab (Eu-anti-pT) at a final conc. of 0.3 nM.

The assay plate is read in Discovery. The Eu-anti-pT is excited at 320 nm and emits at 615 nm to excite the SA-APC, which in turn emits at 655 nm. The ratio of SA-APC at 655 nm (excited due to close proximity to the Eu-anti-pT because of phosphorylation of the peptide) to free Eu-anti-pT at 615 nm will give substrate phosphorylation. Examples 4-39, 41-44, 48-59, 63-69 and 71-178 exhibited activity of better than 50 μM in the PKCθ HTRF assay.

Assays for other PKC isoforms or other kinases are done in a similar way as described above, varying the concentrations of enzyme, peptide substrate, and ATP added to the reaction, depending on the specific activity of the kinase and measured Km's for the substrates.

Anti-CD3/anti-CD28-induced T cell IL-2 Secretion and Proliferation Assay:

The purpose of this assay is to test the potency of T cell receptor (TCR; CD3) and CD28 signaling pathway inhibitors in human T cells. T cells isolated from human peripheral blood lymphocytes (hPBL) are enriched to >90% purity by human Pan T- cell Kit with MACS columns (Miltenyi Biotec). For anti-CD3 and anti-CD28 stimulations, T cells ($1\times10^5$ T cells/well) in proliferation medium (RPMI supplemented with 10% FCS, 50 μm β-mercaptoethanol, 2 mM L-glutamine and 100 units/mL penicillin/streptomycin) are added in duplicate to 96-well plates precoated with anti-CD3 antibody (0.5 ug/mL-Pharmingen) and anti CD28 (2.0 ug/mL-R&D Systems) overnight at 4° C. The T cells are incubated for ~40 h at 37° C. in 5% $CO_2$, then secreted IL-2 in the supernatants is quantified by cytokine ELISA (R&D Systems). The cells remaining in the wells are then pulsed with [$^3$H]-thymidine for 16-18 h to assess the T cell proliferative response. Cells are harvested onto glass fiber filters and $^3$H-thymidine incorporation into DNA is analyzed by liquid scintillation counter. Specific IL-2 production and proliferation are calculated as the mean count in duplicate wells after subtraction of the baseline of syngeneic cultures. Potential inhibitor compounds can be tested for inhibition of this response as described above for anti-CD3 and -CD28 antibodies.

The following compounds exhibit activity of better than 500 μM in anti-CD3/anti-CD28 induced IL-2 secretion in whole human blood:

(S)-{4-[4-(5-Isopropyl-(1S,4S)-2,5-diaza-bicyclo[2.2.1] hept-2-yl)-quinazolin-2-yl]-pyridin-2-yl}-(1-phenyl-ethyl)-amine;

{4-[5-(5-Isopropyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine;

{4-[4-((1S,4S)-2,5-diaza-bicyclo[2.2.1]hept-2-yl)-quinazolin-2-yl]-pyridin-2-yl}-(1-phenyl-ethyl)-amine;

S)-{4-[4-(5-Ethyl-(1S,4S)-2,5-diaza-bicyclo[2.2.1]hept-2-yl)-quinazolin-2-yl]-pyridin-2-yl}-(1-phenyl-ethyl)-amine;

(S)-{4-[4-(5-Methyl-(1S,4S)-2,5-diaza-bicyclo[2.2.1]hept-2-yl)-quinazolin-2-yl]-pyridin-2-yl}-(1-phenyl-ethyl)-amine;

{4-[5-((1S,4S)-2,5-diaza-bicyclo[2.2.1]hept-2-yl)-imidazo [1,2-c]pyrimidin-7-yl]-pyridin-2-yl}-(2-fluoro-benzyl)-amine;

{4-[4-(5-Isopropyl-(1S,4S)-2,5-diaza-bicyclo[2.2.1]hept-2-yl)-quinolin-2-yl]-pyridin-2-yl}-(1-phenyl-ethyl)-amine;

{4-[3-(5-Isopropyl-(1S,4S)-2,5-diaza-bicyclo[2.2.1]hept-2-yl)-indazol-1-yl]-pyridin-2-yl}-(1-phenyl-ethyl)-amine;

{4-[4-((1S,4S)-2,5-diaza-bicyclo[2.2.1]hept-2-yl)-quinolin-2-yl]-pyridin-2-yl}-(1-phenyl-ethyl)-amine;

{4-[3-((1S,4S)-2,5-diaza-bicyclo[2.2.1]hept-2-yl)-indazol-1-yl]-pyridin-2-yl}-(1-phenyl-ethyl)-amine;

Benzyl-{4-[3-((1S,4S)-2,5-diaza-bicyclo[2.2.1]hept-2-yl)-6-fluoro-indazol-1-yl]-pyridin-2-yl}-amine; and Benzyl-{4-[3-((1S,4S)-2,5-diaza-bicyclo[2.2.1]hept-2-yl)-indazol-1-yl]-pyridin-2-yl}-amine.

Anti-CD3/B7.2 Fc-induced T Cell Proliferation and Cytokine Secretion Assay:

The purpose of this assay is to test the potency of T cell receptor (TCR; CD3) and CD28 signaling pathway inhibitors in human T cells. Anti-CD3 (Pharmingen) is coated on 96-well round bottom tissue culture plates (Falcon) overnight at 4° C.; the concentration of anti-CD3 depends on the donor. The plates are washed with PBS (Gibco) the next morning, and then 3 μg/mL of human B7.2 Fc (R&D Systems) is coated for ~4 h at 37° C. T cells are purified from human peripheral blood lymphocytes (hPBL) using magnetic beads from Miltenyi Biotec. T cells are added to the plates after the plates are washed with PBS ($1\times10^5$ T cells/well). Test compounds are diluted to 4 mM in DMSO, and then ½ log dilutions are done in DMSO using a Precision2000 robot (Bio-Tek Instruments) to make a 10-point titration. The compounds are then diluted 1:100 in RPMI medium 1640 (Gibco) supplemented with 10% FBS (JRH Biosciences), 0.1 mM MEM non-essential amino acids (Gibco), 100 units/mL Penicillin, 0.1 mg/mL Streptomycin, 292 μg/mL L-glutamine (Gibco), and 55 μM 2-mercaptoethanol (Gibco). Then the compounds (4×) are added to the cells. Cells are cultured for ~48 h at 37° C. in 5% $CO_2$. Secreted IL-2, TNFα and IFNγ in the supernatants are quantified by electrochemiluminescence (MSD). 20 μL of supernatant is incubated with 110 μL of 2× MSD assay buffer and 20 μl of antibody diluent (1 μg/mL of each detection antibody) in a 3-spot MSD plate (IL-2,TNFα and IFNγ). The plates are covered and incubated overnight at room temperature. A Sector HTS reader (MSD) is used to analyze the cytokine levels. The cells are pulsed with $^3$H-thymidine (ICN) for ~16 h to assess the T cell proliferative response. Cells are harvested onto glass fiber filters (Wallac) and $^3$H-thymidine incorporation into DNA is analyzed by a liquid scintillation counter (Perkin Elmer).

Human Mixed Lymphocyte Reaction (One way MLR):

The purpose of this assay is to test the potency of T cell inhibitors in an in vitro model of allogeneic T cell stimulation. Human peripheral blood lymphocytes (hPBL; 1×10$^5$/well) from one donor are incubated with mitomycin C (30 ug/mL for 1 h)-treated hPBL; 1×10$^5$/well from another donor as allogeneic stimulators in the presence or absence of dilutions of potential inhibitor compound in 96-well round-bottom tissue culture plates. These cultures are incubated at 37° C. in 5% CO$_2$ for 6 days total. The proliferative response of the hPBL is measured by $^3$H-thymidine incorporation (0.5 uCi/well) overnight between days 5 and 6 after initiation of culture. Cells are harvested and $^3$H-thymidine incorporation into DNA is analyzed by liquid scintillation counter.

Jurkat Proliferation/survival Assay:

The purpose of this assay is to test the general anti-proliferative/cytotoxic effect of compounds on the Jurkat human T cell line. Jurkat cells (1×10$^5$/well) are plated in 96-well flat-bottom tissue culture plates with or without compound dilutions and cultured for 72 h at 37° C. in 5% CO$_2$. Viable cell number is determined during the last 4 h of culture by adding 10 μL/well WST-1 dye. WST-1 dye conversion relies on active mitochondrial electron transport for reduction of the tetrazolium dye. The dye conversion is read by OD at 450-600 nm.

Anti-CD3/anti-CD28-induced IL-2Secretion in Whole Human Blood

The purpose of this assay is to test the potency of T cell receptor (TCR; CD3) and CD28 signaling pathway inhibitors in whole human blood. Anti-CD3 antibody (10 ug/mL; R&D Systems) is precoated on the wells of 96-well plates. Compounds are added in T-cell dilution media (Iscoves modified DMEM), supplemented with 0.1% human serum albumin, 5 uM Beta-mercaptoethanol, and 1×Pen/Strep/Glu. Compounds are tested in triplicate. 100 μL of whole human blood (collected in heparinized tubes) is added to each well and the plates are incubated for 30 minutes at 37° C., 5% CO$_2$. Anti-CD28 antibody (2 ug/mL; R&D Systems) is diluted in T-cell dilution media and is added to the wells. The mixture is incubated for 48 h at 37° C., 5% CO$_2$. The cells are then pelleted, and the supernatant collected and IL-2 production determined by ELISA (R&D Systems).

The following compounds exhibit activity of better than 5 μM in anti-CD3/anti-CD28 induced IL-2 secretion in whole human blood:

(S)-{4-[4-(5-Ethyl-(1S,4S)-2,5-diaza-bicyclo[2.2.1]hept-2-yl)-quinazolin-2-yl]-pyridin-2-yl}-(1-phenyl-ethyl)-amine;

(S)-{4-[4-(5-Isopropyl-(1S,4S)-2,5-diaza-bicyclo[2.2.1]hept-2-yl)-quinazolin-2-yl]pyridin-2-yl}-(1-phenyl-ethyl)-amine;

Benzyl-{4-[3-((1S,4S)-2,5-diaza-bicyclo[2.2.1]hept-2-yl)-indazol-1-yl]-pyridin-2-yl}-amine;

{4-[4-((1S,4S)-2,5-Diaza-bicyclo[2.2.1]hept-2-yl)-quinazolin-2-yl]-pyridin-2-yl}-(1-phenyl-ethyl)-amine;

{4-[3-((1S,4S)-2,5-Diaza-bicyclo[2.2.1]hept-2-yl)-indazol-1-yl]-pyridin-2-yl}-[1-(2-fluoro-phenyl)-ethyl]-amine;

{4-[4-(5-Isopropyl-(1S,4S)-2,5-diaza-bicyclo[2.2.1]hept-2-yl)-quinolin-2-yl]-pyridin-2-yl}-(1-phenyl-ethyl)-amine;

{4-[5-((1S,4S)-2,5-Diaza-bicyclo[2.2.1]hept-2-yl)-imidazo[1,2-c]pyrimidin-7-yl]pyridin-2-yl}-(1-phenyl-ethyl)-amine;

(S)-{4-[2-(5-Isopropyl-(1S,4S)-2,5-diaza-bicyclo[2.2.1]hept-2-yl)-pyrimidin-4-yl]pyridin-2-yl}-(1-phenyl-ethyl)-amine;

{4-[3-(5-Isopropyl-(1S,4S)-2,5-diaza-bicyclo[2.2.1]hept-2-yl)-indazol-1-yl]-pyridin-2-yl}-(1-phenyl-ethyl)-amine;

Benzyl-{4-[3-((1S,4S)-2,5-diaza-bicyclo[2.2.1]hept-2-yl)-6-fluoro-indazol-1-yl]-pyridin-2-yl}-amine;

{4-[5-(5-Isopropyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine;

Benzyl-{4-[3-((1S,4S)-2,5-diaza-bicyclo[2.2.1]hept-2-yl)-6-fluoro-indazol-1-yl]-pyridin-2-yl}-amine;

{4-[5-(5-Ethyl-(1S,4S)-2,5-diaza-bicyclo[2.2.1]hept-2-yl)-imidazo[1,2-c]pyrimidin-7-yl]-pyridin-2-yl}-(1-phenyl-ethyl)-amine; and {4-[5-((1S,4S)-2,5-diaza-bicyclo[2.2.1]hept-2-yl)-imidazo[1,2-c]pyrimidin-7-yl]-pyridin-2-yl}-(2-fluoro-benzyl)-amine.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

For the treatment of the disease indications described herein, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrastemal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating a PKC mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

What is claimed is:

1. A compound of formula I

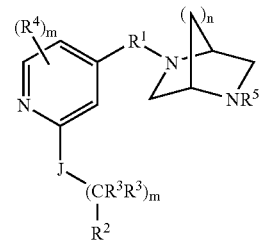

or a pharmaceutically acceptable salt thereof, wherein
J is NH, N($R^b$), O or S;
m is independently at each instance 0, 1, 2 or 3;
n is 1 or 2;
$R^1$ is

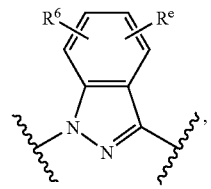

$R^2$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups, and wherein the ring is substituted by 0, 1, 2 or 3 substituents independently selected from $C_{1-8}$ alkyl, $C_{1-4}$ haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$^aC_{2-6}$alkylN$R^aR^a$ and —N$R^aC_{2-6}$alkylO$R^a$;

$R^3$ is independently at each instance H, $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

$R^4$ is independently at each instance $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$—S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

$R^5$ is H or $C_{1-6}$alkyl substituted by 0, 1, 2 or 3 substituents independently selected from $R^d$ and additionally substituted by 0 or 1 substituents selected from $R^f$;

$R^6$ is H, $R^c$, $R^d$, or a $C_{1-6}$alkyl substituted by 1, 2 or 3 substituents independently selected from $R^d$ and additionally substituted by 0 or 1 substituents selected from $R^f$ $R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl and —N($C_{1-4}$alkyl)$C_{1-4}$alkyl;

$R^c$ is independently at each instance a saturated, partially saturated or unsaturated 5-, 6- or 7-membered monocyclic or 6-, 7-, 8-, 9-, 10- or 11-membered bicycic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^d$ is independently at each instance $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

$R^e$ is independently at each instance $R^d$ or H; and $R^f$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$—OC(=O)N($R^a$)S(=O)$_2$ $R^b$, —O$C_{2-6}$alkylN$R^aR^a$, —O$C_{2-6}$alkylO$R^a$, —S$R^a$, —S(=O)$R^b$, —S(=O)$_2R^b$—S(=O)N$R^aR^a$, —S(=O)$_2$ N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2$ $R^b$, —N($R^a$)S(=O)$_2$N$R^aR^a$, —N$R^aC_{2-6}$alkylN$R^aR^a$ and —N$R^aC_{2-6}$alkylO$R^a$.

2. The compound of claim 1, or a pharmaceutically acceptable salt thereof, wherein J is NH, N($R^b$), O or S;

m is independently at each instance 0, 1, 2 or 3;

n is 1;

$R^1$ is

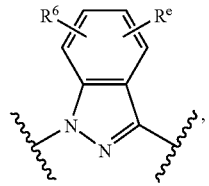

$R^2$ is a ring selected from phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzoclioxyl, benzofuranyl, dihydrobenzofuranyl, cyclopropyl, cyclobutyl, cyclopentyl, cyclohexyl, cycloheptyl, benzothiophenyl and benzimidazolyl, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$ N$R^aR^a$, —N$R^aC_{2-6}$alkylN$R^aR^a$ and —N$R^aC_{2-6}$alkylO$R^a$, $R^3$ is independently at each instance H, $C_{1-8}$alkyl, $C_{1-4}$haloalkyl, halo, —O$R^a$, —S$R^a$ or —N$R^aR^a$;

$R^4$ is $C_{1-8}$alkyl, $C_{1-4}$haloalkyl, halo, cyano, nitro, —$OR^a$, —$SR^a$, —$NR^aR^a$, $NR^aC_{2-6}$alkyflNR$^a$R$^a$ or —$NR^aC_{2-6}$alkylOR$^a$;

$R^5$ is H or $C_{1-6}$alkyl substituted by 0, 1, 2 or 3 substituents independently selected from $R^d$ and additionally substituted by 0 or 1 substituents selected from $R^f$;

$R^6$ is H, $R^c$, $R^d$, or a $C_{1-6}$alkyl substituted by 1, 2 or 3 substituents independently selected from $R^d$ and additionally substituted by 0 or 1 substituents selected from $R^f$;

$R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —$OC_{1-4}$alkyl, —$NH_2$, —$NHC_{1-4}$alkyl, —$N(C_{1-4}$alkyl$)C_{1-4}$alkyl;

$R^c$ is independently, at each instance, phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzodioxyl, benzofaranyl, dihydrobenzofuranyl, cyclopropyl, cyclobutyl, cyclopentyl, cyclohexyl, cycloheptyl, benzothiophenyl or benziniidazolyl, wherein the carbon atoms of the ring are substituted by 0, 1 or 2 oxo groups;

$R^d$ is independently, at each instance, $C_{1-8}$alkyl, $C_{1-4}$haloalkyl, halo, cyano, nitro, —C(=O)$R^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$—S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

$R^e$ is independently, at each instance, $R^d$ or H; and $R^f$ is independently, at each instance, phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzodioxyl, benzofaranyl, dihydrobenzofuranyl, cyclopropyl, cyclobutyl, cyclopentyl, cyclohexyl, cycloheptyl, benzothiophenyl or benzimidazolyl, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)R$^b$, —C(=O)NR$^a$R$^a$, —OR$^a$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alylOR$^a$.

3. The compound of claim 1, or a pharmaceutically acceptable salt thereof, wherein J is NH or NCH$_3$;

m is independently at each instance 0, 1, 2 or 3;

n is 1;

$R^1$ is

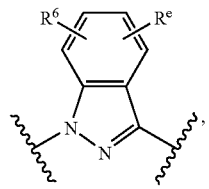

$R^2$ is a ring selected from phenyl, dihydroindenyl, naphthyl, tetrahydronaphthalenyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, imidazolyl, triazolyl, thiazolyl, oxazolyl, isoxazolyl, isothiazolyl, indolyl, isoindolyl, indolinyl, benzoclioxyl, benzofuranyl, dihydrobenzofuranyl, cyclopropyl, cyclobutyl, cyclopentyl, cyclohexyl, cycloheptyl, benzothiophenyl and benzixnidazolyl, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$—OC$_{2-6}$alkylNR$^a$R$^a$, —OC$_{2-6}$alkylOR$^a$—SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$ NR$^a$R$^a$, —NR$^a$C$_{2-6}$alkylNR$^a$R$^a$and —NR$^a$C$_{2-6}$alkylOR$^a$;

$R^3$ is independently at each instance H, $C_{1-8}$alkyl, $C_{1-4}$haloalkyl, halo, —OR$^a$, —SR$^a$or —NR$^a$R$^a$;

$R^4$ is $C_{1-8}$alkyl, $C_{1-4}$haloalkyl, halo, cyano, nitro, —OR$^a$, —SR$^a$, —NR$^a$R$^a$, —NR$^a$C$_{2-6}$alkylNR$^a$R$^a$or —NR$^a$C$_{2-6}$, —alkylOR$^a$;

$R^5$ is H or $C_{1-6}$alkyl substituted by 0, 1, 2 or 3 substituents independently selected from $R^d$ and additionally substituted by 0 or 1 substituents selected from $R^f$;

$R^6$ is H, $R^c$, $R^d$, or a $C_{1-6}$alkyl substituted by 1, 2 or 3 substituents independently selected from $R^d$ and additionally substituted by 0 or 1 substituents selected from $R^f$;

$R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —$OC_{1-4}$alkyl, —$NH_2$, —$NHC_{1-4}$alkyl and —$N(C_{1-4}$alkyl$)C_{1-4}$alkyl;

$R^c$ is independently, at each instance, phenyl, naphthyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, iinidazolyl, triazolyl, thiazolyl, oxazolyl, isoxazolyl, isothiazolyl, indolyl, isoindolyl, indolinyl, benzofuranyl, dihydrobenzofuranyl, cyclopropyl, cyclobutyl, cyclopentyl, cyclohexyl, cycloheptyl, benzothiophenyl or benzimidazolyl, wherein the carbon atoms of the ring are substituted by 0, 1 or 2 oxo groups;

$R^d$ is independently at each instance $C_{1-8}$alkyl, $C_{1-4}$haloalkyl, halo, cyano, nitro, —C(=O)$R^b$, —C(=O)O$R^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

$R^e$ is independently at each instance $R^d$ or H; and $R^f$ is independently at each instance phenyl, naphthyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, pyranyl, furyl, dihydrofuryl, tetrahydrofuryl, pyrrolyl, pyazolyl, ixnidazolyl, triazolyl, thiazolyl, oxazolyl, isoxazolyl, isothiazolyl, indolyl, isoindolyl, indolinyl, benzofuranyl, dihydrobenzofuranyl, cyclopropyl, cyclobutyl, cyclopentyl, cyclohexyl, cycloheptyl, benzothiophenyl or benzimidazolyl, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)R$^b$, —C(=O)NR$^a$R$^a$, —OR$^a$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkyOR$^a$.

4. The compound of claim 3, or a pharmaceutically acceptable salt thereof, wherein $R^6$ is H.

5. The compound of claim 1, or a pharmaceutically acceptable salt thereof, wherein J is NH or NCH$_3$;
m is independently at each instance 0, 1, 2 or 3;
n is 1;
$R^1$ is

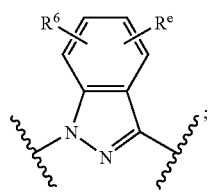

$R^2$ is a ring selected from phenyl, dihydroindenyl, naphthyl, tetrahydronaphthalenyl, pyridyl, pyrimidinyl, pyrrolidinyl, piperidinyl, piperazinyl, morpholinyl, thiophenyl, pyranyl, furyl, dihydrofuryl, tetrahydrofuryl, pyazolyl, imidazolyl, triazolyl, thiazolyl, oxazolyl, isoxazolyl, isothiazolyl, indolyl, isoindolyl, indolinyl, benzodioxyl, benzofuranyl, dihydrobenzofuranyl, cyclopropyl, cyclobutyl, cyclopentyl, cyclohexyl, cycloheptyl, benzothiophenyl and benzimidazolyl, wherein the carbon atoms of the ring are substituted by 0, 1 or 2 oxo groups, and wherein the ring is substituted by 0, 1, 2 or 3 substituents independently selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$—S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

$R^3$ is independently at each instance H, —CH$_3$, —CH$_2$, CH$_3$, or —OR$^a$;

$R^4$ is absent;

$R^5$ is H, —CH$_3$, —CH$_2$CH$_3$, —C(=O)CH(OH)CH$_3$, —SO$_2$CH$_3$, —C(=O)CH(CH$_3$)OC(=O)CH$_3$, -propyl, -isopropyl, —CH$_2$CHCF$_2$, -n-butyl, -t-butyl, -isobutyl, —(CH$_2$)$_2$COOH, —(OH2)$_2$COOCH$_3$, —(CH2)$_2$OPh, —CH(CH$_3$)ethyl, —CH(CH3)CF$_3$, -cyclopentyl or —OR$^a$;

$R^6$ is H, —CH$_3$ or —CH$_2$CH$_3$;

$R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —OC$_{1-4}$alkyl, —NH$_2$, —NHC$_{1-4}$alkyl and —N(C$_{1-4}$alkyl)C$_{1-4}$alkyl; and $R^e$ is independently, at each instance, H, Cl, F, Br, I, CH$_3$, NO2, NHSO$_2$CH$_3$, OH, CF$_3$ or N-Acetyl.

6. A compound, or a pharmaceutically acceptable salt thereof, selected from:

5-{1-[2-((S)-1-Phenyl-ethylamino)-pyridin-4-yl]-1H-indazol-3-yl-}-(1S,4S)-2,5-diaza-bicyclo[2.2.1]heptane-2-carboxylic acid tert-butyl ester;

(S)-{4-[3-((1S, 4S)-2,5-Diaza-bicyclo[2.2.1]hept-2-yl)-indazol-1-yl]-pyridin-2-yl}-(1-phenyl-ethyl)-amine;

(S)-{4-[3-(5-Isopropyk(1S,4S)-2,5-diaza-bicyclo[2.2.1]hept-2-yl)-indazol-1-yl]-pyridin-2-yl}-(1-phenyl-ethyl)-amine;

'1,1-dimethylethyl 5-(1-(2-(((1S)-1-phenylethyl)amino)-4-pyridinyl)-1H-indazol-3-yl)-2,5-diazabicyclo[2.2.1]heptane-2-carboxylate;

'4-(3-(5-(1-methylethyl)-2,5-diazabicyclo[2.2.1]hept-2-yl)-1H-indazol-1-yl)-N-(phenylmethyl)-2-pyridinamine;

'4-(3-(5-(1-methylethyl)-2,5-diazabicyclo[2.2.1]hept-2-yl)-1H-indazol-1-yl)-N-(phenylmethyl)-2-pyridinamine;

'N-((2-fluorophenyl)methyl)-4-(3-(5-(1-methylethyl)-2,5-diazabicyclo[2.2.1]hept-2-yl)-1H-indazol-1-yl)-2-pyridinamine;

'4-(3-(2,5-diazabicyclo[2.2.1]hept-2-yl)-1H-indazol-1-yl)-N-((2-fluorophenyl)methyl)-2-pyridinamine;

'4-(3-(2,5-diazabicyclo[2.2.1]hept-2-yl)-1H-indazol-1-yl)-N-(phenylmethyl)-2-pyridinamine;

'4-(3-(2,5-diazabicyclo[2.2.1]hept-2-yl)-5-fluoro-1H-indazol-1-yl)-N-((1S)-1-phenylethyl)-2-pyridinamine;

'4-(3-(2,5-diazabicyclo[2.2.1]hept-2-yl)-1H-indazol-1-yl)-N-((2-fluorophenyl)methyl)-2-pyridinamine;

'4-(3-(5-methyl-2,5-diazabicyclo[2.2.1]hept-2-yl)-1H-indazol-1-yl)-N-(phenylmethyl)-2-pyridinamine;

'4-(5-fluoro-3-(5-methyl-2,5-diazabicyclo[2.2.1]hept-2-yl)-1H-indazol-1-yl)-N-((1S)-1-phenylethyl)-2-pyridinamine;
'N-((2-fluorophenyl)methyl)-4-(3-(5-methyl-2,5-diazabicyclo[2.2.1]hept-2-yl)-1H-indazol-1-yl)-2-pyridinamine;
'4-(3-(5-ethyl-2,5-diazabicyclo[2.2.1]hept-2-yl)-1H-indazol-1-yl)-N-(phenylmethyl)-2-pyridinamine;
'4-(5-fluoro-3-(5-(1-methylethyl)-2,5-diazabicyclo[2.2.1]hept-2-yl)-1H-indazol-1-yl)-N-((1S)-1-phenylethyl)-2-pyridinamine;
'4-(3-(2,5-diazabicyclo[2.2.1]hept-2-yl)-1H-indazol-1-yl)-N-phenyl-2-pyridinamine;
'4-(3-(2,5-diazabicyclo[2.2.1]hept-2-yl)-6-fluoro-1H-indazol-1-yl)-N-(phenylmethyl)-2-pyridinamine;
'4-(3-(2,5-diazabicyclo[2.2.1]hept-2-yl)-1H-indazol-1-yl)-N-((1S)-1-(2-fluorophenyl)ethyl)-2-pyridmaimne;
'4-(3-(2,5-diazabicyclo[2.2.1]hept-2-yl)-6-fluoro-1H-indazol-1-yl)-N-((1S)-1-phenylethyl)-2-pyridinanilne;
'4-(3-(2,5-diazabicyclo[2.2.1]hept-2-yl)-7-fluoro-1H-indazol-1-yl)-N-((1S)-1-phenylethyl)-2-pyridinamine;
'4-(5ethyl2,5-diazabicyclo[2.2.1]hept-2-yl)-7-fluoro-1H-indazol-1-yl)-N-((1S)-1-phenylethyl)-2-pyridinamine;
'4-(3-(5-ethyl-2,5-diazabicyclo[2.2.1]hept-2-yl)-1H-indazol-1-yl)-N-((1S)-1-phenylethyl)2-pyridinamine;
'4-(6-fluoro-3-(5-(1-methylethyl)-2,5-diazabicyclo[2.2.1]hept-2-yl)-1H-indazol-1-yl)-N-(phenylmethyl)-2-pyridinamine;
'4-(6-fluoro-3-(5-methyl-2,5-diazabicyclo[2.2.1]hept-2-yl)-1H-indazol-1-yl)-N-(phenylmethyl)-2-pyridinamine:
'4-(4-chloro-3-(2,5-diazabicyclo[2.2.1]hept-2-yl)-1H-indazol-1-yl)-N-((1S)-1-phenylethyl)-2-pyridinamine;
'4-(4-chloro-3-(5-(1-methylethyl)-2,5-diazabicyclo[2.2.1]hept-2-yl)-1H-indazol-1-yl)-N-((1S)-1-phenylethyl)-2-pyridinamine;
'4-(4-chloro-3-(5-ethyl-2,5-diazabicyclo[2.2.1]hept-2-yl)-1H-indazol-1-yl)-N-((1S)-1-phenylethyl)-2-pyridinamine;
'4-(3-(5-ethyl-2,5-diazabicyclo[2.2.1]hept-2-yl)-6-fluoro-1H-indazol-1-yl)-N-(phenylmethyl)-2-pyridinamine;
'4-(3-(2,5-diazabicyclo[2.2.1]hept-2-yl)-6-nitro-1H-indazol-1-yl)-N-((1S)-1-phenylethyl)-2-pyridinamine;
'4-(4-chloro-3-((1S,4S)-2,5-diazabicyclo[2.2.1]hept-2-yl)-1H-indazol-1-yl)-N-(phenylmethyl)-2-pyridinamine;
'4-(6-chloro-3-((1S,4S)-2,5-diazabicyclo[2.2.1]hept-2-yl)-1H-indazol-1-yl)-N-((1S)-1-phenylethyl)-2-pyridinamine;
'4-(3-((1S,4S)-2,5-diazabicyclo[2.2.1]hept-2-yl)-6-fluoro-1H-indazol-1-yl)-N-methyl-N-(phenylmethyl)-2-pyridinamine;
'4-(3-((1S,4S)-2,5-diazabicyclo[2.2.1]hept-2-yl)-6-methyl-1H-indazol-1-yl)-N-(phenylmethyl)-2-pyridinamine;
1,1-dimethylethyl (1S,4S)-5-(4-chloro-1-(2-((phenylmethyl)amnino)-4-pyridinyl)-1H-indazol-3-yl)-2,5-diazabicyclo[2.2.1]heptane-2-carboxylate;
'4-(3-((1S,4S)-2,5-diazabicyclo[2.2.1]hept-2-yl)-6-methyl-1H-indazol-1-yl)-N-((1R)-1-phenylethyl)-2-pyridinamine;
1,1-dimethylethyl (1S,4S)-5-(6-methyl-1-(2-(((1R)-1-phenylethyl)amino)-4-pyridinyl)-1H-indazol-3-yl)-2,5-diazabicyclo[2.2.1]heptane-2-carboxylate;
'4-(6-methyl-3-((1S,4S)-5-(1-methylethyl)-2,5-diazabicyclo[2.2.1]hept-2-yl)-1H-indazol-1-yl)-N-((1R)-1-phenylethyl)-2-pyridinamine;
'3-((1S,4S)-2,5-diazabicyclo[2.2.1]hept-2-yl)-1-(2-(((1S)-1-phenylethyl)amino)-4-pyridinyl)-1H-indazol-6-amine;
'N-(3-((1S,4S)-2,5-diazabicyclo[2.2.1]hept-2-yl)-1-(2-(((1S)-1-phenylethyl)amino)-4-pyridinyl)-1H-indazol-6-yl)acetamide;
'N-(3-((1S,4S)-2,5-diazabicyclo[2.2.1]hept-2-yl)-1-(2-(((1S)-1-phenylethyl)amino)-4-pyridinyl)-1H-indazol-6-yl)methanesulfonamide;
'3-((1S,4S)-2,5-diazabicyclo[2.2.1]hept-2-yl)-6-nitro-1-(2-(((1S)-1-phenylethyl)amino)-4-pyridinyl)-1H-indazol-7-ol;
'4-(3-((1S,4S)-2,5-diazabicyclo[2.2.1]hept-2-yl)-6-(trifluoromethyl)-1H-indazol-1-yl)-N-((1R)-1-phenylethyl)-2-pyridinamine;
'1,1-dimethylethyl (1S,4S)-5-(1-(2-((phenylmethyl)amino)-4-pyridinyl)-6-(trifluoromethyl)-1H-indazol-3-yl)-2,5-diazabicyclo[2.2.1]heptane-2-carboxylate;
'4-(3-((1S,4S)-2,5-diazabicyclo[2.2.1]hept-2-yl)-6-(trifluoromethyl)-1H-indazol-1-yl)-N-(phenylmethyl)-2-phenylmethyl;
'1,1-dimethylethyl (1S,4S)-5(1-(2-(((1S)-1-phenylethyl(amino)-4-pyridinyl)-6-(trifluoromethyl)-1H-indazol-3-yl)-2,5-diazabicyclo[2.2.1]heptane-2-carboxylate;
(S)-Benzyl-{4-[3-((1S,4S)-2,5-diaza-bicyclo[2.2.1]hept-2-yl)-6-fluoro-indazol-1-yl]-pyridin-2-yl}-amine;
Benzyl-{4-[3-((1S,4S)-2,5-diaza-bicyclo[2.2.1]hept-2-yl)-6-fluoro-indazol-1-yl]-pyridin-2-yl}-amine; and
Benzyl-{4-[3-(1S,4S)-2,5-diaza-bicyclo[2.2.1]hept-2-yl)-indazol-1-yl]-pyridin-2-yl}-amine.

7. A pharmaceutical composition comprising a compound according to claim 1 and a pharmaceutically acceptable carrier.

8. A pharmaceutical composition comprising a compound according to claim 6 and a pharmaceutically acceptable carrier.

9. A method of treatment of respiratory allergies, asthma, hayfever, allergic rhinitis, skin allergies, or a combination thereof in a mammal comprising administering an effective amount of a compound according to any of claims 1, 2-4 and 5 to the mammal.

* * * * *

UNITED STATES PATENT AND TRADEMARK OFFICE
CERTIFICATE OF CORRECTION

PATENT NO. : 7,582,631 B2
APPLICATION NO. : 11/034042
DATED : September 1, 2009
INVENTOR(S) : Dominguez et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1241 days.

Signed and Sealed this

Fourteenth Day of September, 2010

David J. Kappos
*Director of the United States Patent and Trademark Office*